United States Patent
Hobson et al.

(10) Patent No.: US 12,121,589 B2
(45) Date of Patent: Oct. 22, 2024

(54) ANTI-CD19 ANTIBODY DRUG CONJUGATES

(71) Applicant: AbbVie Biotherapeutics Inc., North Chicago, IL (US)

(72) Inventors: Adrian D. Hobson, Shrewsbury, MA (US); Christopher C. Marvin, Grayslake, IL (US); James W. Purcell, San Francisco, CA (US)

(73) Assignee: ABBVIE BIOTHERAPEUTICS INC., North Chicago, IL (US)

( * ) Notice: Subject to any disclaimer, the term of this patent is extended or adjusted under 35 U.S.C. 154(b) by 0 days.

(21) Appl. No.: 18/335,636

(22) Filed: Jun. 15, 2023

(65) Prior Publication Data

US 2024/0100181 A1 Mar. 28, 2024

Related U.S. Application Data

(60) Provisional application No. 63/488,302, filed on Mar. 3, 2023, provisional application No. 63/366,520, filed on Jun. 16, 2022.

(51) Int. Cl.
*A61K 47/68* (2017.01)
*A61P 35/00* (2006.01)

(52) U.S. Cl.
CPC ...... *A61K 47/6849* (2017.08); *A61K 47/6803* (2017.08); *A61K 47/6889* (2017.08); *A61P 35/00* (2018.01)

(58) Field of Classification Search
CPC ............ A61K 47/6849; A61K 47/6803; A61K 47/6889; A61P 35/00
See application file for complete search history.

(56) References Cited

U.S. PATENT DOCUMENTS

| | | | |
|---|---|---|---|
| 7,968,687 | B2 | 6/2011 | McDonagh et al. |
| 8,642,292 | B2 | 2/2014 | Sandig et al. |
| 8,822,439 | B2 | 9/2014 | Glossop et al. |
| 2006/0134709 | A1 | 6/2006 | Stavenhagen et al. |
| 2010/0104509 | A1 | 4/2010 | King et al. |
| 2022/0184208 | A1 | 6/2022 | Fingerle-Rowson et al. |
| 2022/0265842 | A1 | 8/2022 | Hobson et al. |

FOREIGN PATENT DOCUMENTS

| | | |
|---|---|---|
| WO | 2009052431 A2 | 4/2009 |
| WO | 2009054863 A2 | 4/2009 |
| WO | 2016180941 A1 | 11/2016 |
| WO | 2017210471 A1 | 12/2017 |
| WO | 2019106608 A1 | 6/2019 |
| WO | 2020010235 A1 | 1/2020 |
| WO | 2020109251 A1 | 6/2020 |
| WO | 2022117799 A2 | 6/2022 |

OTHER PUBLICATIONS

Burger, Jan A. et al. "Targeting B cell receptor signalling in cancer: preclinical and clinical advances." Nat Rev Cancer. Mar. 2018;18(3):148-167.
Cartron, Guillaume et al. "Therapeutic activity of humanized anti-CD20 monoclonal antibody and polymorphism in IgG Fc receptor FcgammaRIIIa gene." Blood. Feb. 1, 2002;99(3):754-8.
Davis, James A. et al. "Newly approved anti-CD19 monoclonal antibodies for the treatment of relapsed or refractory diffuse large B-cell lymphoma." J Oncol Pharm Pract. Apr. 2022;28(3):686-690.
Disis, Mary L. et al. "Therapeutic and Prophylactic Antitumor Activity of an Oral Inhibitor of Fucosylation in Spontaneous Mammary Cancers." Mol Cancer Ther. May 2020;19(5):1102-1109.
Hicks, Stuart W. et al. "The novel CD19-targeting antibody-drug conjugate huB4-DGN462 shows improved anti-tumor activity compared to SAR3419 in CD19-positive lymphoma and leukemia models." Haematologica. Aug. 2019;104(8):1633-1639.
Jagadeesh, Deepa et al. "Antibody Drug Conjugates (ADCs): Changing the Treatment Landscape of Lymphoma." Curr Treat Options Oncol. Oct. 2016;17(10):55.
Kaufman, Randal J. et al. "Amplification and expression of sequences cotransfected with a modular dihydrofolate reductase complementary dna gene." J Mol Biol. Aug. 25, 1982;159(4):601-21.
Koene Harry R. et al. "Fc gammaRIIIa-158V/F polymorphism influences the binding of IgG by natural killer cell Fc gammaRIIIa, independently of the Fc gammaRIIIa-48L/R/H phenotype." Blood. Aug. 1, 1997;90(3):1109-14.
Okeley, Nicole M. et al. "Development of orally active inhibitors of protein and cellular fucosylation." Proc Natl Acad Sci U S A. Apr. 2, 2013;110(14):5404-9.
Phelan, James D. et al. "A multiprotein supercomplex controlling oncogenic signalling in lymphoma." Nature. Aug. 2018;560(7718):387-391.
Urlaub, Gail et al. "Isolation of Chinese hamster cell mutants deficient in dihydrofolate reductase activity." Proc Natl Acad Sci U S A. Jul. 1980;77(7):4216-20.
Watkins, Marcus P. et al. "CD19-targeted immunotherapies for treatment of patients with non-Hodgkin B-cell lymphomas." Expert Opin Investig Drugs. Jul. 2018;27(7):601-611.
Wu, Jianming et al. "A novel polymorphism of FcgammaRIIIa (CD16) alters receptor function and predisposes to autoimmune disease." J Clin Invest. Sep. 1, 1997;100(5):1059-70.
Zammarchi, Francesca et al. "ADCT-402, a PBD dimer-containing antibody drug conjugate targeting CD19-expressing malignancies." Blood. Mar. 8, 2018;131(10):1094-1105.
Chang, C. A. et al., "Preclinical development of ABBV-319: A CD19-targeting glucocorticoid receptor modulator (GRM) agonist antibody-drug conjugate (ADC) for the treatment of B-cell malignancies", AACR (2023), vol. 83: (7_Supplement): Abstract 6308, 2 pgs.
Chang, C. A. et al., "Preclinical development of ABBV-319: A CD19-targeting glucocorticoid receptor modulator (GRM) agonist antibody-drug conjugate (ADC) for the treatment of B-cell malignancies", AACR (Apr. 14, 2023) Poster, 1 pg.
Purcell, J. "ABBV-319: A First-in-Class Glucocorticoid Receptor Modulator (GRM) Agonist ADC for the Treatment of B-cell Malignancies", AACR (2023), vol. 83 (7_Supplement): ND01 Astract, 1 pg.

(Continued)

*Primary Examiner* — Robert S Landsman
(74) *Attorney, Agent, or Firm* — Fox Rothschild LLP

(57) ABSTRACT

The present disclosure provides anti-CD19 antibody drug conjugates (ADCs), including compositions and methods of using such ADCs.

Figure 1:
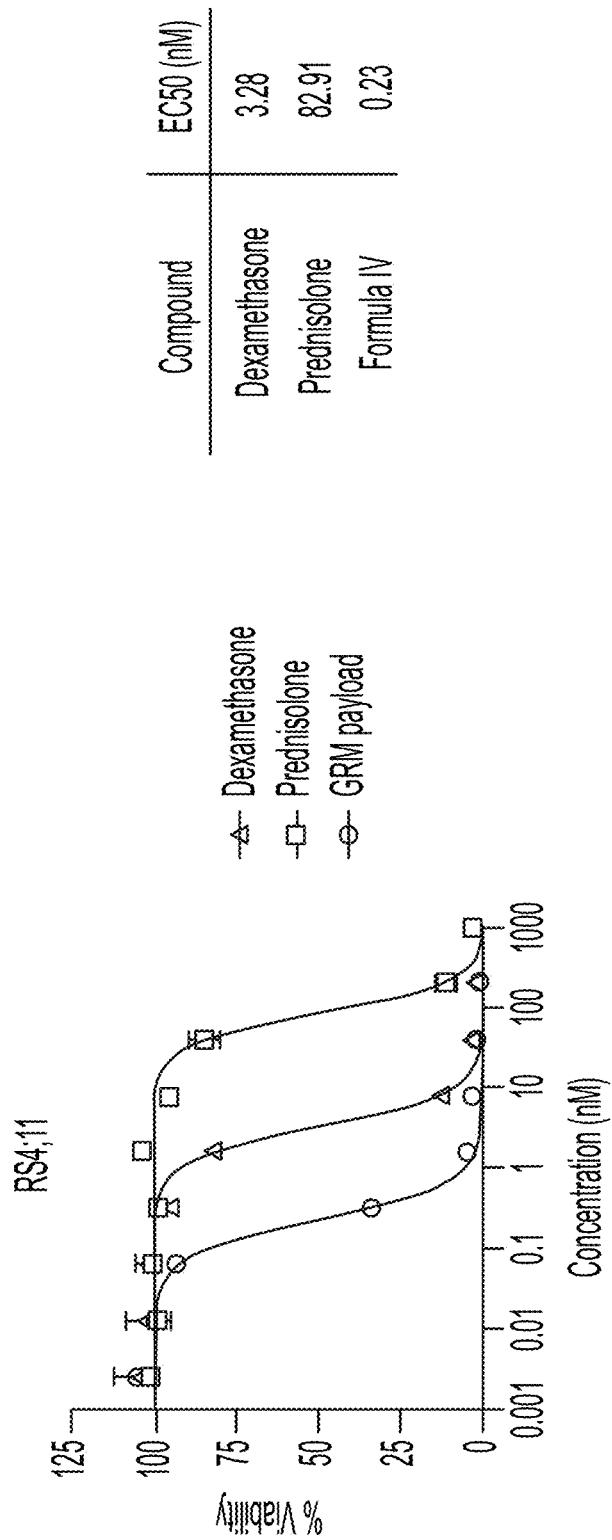

3 Claims, 18 Drawing Sheets
Specification includes a Sequence Listing.

(56) References Cited

OTHER PUBLICATIONS

Purcell, J. "ABBV-319: A First-in-Class Glucocorticoid Receptor Modulator (GRM) Agonist ADC for the Treatment of B-cell Malignancies", AACR Annual Meeting (2023), 16 pgs.

Dennis H., "AACR Orlando 2023: New Drug Candidates," Apr. 2023, [retrieved on Aug. 31, 2023] Retrieved from the Internet: [URL: https://drughunter.com/aacr-orlando-2023-new-drug-candidates/].

Kabat E.A., et al., "Accession No. PS91-192898, Sequences of Proteins of Immunological Interest," National Institutes of Health Publication No. 91-3242, 5th Edition, 1991, pp. 647-669.

Moshe K., "A First-in-Human Phase Study of Abbv-319, an Antibody-Drug 19 Conjugate Composed of a CD19 Antibody Linked to a Potent Proprietary Glucocorticoid Receptor Modulator, in Patients with Relapsed or Refractory B-Cell Malignancies," Blood, American Society of Hematology, Nov. 2022. [retrieved on Aug. 31, 2023] Retrieved from the Internet: [URL: https://ashpublications.org/blood/article/140/Supplement%201/3746/487863/A-First-in-Human-Phase-1-Study-of-Abbv-319-an].

International Search Report and Written Opinion for Application No. PCT/US2023/068496, mailed on Sep. 11, 2023, 20 pages.

Chang, C. A. et al., "ABBV-319: A CD19-Targeting Glucocorticoid Receptor Modulator Antibody-Drug Conjugate Therapy for B-Cell Malignancies", downloaded from http://ashpublications.org/blood/article-pdf/doi/10.1182/blood.2024023849/2224541/blood.2024023849.pdf by guest on May 8, 2024, 37 pgs.

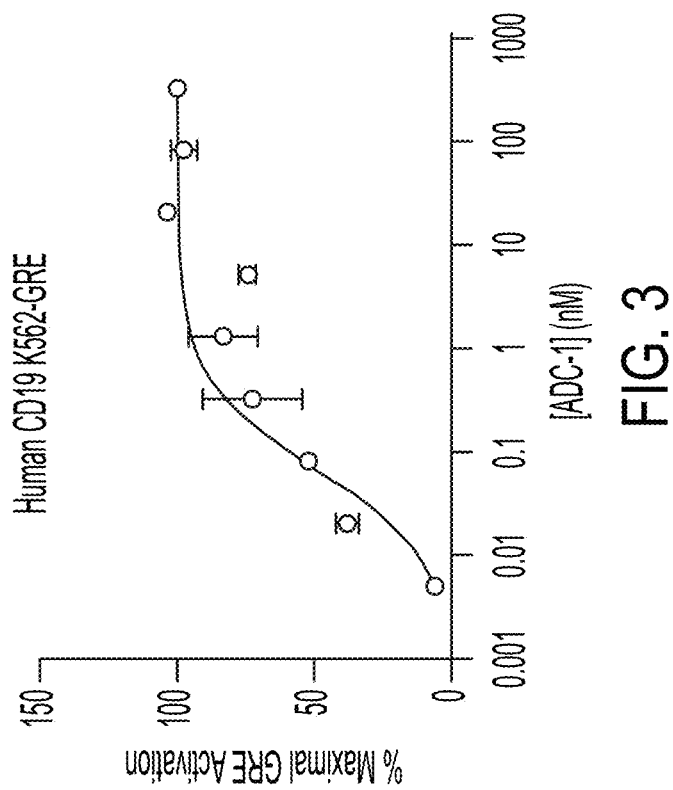

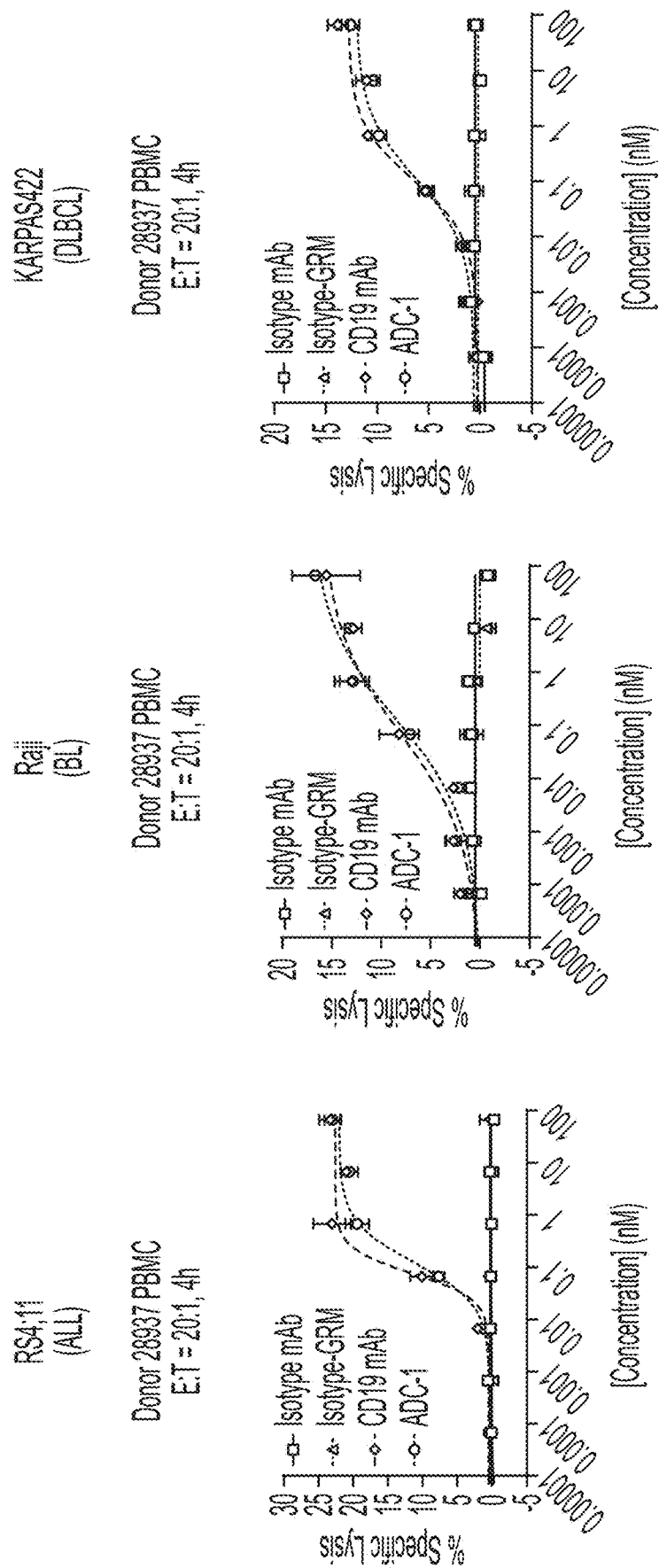

ANTI-CD19 ANTIBODY DRUG CONJUGATES

1. CROSS REFERENCE TO RELATED APPLICATIONS

This application claims the benefit of and priority to U.S. Provisional Patent Application No. 63/366,520, filed Jun. 16, 2022, and U.S. Provisional Patent Application No. 63/488,302, filed Mar. 3, 2023, the disclosures of which are incorporated herein by reference in their entireties for all purposes.

2. SEQUENCE LISTING

The instant application contains a Sequence Listing which has been submitted electronically in .xml format and is hereby incorporated by reference in its entirety. Said .xml copy, created on May 10, 2024, is named SeqList-350794-46701.xml and is 21,125 bytes in size.

3. TECHNICAL FIELD

The present application pertains to, among other things, novel anti-CD19 antibody drug conjugates (ADCs), and methods of making the same.

4. BACKGROUND

CD19 is a B-cell marker and is a co-activator of the B-cell receptor (BCR) complex which activates downstream proteins such as PI3K resulting in a proliferative phenotype. Due to this mechanism, CD19 is a required B-cell antigen, and loss of CD19 expression by CRISPR or RNAi renders normal B-cells and B-cell cancer lines non-viable. CD19 is a clinically validated target with high expression across B-cell malignancies (e.g., DLBCL, FL, CLL).

Systemic glucocorticoids are used in the treatment of B-cell malignancies. These systemic steroids have robust monotherapy activity at high doses, but can result in chronic steroid-associated toxicities, limiting dosing and efficacy potential. Glucocorticoids function by binding the intracellular glucocorticoid receptor (GR) which then traffics to the nucleus where it binds glucocorticoid response elements (GRE) driving transcriptional activation. The steroid-induced transcriptional changes include upregulation of proapoptotic proteins (e.g., BIM, BAX), reduction of anti-apoptotic proteins (e.g., BCL2), and inhibition of $NF_\kappa B$ proliferation signals, which ultimately results in apoptotic cancer cell death.

Therefore, a need exists in the art for an agent that will deliver a glucocorticoid modulator to treat diffuse large B-cell lymphoma (DLBCL), acute lymphoblastic leukemia (ALL), follicular lymphoma (FL), and chronic lymphocytic leukemia (CLL).

5. SUMMARY

The present invention provides for antibody drug conjugates that target B-cells via an anti-CD19 antibody linked to a glucocorticoid receptor modulator (GRM) agonist payload and provides a novel approach for treating diffuse large B-cell lymphoma (DLBCL), acute lymphoblastic leukemia (ALL), follicular lymphoma (FL), and chronic lymphocytic leukemia (CLL). The anti-CD19 GRM agonist ADCs described herein were engineered to have distinct mechanisms of action: (1) targeted delivery of a potent glucocorticoid receptor modulator (GRM) agonist payload, (2) inhibition of CD19 signaling, and (3) Fc effector functions such as antibody dependent cellular cytotoxicity (ADCC) and antibody dependent cellular phagocytosis (ADCP) via CD19 antibody afucosylation. Unlike traditional cytotoxic ADCs, the GRM payload is an agonist that binds the intracellular glucocorticoid receptor (GR) which then traffics to the nucleus driving sustained glucocorticoid response element (GRE) associated transcriptional events, including modulation of apoptotic regulators resulting in payload-driven apoptotic cell death. ADCC is a highly effective mechanism in B-cell malignancies. In an embodiment, the anti-CD19 antibody of the ADC is engineered to maintain increased ADCC activity following conjugation to the GRM agonist payload. By engineering the molecule in this way, anti-CD19 GRM agonist ADCs are multi-modal antibody drug conjugates designed to have robust single agent activity and provide significant clinical benefit in a variety of B-cell malignancies.

In certain aspects, the present invention provides for anti-CD19 antibody-drug conjugates comprising the following structure:

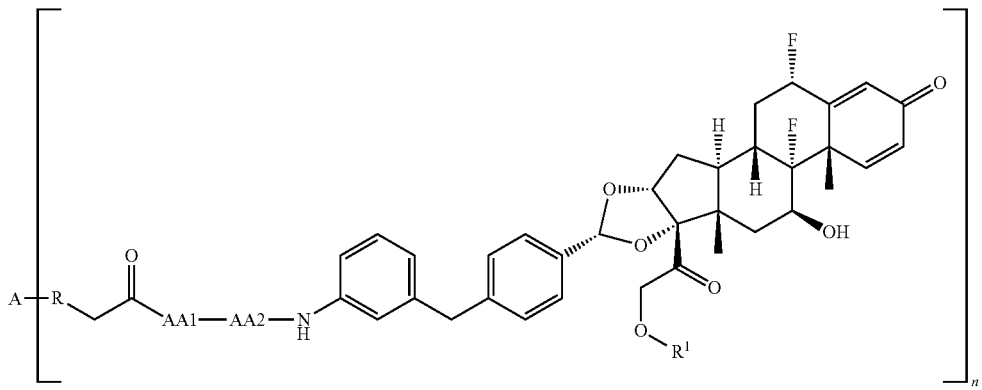

wherein:
A is an antibody;
R is the point of attachment of the antibody via a cysteine residue of the antibody providing an —S— group when linked;
AA1 and AA2 are Alanine (Ala);
$R^1$ is hydrogen or $-P(=O)(OH)_2$;
n is an integer from 1 to 10;

wherein the antibody is an anti-CD19 antibody comprising
a heavy chain variable region comprising a CDR-H1 domain, CDR-H2 domain, and a CDR-H3 domain; and
a light chain variable region comprising a CDR-L1 domain, a CDR-L2 domain, and a CDR-L3 domain, wherein
CDR-H1 comprises the amino acid sequence GFTFTTYWIN (SEQ ID NO: 1),
CDR-H2 comprises the amino acid sequence NIYPSDSYTNYNQKFKD (SEQ ID NO: 2),
CDR-H3 comprises the amino acid sequence EDYYGSSSYYAMDY (SEQ ID NO: 3);
CDR-L1 comprises the amino acid sequence KASQDVGTAVA (SEQ ID NO: 4),
CDR-L2 comprises the amino acid sequence WASTRHT (SEQ ID NO: 5), and
CDR-L3 comprises the amino acid sequence QQYSTYPLT (SEQ ID NO: 6).

6. BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1: In vitro cytotoxicity assay of the GRM payload compared to approved small molecule steroids (dexamethasone and prednisolone). The % cell viability of RS4; 11 relative to the vehicle control after 5-day compound treatment are displayed. The $EC_{50}$ of each compound is summarized in the table.

Figure 2:
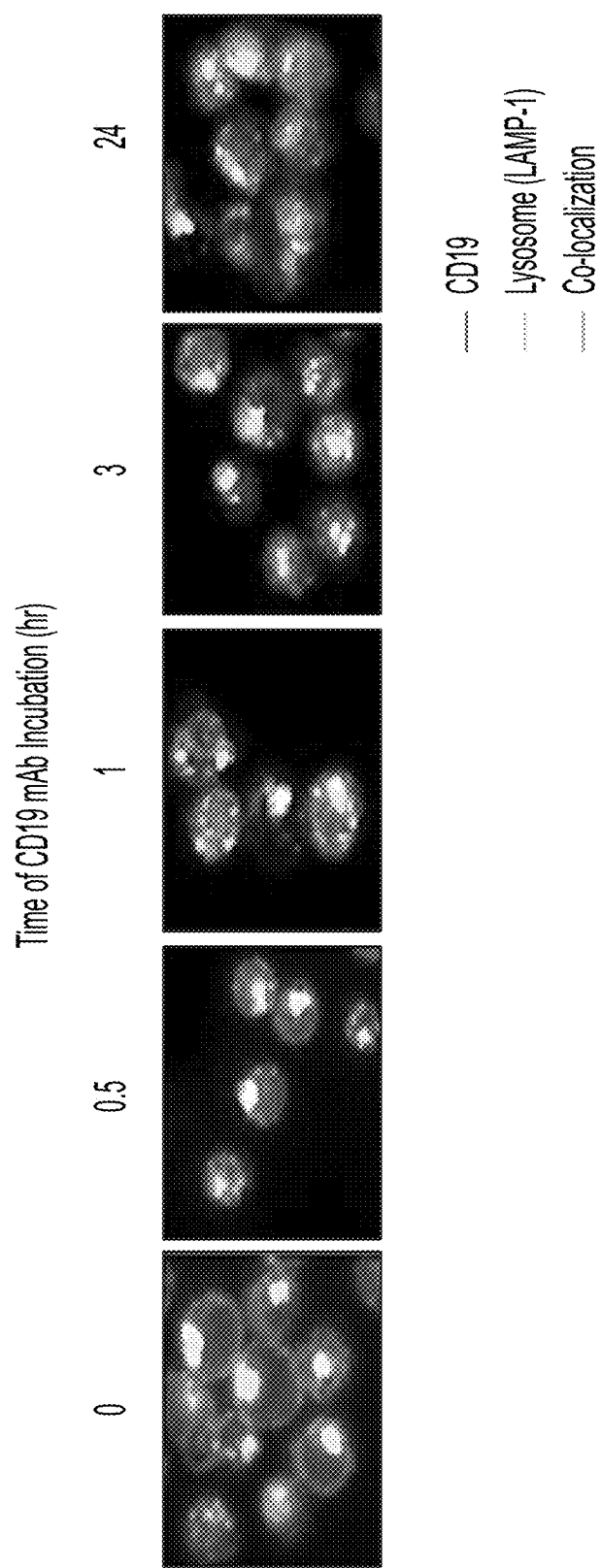

FIG. 2: CD19 mAb induces internalization of CD19 to the lysosome. Immunofluorescence staining showing the localization of CD19 receptor to the lysosomal compartment after CD19 mAb treatment in RS4; 11. LAMP-1 is used as a marker of the lysosome compartment.

FIG. 3: ADC-1 induces transcriptional activation of glucocorticoid response element (GRE) luciferase reporter. K562 cells expressing human CD19 were treated with ADC-1 for 72 hours. The % maximal GRE activation is calculated by dividing the GRE luminescence signal at each concentration by the GRE luminescence signal at 333 nM.

Figures 4A, 4B:
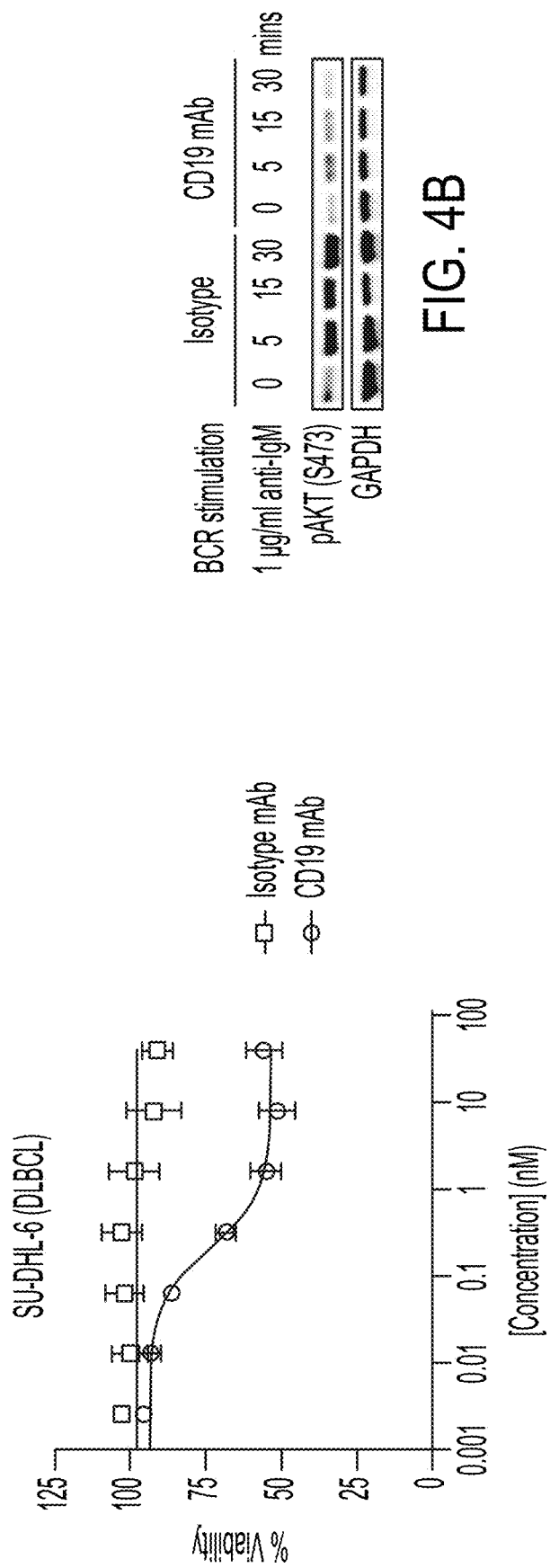

FIGS. 4A-4B: CD19 mAb inhibits DLBCL cell proliferation and AKT activation in vitro. A, The % viability of SU-DHL-6 relative to vehicle control after 5-day treatment with isotype or CD19 mAb. B, SU-DHL-6 cells were treated with isotype or CD19 mAb for an hour and then stimulated with 1 μg/ml anti-IgM for indicated time before cell lysis. The phosphorylation of S473 on AKT was detected via immunoblotting and GAPDH is used as the loading control.

Figure 5B:
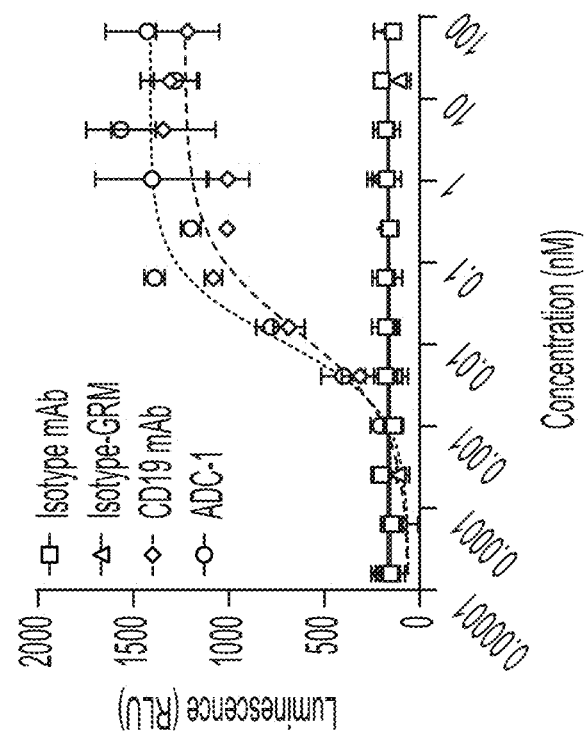
Figure 5A:
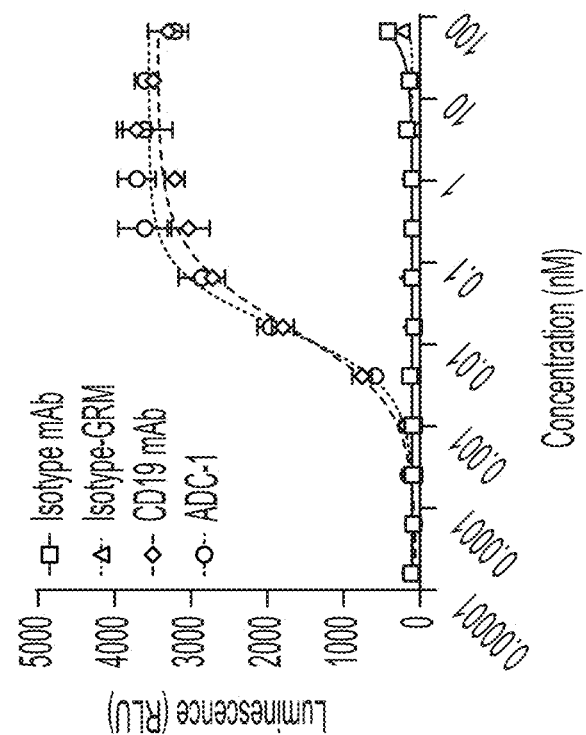

FIGS. 5A-5B: CD19 mAb and ADC-1 induce NFAT activation in Jurkat reporter cells expressing FcγRIIIa V158 and F158 allotypes. A and B, Raji cells were treated with dose-titrated antibody or ADC and co-incubated with Jurkat cells expressing V158 (A) and F158 (B) FcγRIIIa variants. The luminescence signal after 4-hour (A) or 16-hour (B) of incubation are displayed.

FIGS. 6A-6C: CD19 mAb and ADC-1 induce ADCC on B-cell malignancy cell-lines in PMBC co-culture ADCC assay ex vivo. A-C, RS4; 11 (A), Raji (B) and KARPAS422 (C) are incubated with dose-titrated antibody or ADC and co-incubated with primary PBMC at an effector to target ratio (E:T) of 20:1 for 4 hours. The % specific lysis of the cells were calculated relative to the untreated sample.

Figure 7B:
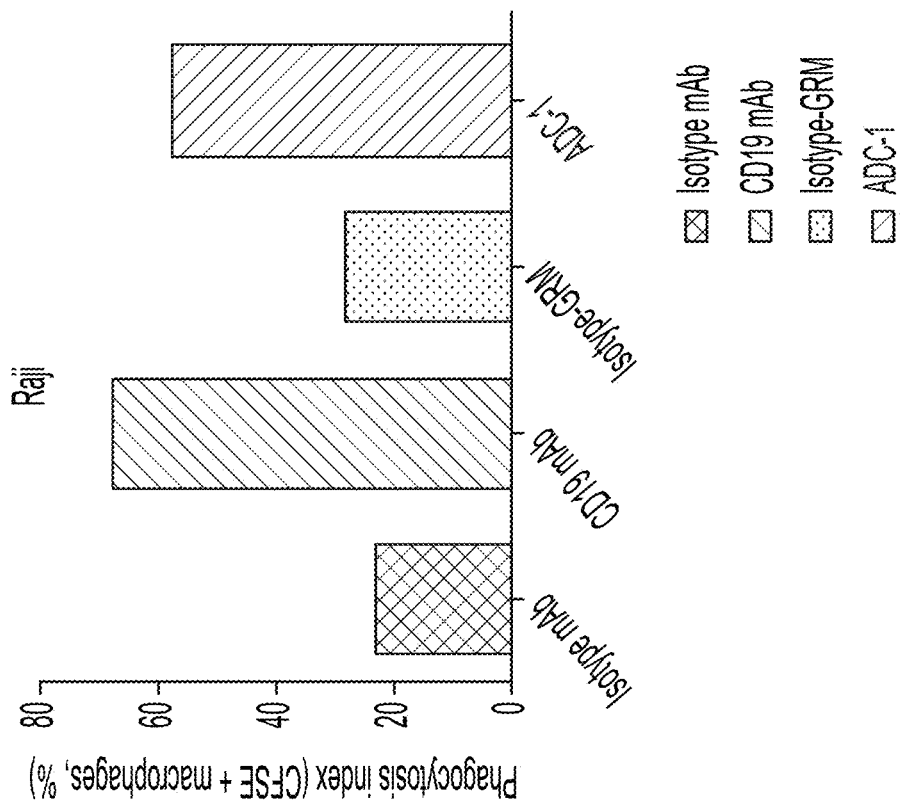
Figure 7A:
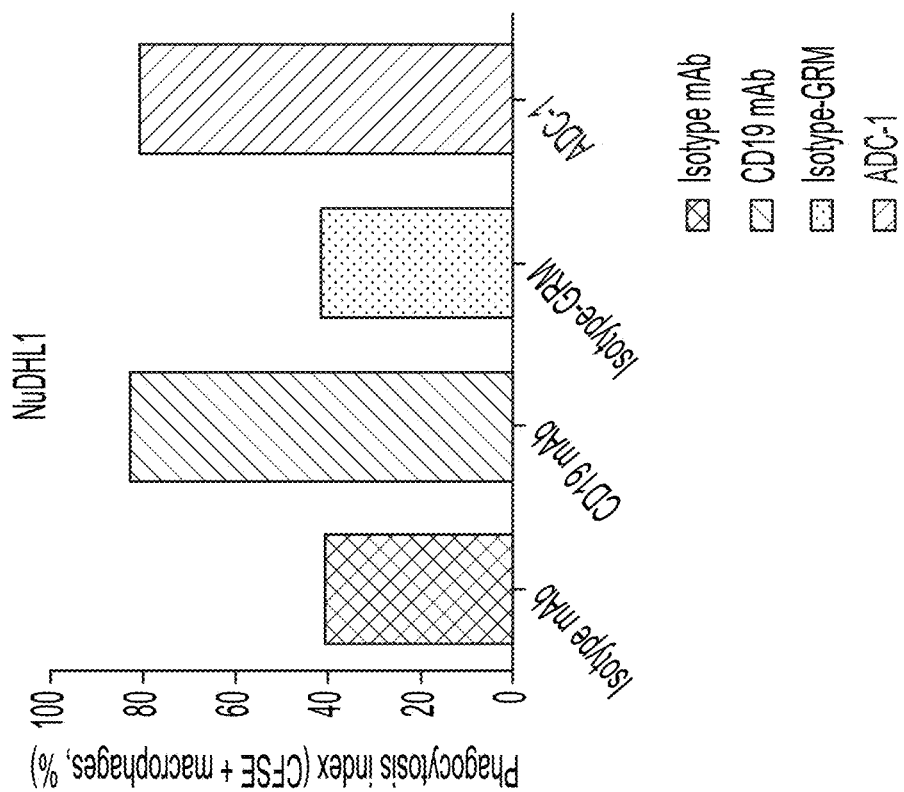

FIGS. 7A-7B: ADC-1 induces antibody-dependent cellular phagocytosis (ADCP) of B-cell malignancy cell lines in co-culture with monocyte-derived macrophages. A and B, CFSE-labeled NuDHL1 (A) and Raji (B) cells were treated with 200 nM of indicated agents and co-cultured with monocyte-derived macrophages for 3 hours. CD68+ is used as a marker for matured macrophages and the phagocytosis index represents the percentage of phagocytosed target cells (CFSE+CD68+) out of total matured macrophages (CD68+) gate.

Figures 8A, 8B:
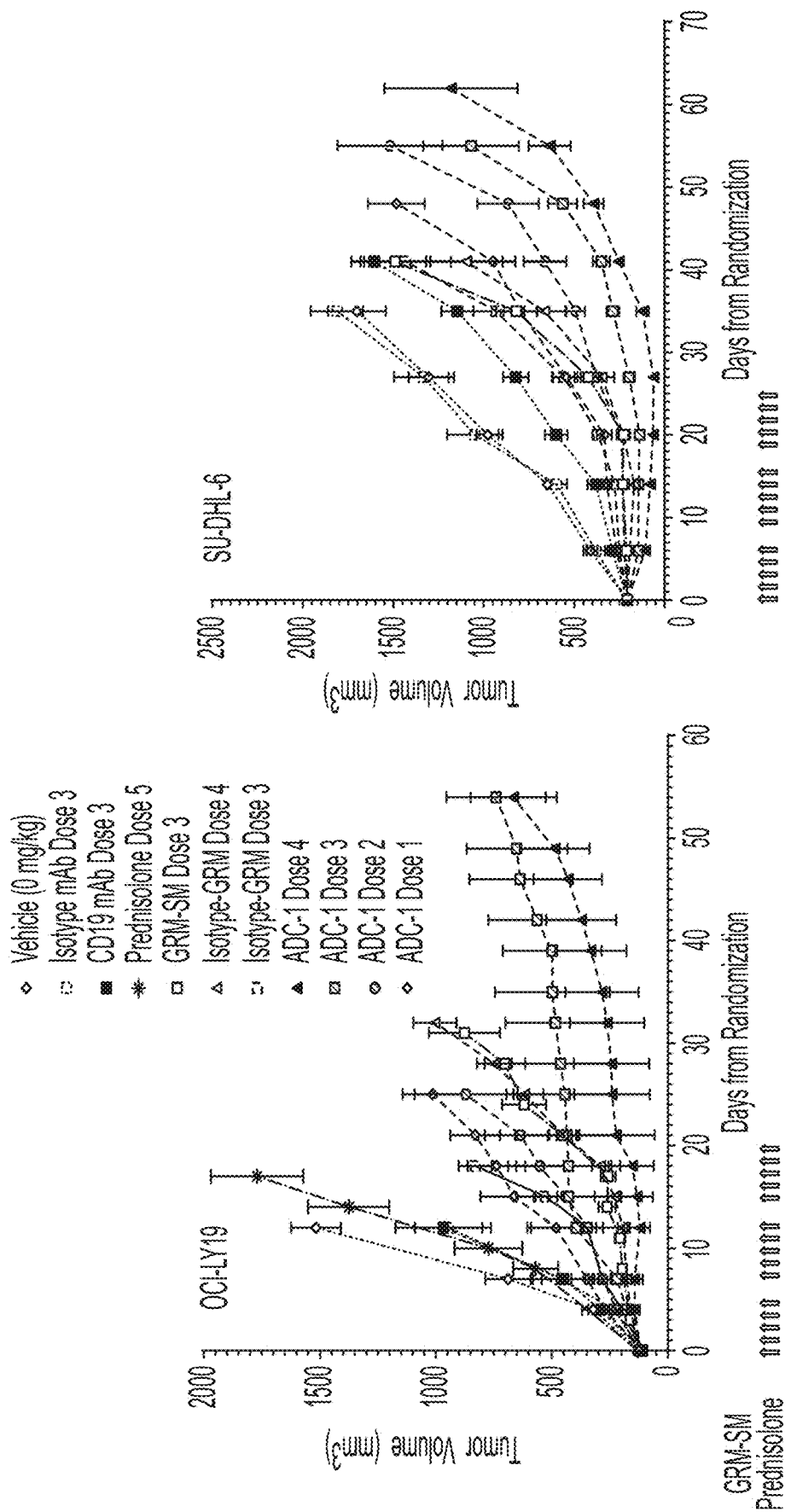

FIGS. 8A-8B: Growth inhibition of xenografted Diffuse Large B-Cell Lymphoma tumors (OCI-LY19 and SU-DHL-6) in immune-compromised mice by various doses of ADC-1. A and B, growth inhibition of xenografted OCI-LY19 tumors grown in CB17/SCID mice (A) and SU-DHL-6 (B) cells by intraperitoneal (IP) administration of ADC-1. The volume of subcutaneous tumors was plotted as a function of time after randomization and dosing. Growth inhibition was studied in mice with a subcutaneous tumor (average tumor volume 117-205 $mm^3$ of OCI-LY19 (A) and SU-DHL-6 tumors grown in SCID-beige mice (B) by administration of ADC-1, Isotype-GRM, huCD19 antibody, Isotype antibody as a single dose (QDx1) at various dose levels (doses 1-5, with dose 2 being 3 times the dose of dose 1, with dose 3 being 10 times the dose of dose 1, with dose 4 being 30 times the dose of dose 1, and with dose 5 being 50 times the dose of dose 1). GRM-SM was administered as multiple daily doses (QDx5)3. Each point on the curve represents the mean of seven (SU-DHL-6) or eight (OCI-LY19) tumors. Error bars depict the standard error of the mean.

Figure 9:
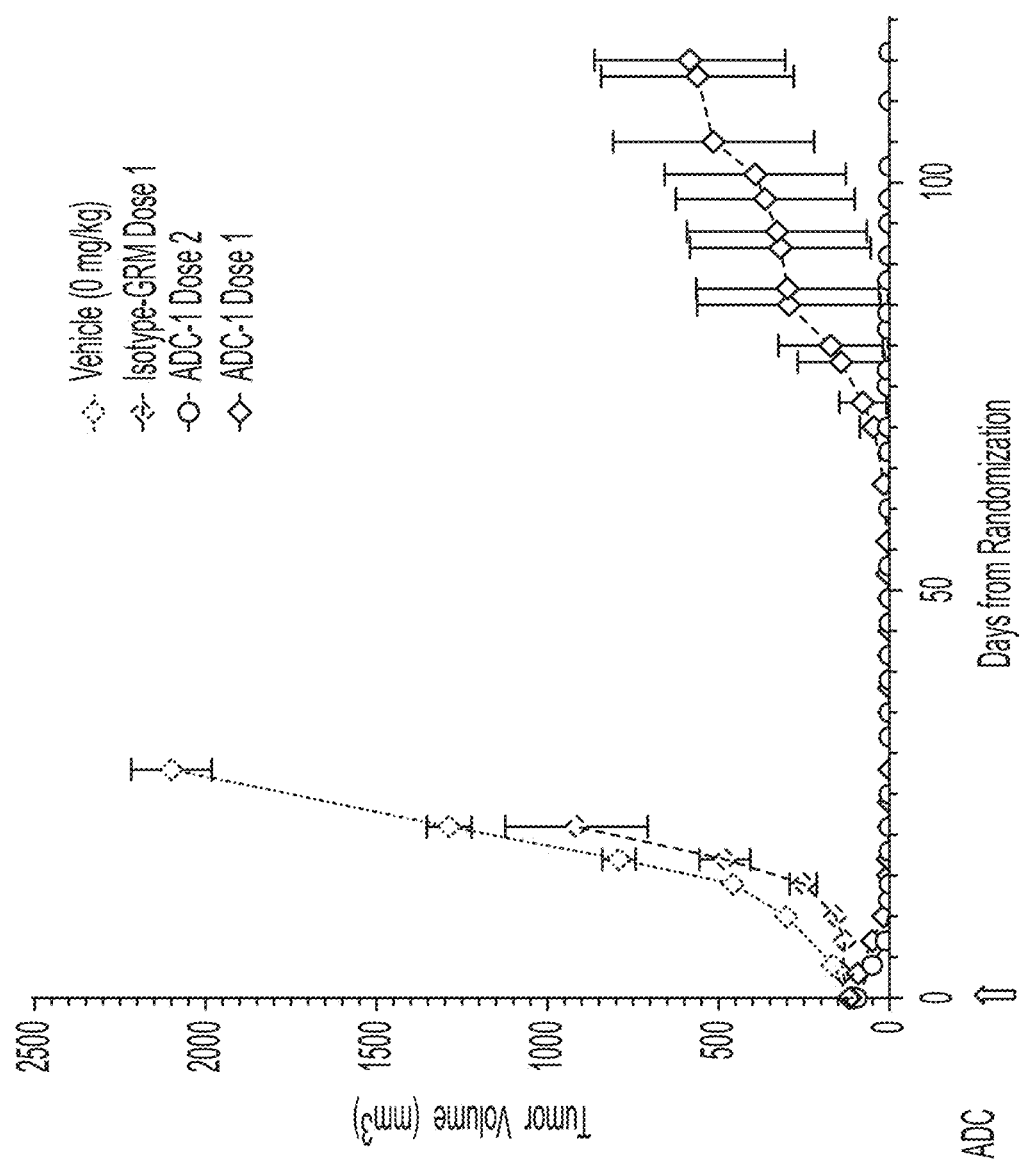

FIG. 9: Growth inhibition of xenografted Acute Lymphoblastic Leukemia (RS4; 11) by various doses of ADC-1. Growth inhibition of xenografted RS4; 11 tumors (immune-compromised CB17/SCID mice) by administration of ADC-1. The volume of subcutaneous tumors was plotted as a function of time after randomization and dosing. Growth inhibition was studied in mice with a subcutaneous tumor (average tumor volume 118 $mm^3$) of xenografted RS4; 11 cells by administration of ADC-1, Isotype-GRM, as a single dose (QD×1) at various doses (dose 1 and dose 2, with dose 2 being 2 times the dose of dose 1). Each point on the curve represents the mean of five tumors. Error bars depict the standard error of the mean.

Figure 10A:
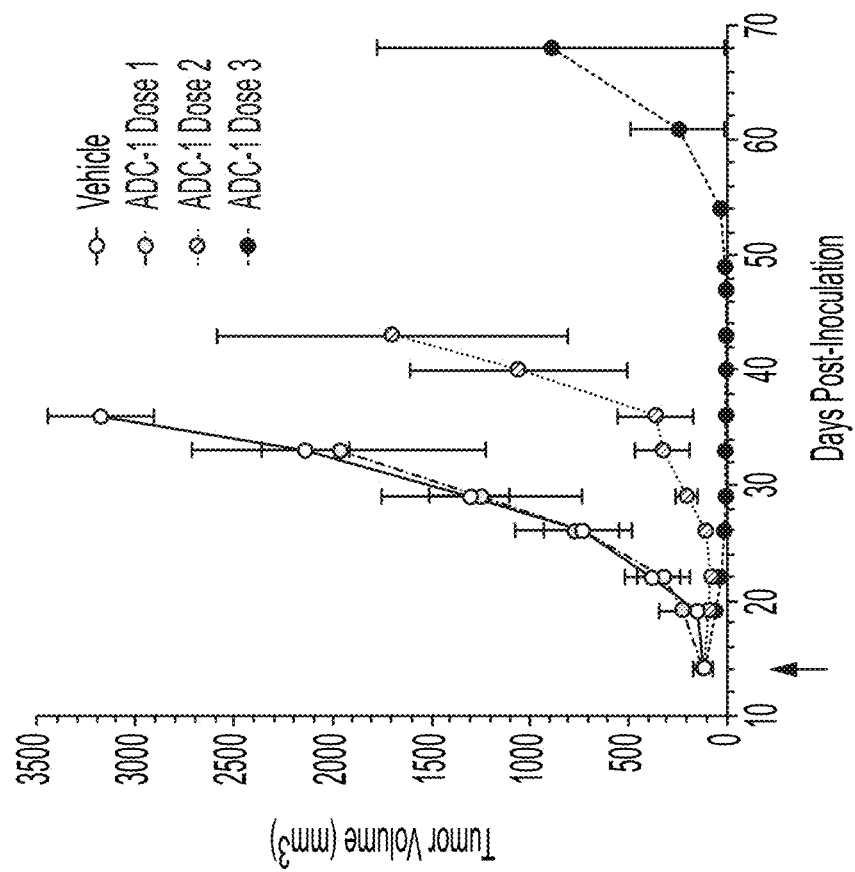
Figure 10B:
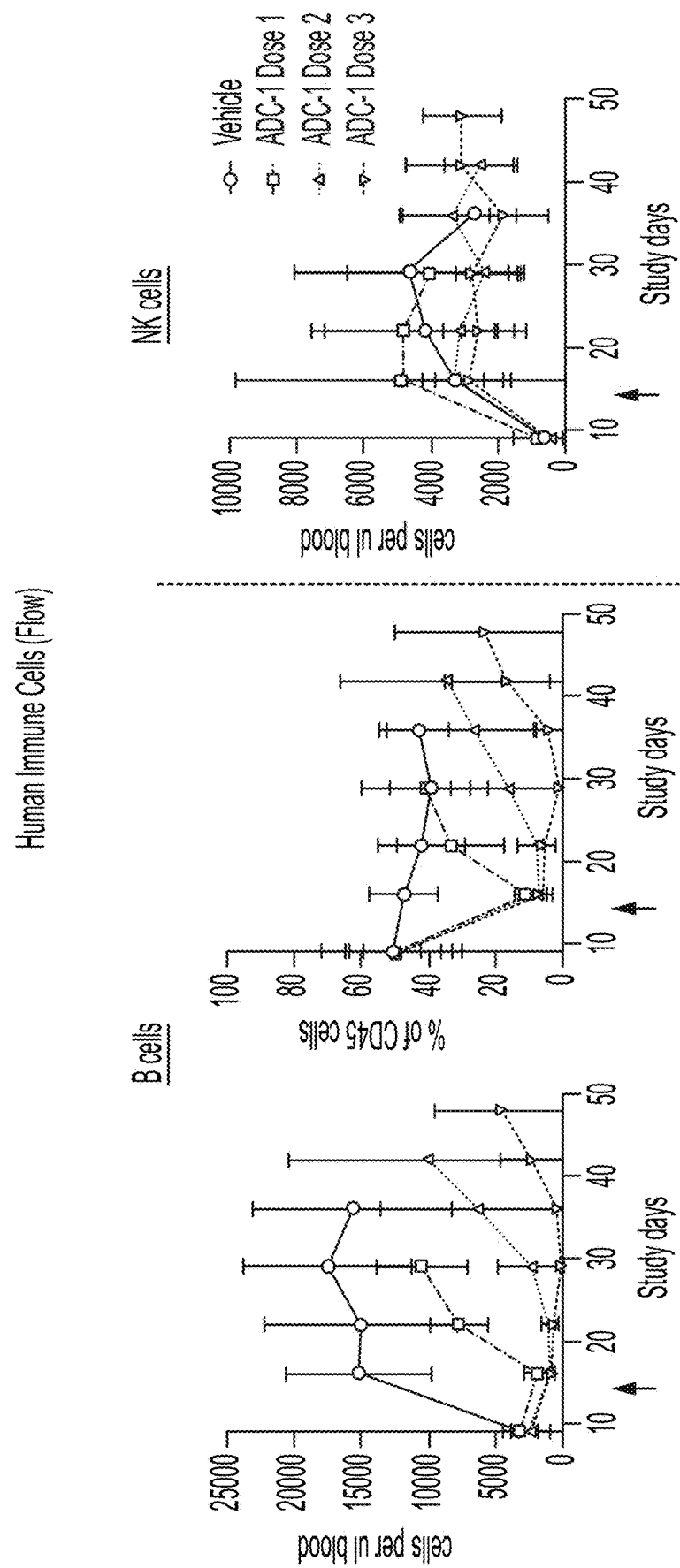

FIGS. 10A-10B: Growth inhibition of xenografted Diffuse Large B-cell Lymphoma cells (OCI-LY19) by various doses of ADC-1 in humanized immune-competent huCD 34+NSG huIL-15 mice. A, Growth inhibition of xenografted OCI-LY19 tumors by IP administration of isotype mAb, CD19 mAb, and ADC-1. ADC-1 was administered as a single dose (QDx1) at various dose levels (doses 1-3, with dose 2 being 3 times the dose of dose 1, and with dose 3 being 10 times the dose of dose 1. Each point on the curve represents the mean of four or five tumors. Error bars depict the standard error of the mean. B, Flow cytometry data of human B cells and human NK cells, from tail vein bleeds were obtained at indicated time points. Each point on the curve represents the mean of four or five animals. Error bars depict the standard deviation of the mean.

Figure 11:
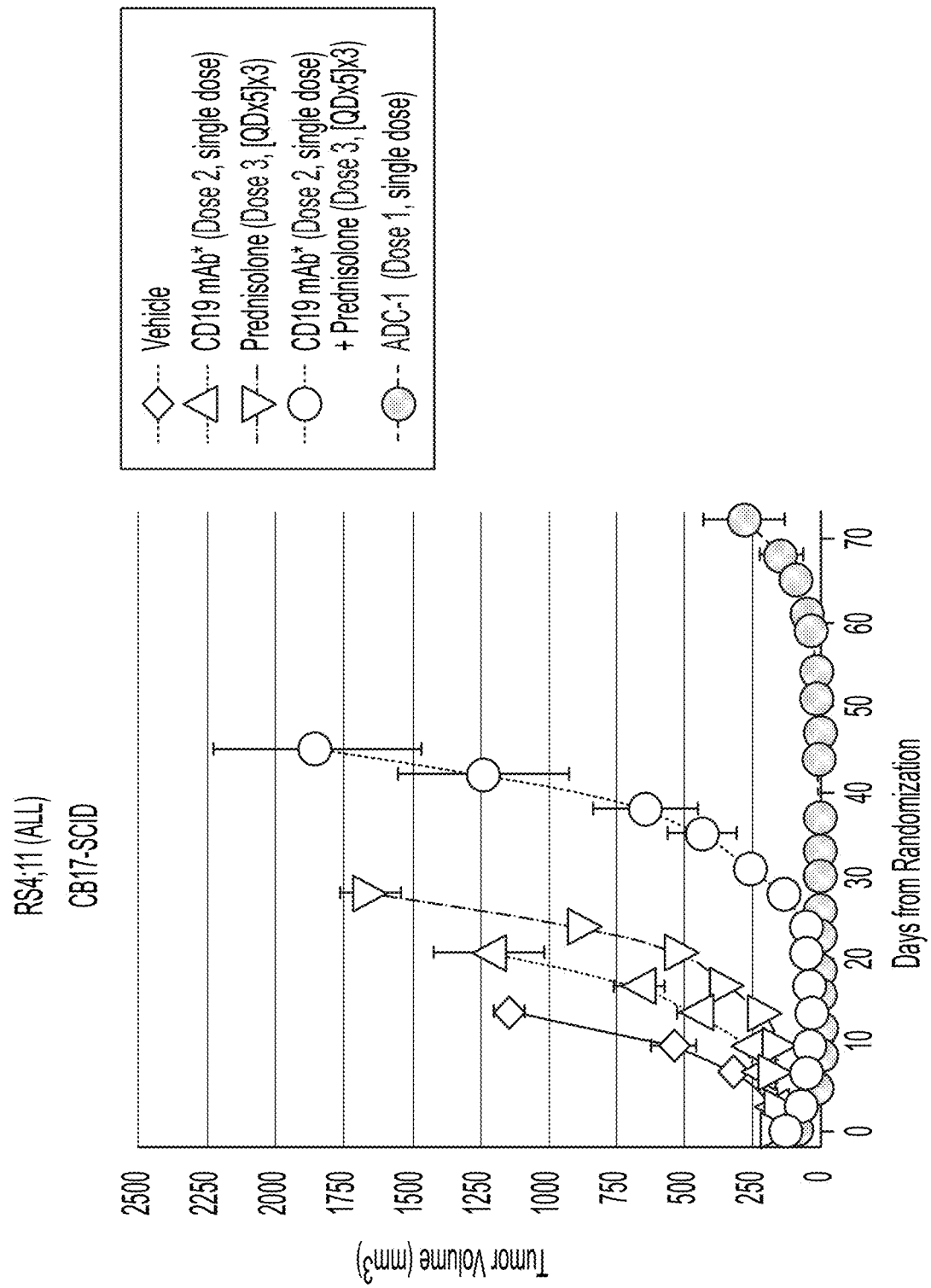

FIG. 11: ADC-1 induces superior anti-tumor activity compared to high-dose CD19 mAb, prednisolone alone, and CD19 mAb and prednisolone combination. Growth inhibition of xenografted RS4; 11 tumors in CB17/SCID mice by administration of indicated treatments. The volume of subcutaneous tumors was plotted as a function of time after randomization and dosing. Fucosylated mAb and ADC-1 were used in this study. Various dose levels were used (doses 1-3, with dose 2 being 10 times the dose of dose 1, and with dose 3 being 33⅓ times the dose of dose 1). Each point on the curve represents the mean of five tumors. Error bars depict the standard error of the mean.

Figure 12A:
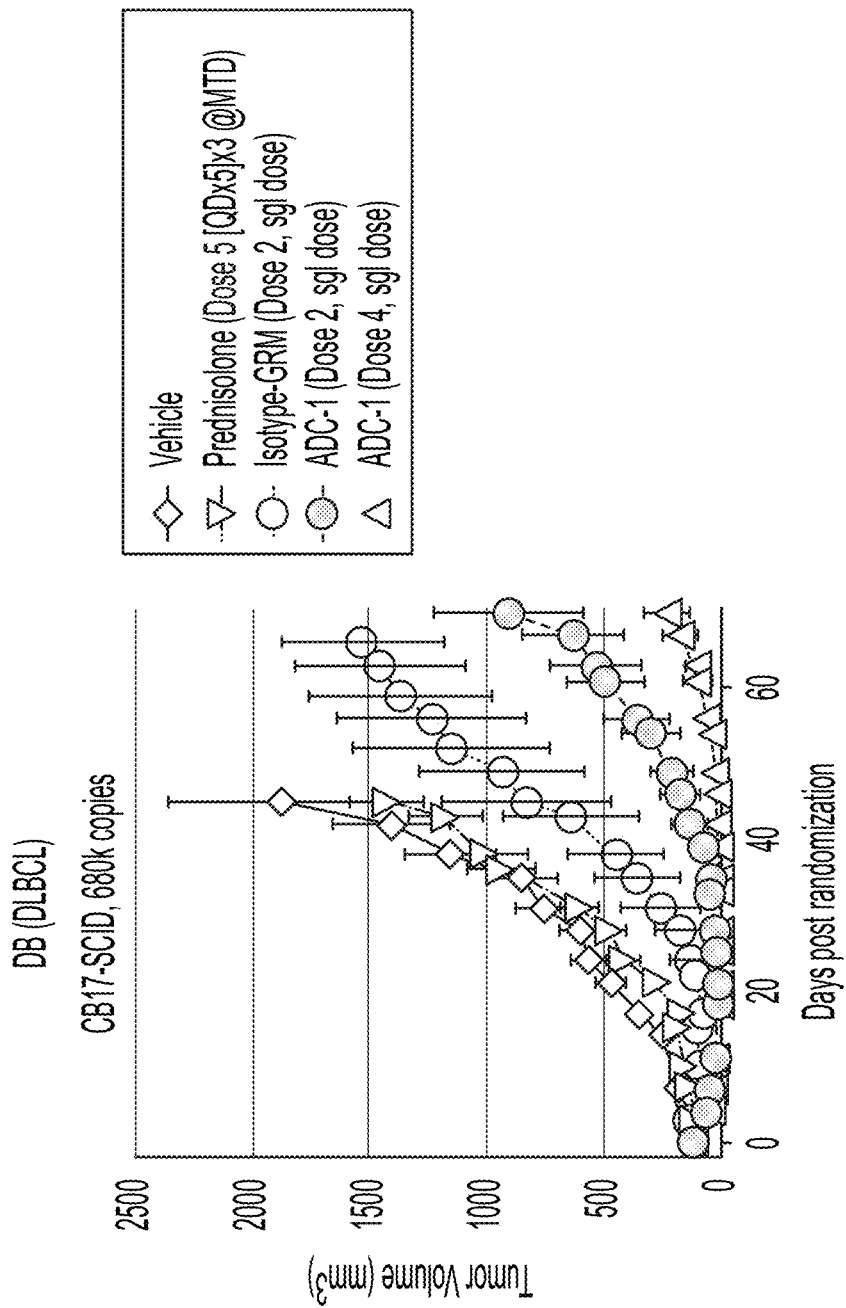
Figures 12B, 12C:
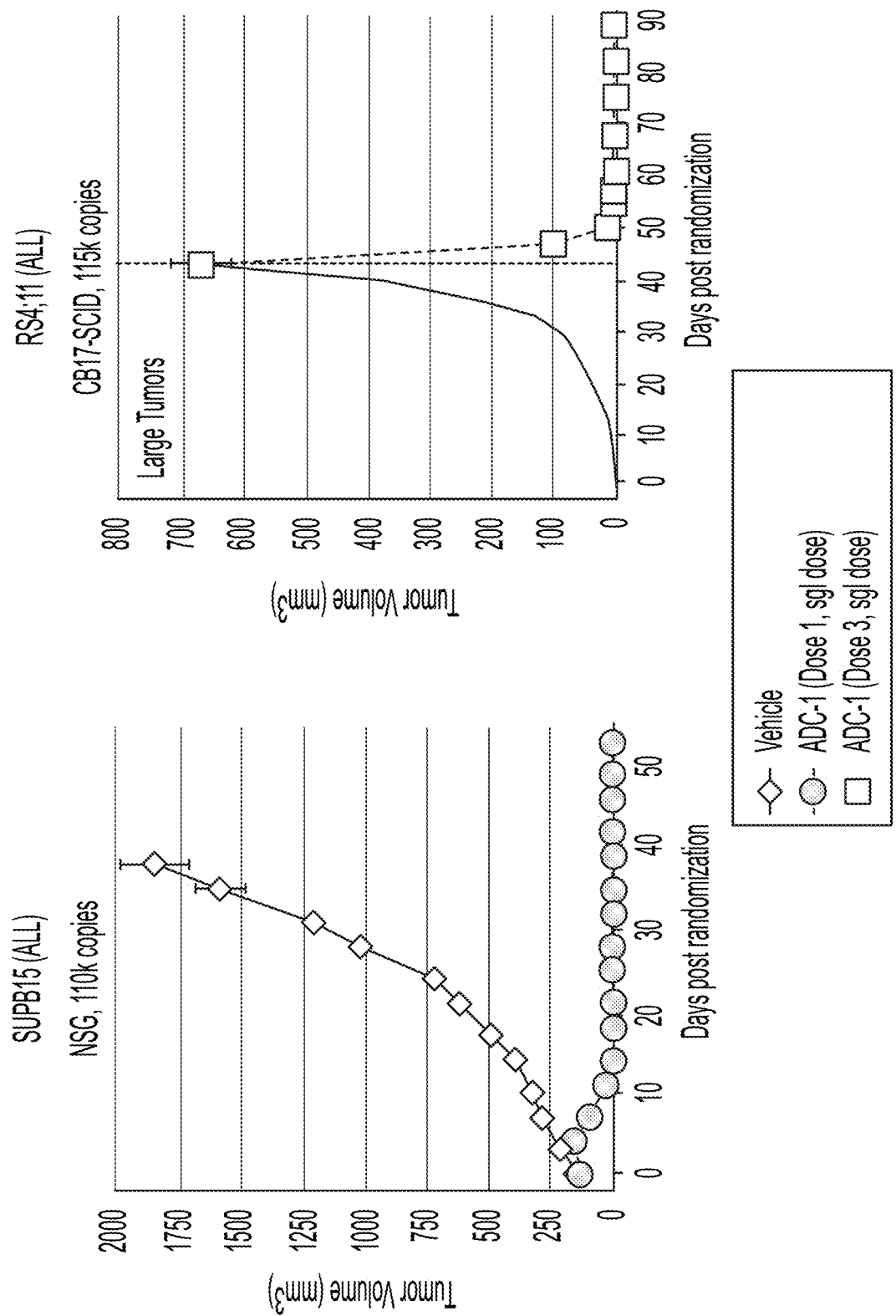

FIGS. 12A-12C: ADC-1 exhibits anti-tumor activity in multiple xenograft models of B-cell malignancies in vivo compared to prednisolone or isotype GRM control. A-C, DB (A), SUPB15 (B), and RS4; 11 (C) xenograft models were treated with indicated agents. Various doses were used (doses 1-5, with dose 2 being 3 ⅓ times the dose of dose 1, with dose 3 being 6 ⅔ times the dose of dose 1, with dose 4 being 10 times the dose of dose 1, and with dose 5 being 33 ⅓ times the dose of dose I). The mouse strain and CD 19 in vitro cell surface copy number for each xenograft tumor model are listed as shown.

Figures 13A, 13B:
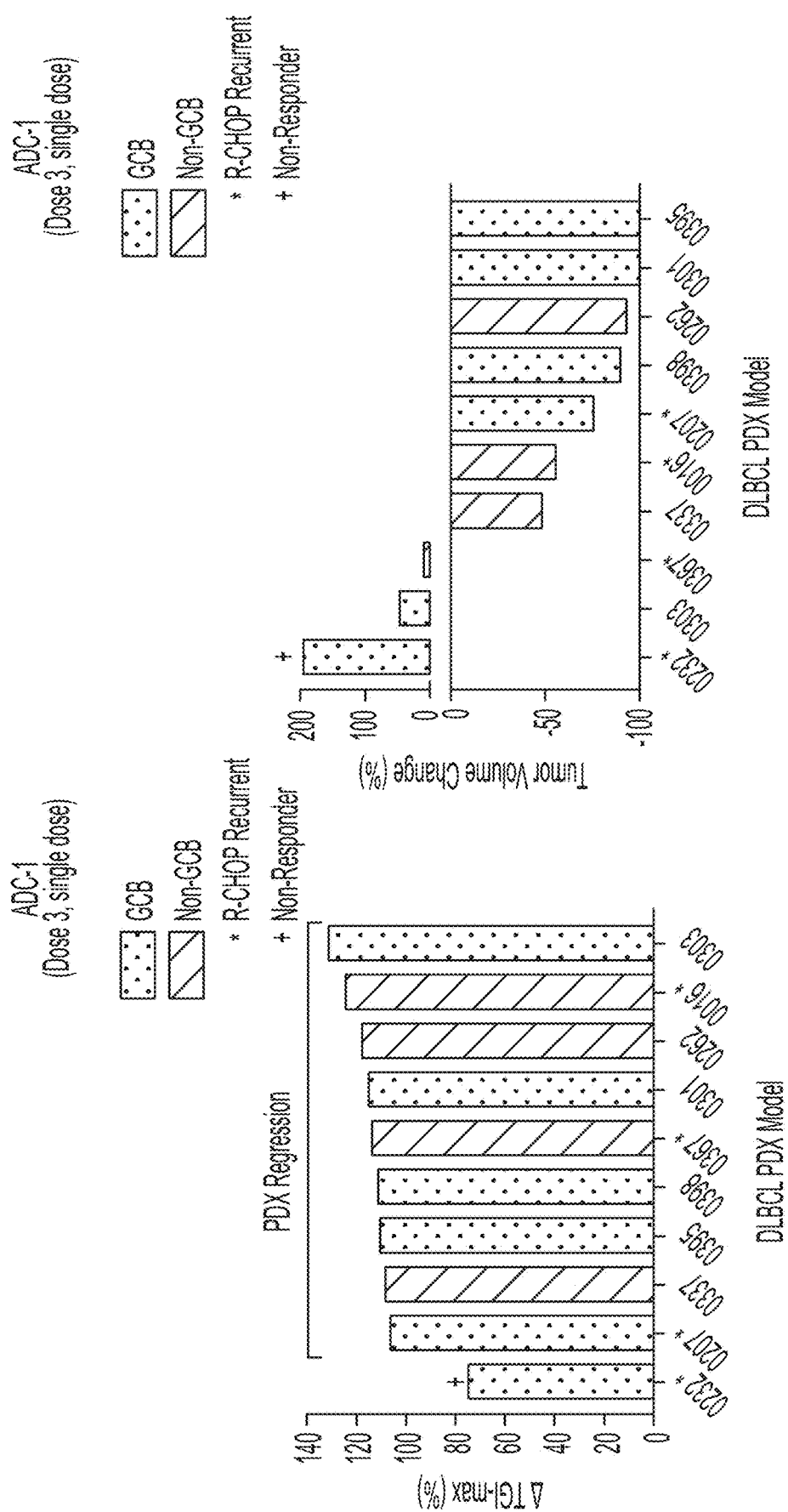

FIGS. 13A-13B: Anti-Tumor Efficacy Observed in 10 DLBCL patient derived xenograft (PDX) Models. PDX models derived from germinal center B-cell like (GCB) and non-GCB DLBCL patients were implanted into NOD-SCID mice, and randomized when tumors reached ~200 mm3. Mice were treated with ADC-I (dose 3, I.P) for a single dose and tumor growth was monitored relative to control treated PDXs. (A) Tumor growth inhibition shown as Delta % TGI max=1-(tumor volume of treated group on day X-tumor volume of treated group at randomization)/(tumor volume of control on day X-tumor volume of control at randomization)]*100. Determined when difference between treatment and control groups were maximal. Tumor regression (responder): >105% delta TGI max-yes/no response. (B) Tumor volume change (%) at time point when vehicle control tumors had reached 100 mm$^3$, as calculated by [(tumor volume at time point/tumor volume at randomization)–1]×100.

Figure 14A:
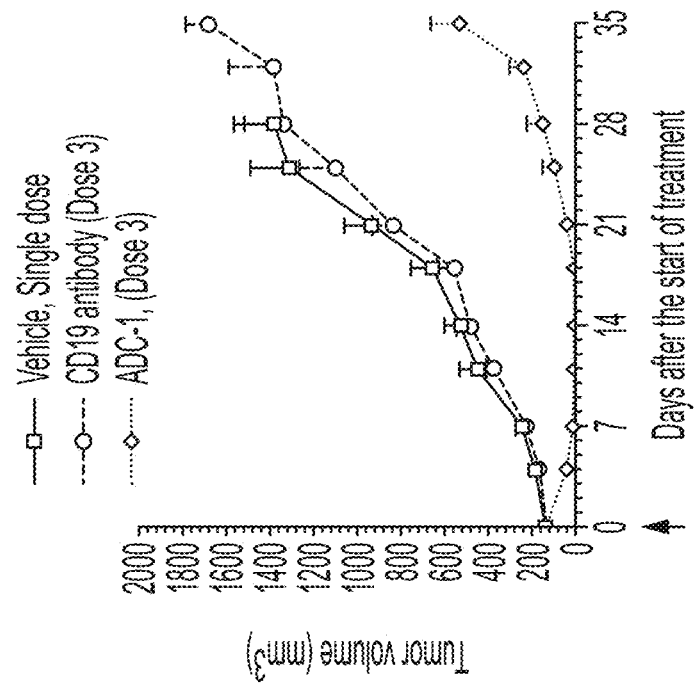
Figure 14B:
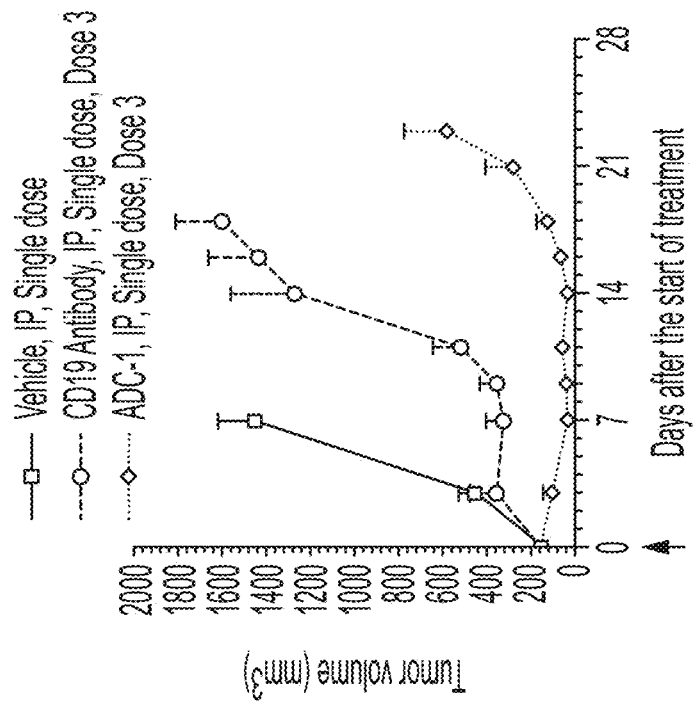

FIGS. 14A-14B: Anti-Tumor Efficacy Observed in R-CHOP Recurrent PDX Models. PDX models derived from DLBCL patients that were from R-CHOP recurrent patients (treated for 4 cycles) were implanted into NOD-SCID mice and randomized when tumors reached ~200 mm3. Mice were treated with ADC-1 or CD19 antibody at dose 3 (I.P) for a single dose and tumor growth was monitored relative to control treated PDXs. (A) PDX Model LY-24-0207, from 38 year old male with GCB DLBCL, R-CHOP treatment recurrent (4 cycles) and slight stasis with ibrutinib; and (B) PDX Model LY-24-0016 from 59 year old male, activated B-cell (ABC) DLBCL, R-CHOP treatment recurrent (4 cycles), resistant to ibrutinib.

Figure 15:
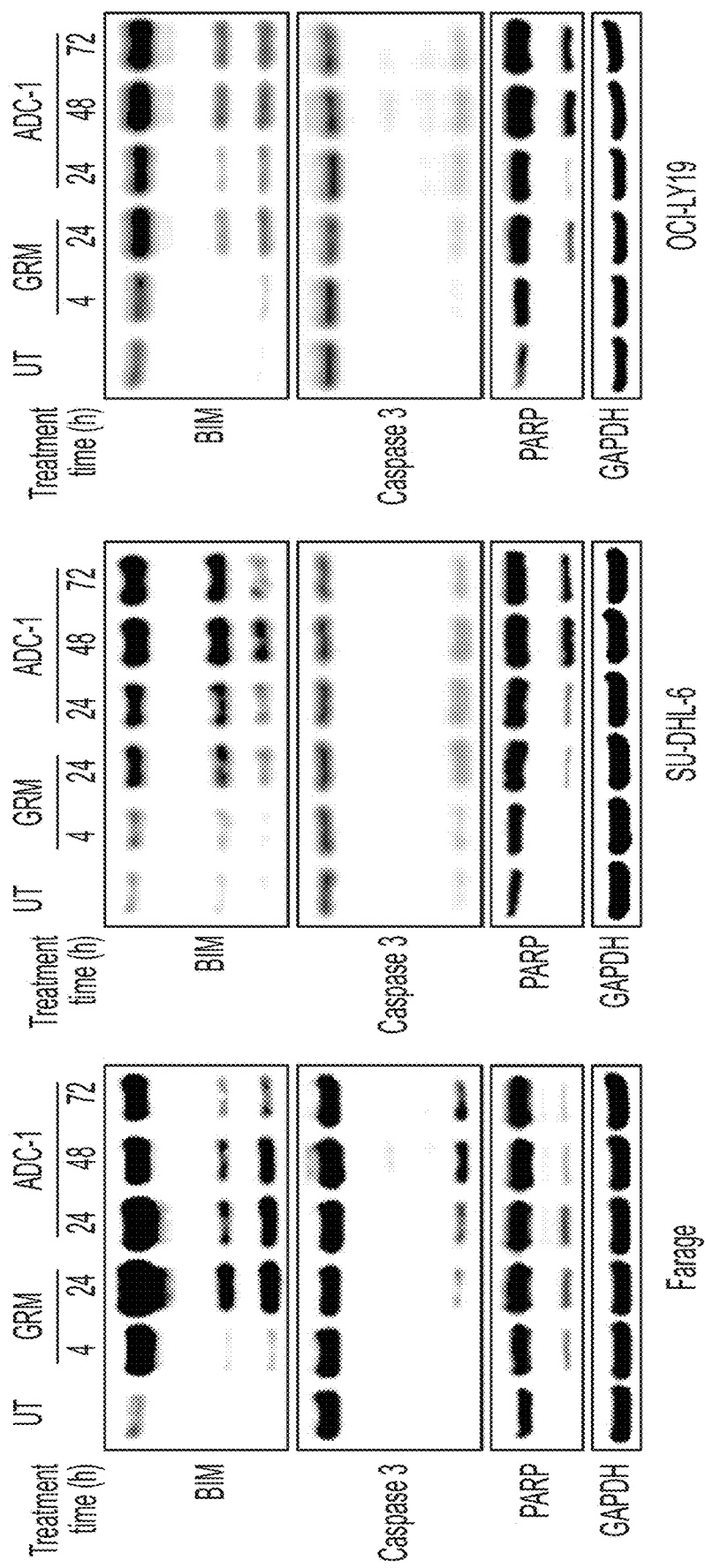

FIG. 15: GRM and ADC-1 induces apoptosis in DLBCL cell lines. Farage, SU-DHL-6, OCI-LY19 cells were treated with GRM or ADC-1 for indicated time before cell lysis. The lysates were resolved on SDS-PAGE and immunoblotted with antibodies against pro-apoptotic regulator BIM and markers of apoptotic induction (cleaved caspase-3, cleaved PARP). Arrow indicates apoptotic cleavage product. GAPDH was used as the loading control.

Figure 16:
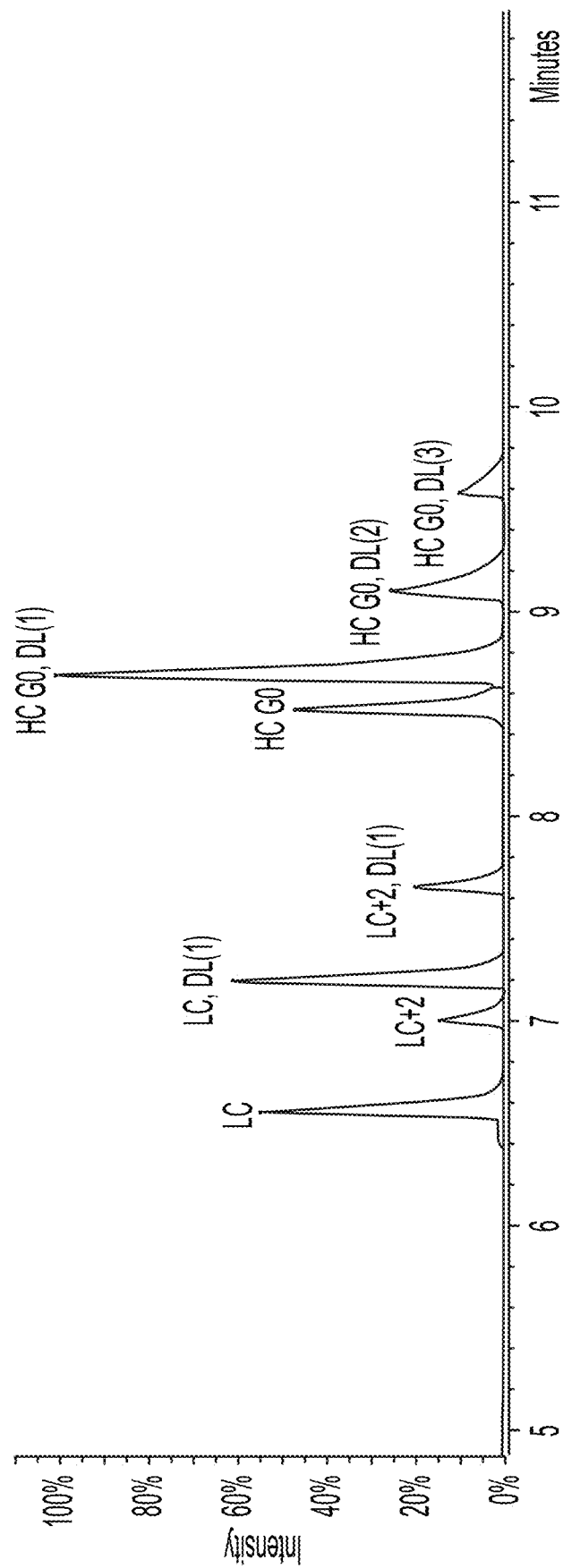

FIG. 16: ADC-1 Reduced LC-MS Total Ion (A280) Chromatogram. LC=Light Chain, LC+2=Light Chain+2 Free thiols, DL(X)=Drug Linker (number attached), HC G0=Heavy Chain with G0 glycan.

7. DETAILED DESCRIPTION

The present disclosure provides antibody drug conjugates (ADCs) comprising a glucocorticoid receptor modulator agonist linked to an anti-CD19 antibody.

7.1. CD19 Antibodies

CD19 represents an attractive immunotherapy target for cancers of B-cell origin due to its high expression levels on the majority of B-cell malignancies including DLCB, FL, CLL, and ALL). A humanized anti-CD19 antibody was developed that specifically binds CD19 expressed on the surface of B-cells and CD19 positive cancer cells, thereby inhibiting CD19 signaling. In an embodiment, the antibody is composed of two heavy and two light chain variable regions. On each variable region, there are three CDRs that allow the antibody to bind to CD19. On both variable chains, there are a total of six different CDRs. Additionally, the antibody contains a human heavy chain constant region comprising a human Fc of the immunoglobulin class G1 (IgG1). The anti-CD19 antibodies described herein can be fucosylated or afucosylated and demonstrate in vitro functionality, immunosafety, and drug-like properties.

In certain embodiments, an afucosylated antibody of the invention has higher affinity for certain FcγR receptors expressed on immune cells. As an example, afucosylated IgG1 antibodies have increased binding to FcγRIIIA expressed on NK cells which results in enhanced activity in purified natural killer cell or peripheral blood mononuclear cell (PBMC) ADCC assays compared to a fucosylated form of that antibody. The ADCC activity of anti-CD19 antibodies can be demonstrated using ADCC bioassay techniques known in the art. For example, the ADCC Reporter Bioassay in human FcγRIIIa V158 or F158 allelic variant reporter lines can be used (see Example 3).

In various embodiments, the antibodies comprise all or a portion of a constant region of an antibody. In some embodiments, the constant region is an isotype selected from: IgA (e.g., IgA1 or IgA2), IgD, IgE, IgG (e.g., IgG1, IgG2, IgG3 or IgG4), and IgM. In specific embodiments, the anti-CD19 antibodies described herein comprise an IgG1. As used herein, the "constant region" of an antibody includes the natural constant region, allotypes or variants.

The light constant region of an anti-CD19 antibody may be a kappa (κ) light region or a lambda (λ) region. A λ light region can be any one of the known subtypes, e.g., λ1, λ2, λ3, or λ4. In some embodiments, an anti-CD19 antibody comprises a kappa (κ) light region.

The term "monoclonal antibody" as used herein is not limited to antibodies produced through hybridoma technology. A monoclonal antibody is derived from a single clone, including any eukaryotic clone.

The term "chimeric" antibody as used herein refers to an antibody having variable sequences derived from a non-human immunoglobulin, such as a rat or a mouse antibody, and human immunoglobulin constant regions, typically chosen from a human immunoglobulin template.

"Humanized" forms of non-human (e.g., murine) antibodies comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody can also comprise at least a portion of an immunoglobulin constant region (Fc), typically that of a human immunoglobulin consensus sequence.

"Human antibodies" include antibodies having the amino acid sequence of a human immunoglobulin and include antibodies isolated from human immunoglobulin libraries or from animals transgenic for one or more human immunoglobulins and that do not express endogenous functional immunoglobulins. Human antibodies can be made by a variety of methods known in the art including phage display methods using antibody libraries derived from human immunoglobulin sequences.

Anti-CD19 antibodies of the disclosure include full-length (intact) antibody molecules.

The anti-CD19 antibodies may be antibodies whose sequences have been modified to alter at least one constant region-mediated biological effector function. For example, the anti-CD19 antibodies described herein include antibodies that have been modified to acquire or improve at least one constant region-mediated biological effector function relative to an unmodified antibody, e.g., to enhance FcγR interactions (See, e.g., US Patent Appl. No. 2006/0134709, U.S. Pat. No. 8,642,292 B2) or to enhance the antibody's ability to mediate ADCC. For example, an anti-CD19 antibody of the disclosure can have a constant region that binds FcγRI, FcγRIIA, FcγRIIB, FcγRIIIA and/or FcγRIIIB with greater affinity than the corresponding unmodified constant region. An anti-CD19 antibody of the disclosure can be one that has a modified Fc region and mediates an enhanced ADCC response, wherein the ADCC response is enhanced with respect to an antibody having the same variable regions (i.e., VH and VL) and a wild type IgG1 Fc region (i.e., wild type CL, CH1, CH2, and CH3). Anti-CD19 antibodies with high affinity for human CD19 may be desirable for therapeutic and diagnostic uses. Accordingly, the present disclosure contemplates antibodies having a high binding affinity to human CD19. In specific embodiments, the anti-CD19 antibodies binds to human CD19 with an affinity of about 15 nM, 10 nM, 7 nM, 6 nM, 5 nM, 4 nM, 3 nM, 2 nM, 1 nM, or 0.1 nM. In some embodiments, the antibodies bind human CD19 with an affinity in the range of about 0.1 nM to about 10 nM.

In some embodiments, the invention provides a monoclonal anti-CD19 antibody comprising two sets of six different complementarity-determining regions (CDRs), two sets of two different variable regions, two full heavy chains, and two full light chains.

In some embodiments, the antibody is a recombinant, afucosylated, humanized, IgG1 kappa monoclonal antibody that binds to human CD19.

In an embodiment, the antibody comprises six CDRs comprising the following sequences:

```
CDR-H1:
                             (SEQ ID NO: 1)
GFTFTTYWIN

CDR-H2:
                             (SEQ ID NO: 2)
NIYPSDSYTNYNQKFKD

CDR-H3:
                             (SEQ ID NO: 3)
EDYYGSSSYYAMDY

CDR-L1:
                             (SEQ ID NO: 4)
KASQDVGTAVA

CDR-L2:
                             (SEQ ID NO: 5)
WASTRHT

CDR-L3:
                             (SEQ ID NO: 6)
QQYSTYPLT
```

In some embodiments, the antibody of this disclosure comprises a CDR-H1 having the amino acid sequence shown as SEQ ID NO: 1, a CDR-H2 having the amino acid sequence shown as SEQ ID NO: 2; a CDR-H3 having the amino acid sequence shown as SEQ ID NO: 3, a CDR-L1 having the amino acid sequence shown as SEQ ID NO: 4, a CDR-L2 having the amino acid sequence shown as SEQ ID NO: 5; and a CDR-L3 having the amino acid sequence shown as SEQ ID NO: 6.

In some embodiments, the antibody of this disclosure comprises a heavy chain variable region comprising the amino acid sequence shown as SEQ ID NO: 7: EVQLVES-GGGLVQPGGSLRLSCAASGFTFTTY-WINWVRQAPGKGLEWIGNIYPSDSYTN YNQKFKDRATLSVDKSKNTAYLQMNSLRAED-TAVYYCTREDYYGSSSYYAMDYWGQ GTLVTVSS (SEQ ID NO: 7); and a light chain variable region comprising the amino acid sequence shown as SEQ ID NO: 8:

```
                                       (SEQ ID NO: 8)
AILMTQSPSSLSASVGDRVTITCKASQDVGTAVAWYQQKPGKAPKLLIY
WASTRHTGVPSRFSGSGSGTDFTLTISSLQPEDFATYYCQQYSTYPLTF
GQGTKVEIK.
```

In some embodiments, the antibody of this disclosure comprises a heavy chain comprising the amino acid sequence shown as SEQ ID NO: 9 or consisting of the amino acid sequence shown as SEQ ID NO: 9 (constant regions are normal text; the variable heavy domain is underlined; CDRs are *underlined bold italic* (disclosed as SEQ ID NOS: 1-3, respectively, in order of appearance) N-link glycoslation site is denoted by a subscript "g"):

```
EVQLVESGGGLVQPGGSLRLSCAAS GFTFTTYWIN WVRQAPGKGLEWIG

NIYPSDSYTNYNQKFKD RATLSVDKSKNTAYLQMNSLRAEDTAVYYCTR

EDYYGSSSYYAMDY WGQGTLVTVSSASTKGPSVFPLAPSSKSTSGGTAA

LGCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGPS

VFLFPPKPKDTLMISRTPEVTCVVVDVSHEDPEVKFNWYVDGVEVHNAK

TKPREEQYN_gSTYRVVSVLTVLHQDWLNGKEYKCKVSNKALPAPIEKTI

SKAKGQPREPQVYTLPPSREEMTKNQVSLTCLVKGFYPSDIAVEWESNG

QPENNYKTTPPVLDSDGSFFLYSKLTVDKSRWQQGNVFSCSVMHEALHN

HYTQKSLSLSPGK
```

(full-length sequence disclosed as SEQ ID NO: 9); and a light chain comprising the amino acid sequence shown as SEQ ID NO: 10 or consisting of the amino acid sequence shown as SEQ ID NO: 10 (constant regions are normal text; the variable light domain is underlined; CDRs are *underlined bold italic* (CDR sequences disclosed as SEQ ID NOS: 4-6, respectively, in order of appearance):

```
AILMTQSPSSLSASVGDRVTITC KASQDVGTAVA WYQQKPGKAPKLLIY

WASTRHT GVPSRFSGSGSGTDFTLTISSLQPEDFATYYC QQYSTYPLTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC (full-length sequence disclosed as SEQ ID NO: 10).
```

In an embodiment, the antibody of the disclosure comprises or consists of a light chain according to SEQ ID NO: 10, and a heavy chain according to SEQ ID NO: 11, which is the amino acid sequence of SEQ ID NO: 9 with the C-terminal lysine truncated:

EVQLVESGGGLVQPGGSLRLSCAAS*GFTFTTYWIN*WVRQAPGKGLEWIG

*NIYPSDSYTNYNQKFKD*RATLSVDKSKNTAYLQMNSLRAEDTAVYYCTR

*EDYYGSSSYYAMDY*WGQGTLVTVSSASTKGPSVFPLAPSSKSTSGGTAA

LGCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGPS

VFLFPPKPKDTLMISRTPEVTCVVVDVSHEDPEVKFNWYVDGVEVHNAK

TKPREEQYN$_g$STYRVVSVLTVLHQDWLNGKEYKCKVSNKALPAPIEKTI

SKAKGQPREPQVYTLPPSREEMTKNQVSLTCLVKGFYPSDIAVEWESNG

QPENNYKTTPPVLDSDGSFFLYSKLTVDKSRWQQGNVFSCSVMHEALHN

HYTQKSLSLSPG (terminal lysine truncated sequence disclosed as SEQ ID NO: 11).

In an embodiment, the antibody is CD19 mAb, which has a heavy chain amino acid sequence set forth in SEQ ID NO: 9 or SEQ ID NO: 11, and a light chain amino acid sequence according to SEQ ID NO: 10.

In one embodiment, the heavy chain of the antibody of this disclosure is encoded by the following nucleotide sequence (full-length sequence disclosed as SEQ ID NO: 12):

*ATGGAGTTTGGGCTGAGCTGGCTTTTTCTTGTCGCGATTTTAAAAGGAG*

*TCCAGTGCGAGGTGCAGCTGGTTGAATCTGGCGGAGGACTGGTTCAGCC*

*TGGCGGATCTCTGAGACTGTCTTGTGCCGCCAGCG*GCTTCACCTTCACC

ACCTACTGGATCAACTGGGTCCGACAGGCCCCTGGCAAAGGCCTGGAAT

GGATCGGCAACATCTACCCCAGCGACAGCTACACCAACTACAACCAGAA

GTTCAAGGACCGGGCCACACTGAGCGTGGACAAGAGCAAGAATACCGCC

TACCTGCAGATGAACAGCCTGAGAGCCGAGGACACCGCCGTGTACTACT

GCACCAGAGAGGACTACTACGGCAGCAGCAGCTACTACGCCATGGACTA

TTGGGGCCAGGGCACCCTGGTTACCGTTAGCTCA*GCCTCCACCAAGGGC*

*CCATCGGTCTTCCCCCTGGCACCCTCCTCCAAGAGCACCTCTGGGGGCA*

*CAGCGGCCCTGGGCTGCCTGGTCAAGGACTACTTCCCCGAACCGGTGAC*

*GGTGTCGTGGAACTCAGGCGCCCTGACCAGCGGCGTGCACACCTTCCCG*

*GCTGTCCTACAGTCCTCAGGACTCTACTCCCTCAGCAGCGTGGTGACCG*

*TGCCCTCCAGCAGCTTGGGCACCCAGACCTACATCTGCAACGTGAATCA*

*CAAGCCCAGCAACACCAAGGTGGACAAGAAAGTTGAGCCCAAATCTTGT*

*GACAAAACTCACACATGCCCACCGTGCCCAGCACCTGAACTCCTGGGGG*

*GACCGTCAGTCTTCCTCTTCCCCCCAAAACCCAAGGACACCCTCATGAT*

*CTCCCGGACCCCTGAGGTCACATGCGTGGTGGTGGACGTGAGCCACGAA*

*GACCCTGAGGTCAAGTTCAACTGGTACGTGGACGGCGTGGAGGTGCATA*

*ATGCCAAGACAAAGCCGCGGGAGGAGCAGTACAACAGCACGTACCGTGT*

*GGTCAGCGTCCTCACCGTCCTGCACCAGGACTGGCTGAATGGCAAGGAG*

*TACAAGTGCAAGGTCTCCAACAAAGCCCTCCCAGCCCCCATCGAGAAAA*

*CCATCTCCAAAGCCAAAGGGCAGCCCCGAGAACCACAGGTGTACACCCT*

*GCCCCCATCCCGGGAGGAGATGACCAAGAACCAGGTCAGCCTGACCTGC*

CTGGTCAAAGGCTTCTATCCCAGCGACATCGCCGTGGAGTGGGAGAGCA

ATGGGCAGCCGGAGAACAACTACAAGACCACGCCTCCCGTGCTGGACTC

CGACGGCTCCTTCTTCCTCTACAGCAAGCTCACCGTGGACAAGAGCAGG

TGGCAGCAGGGGAACGTCTTCTCATGCTCCGTGATGCATGAGGCTCTGC

ACAACCACTACACGCAGAAGAGCCTCTCCCTGTCTCCGGGTAAATGA

Secretion signal peptide in italics; includes final stop codon (TGA); constant region is bold; CDRs are underlined.

In one embodiment, the light chain of the antibody of this disclosure is encoded by the following nucleotide sequence (full-length sequence disclosed as SEQ ID NO: 13):

*ATGGACATGCGCGTGCCCGCCCAGCTGCTGGGCCTGCTGCTGCTGTGGT*

*TCCCCGGCTCGCGATGCGCCATCCTGATGACACAGAGCCCTTCTAGCCT*

*GAGCGCCAGCGTGGGAGACAGAGTGACCATCACCTGT*AAAGCCAGCCAG

GATGTGGGAACAGCCGTGGCCTGGTATCAGCAGAAGCCTGGAAAGGCCC

CTAAGCTGCTGATCTACTGGGCCAGCACAAGACACACAGGCGTGCCCAG

CAGATTTTCTGGCAGCGGCTCTGGCACCGACTTCACCCTGACCATATCT

AGCCTGCAGCCTGAGGACTTCGCCACCTACTACTGCCAGCAGTACAGCA

CATACCCTCTGACCTTTGGCCAGGGCACCAAGGTGGAAATCAAA*CGAAC*

*TGTGGCTGCACCATCTGTCTTCATCTTCCCGCCATCTGATGAGCAGTTG*

*AAATCTGGAACTGCCTCTGTTGTGTGCCTGCTGAATAACTTCTATCCCA*

*GAGAGGCCAAAGTACAGTGGAAGGTGGATAACGCCCTCCAATCGGGTAA*

*CTCCCAGGAGAGTGTCACAGAGCAGGACAGCAAGGACAGCACCTACAGC*

*CTCAGCAGCACCCTGACGCTGAGCAAAGCAGACTACGAGAAACACAAAG*

*TCTACGCCTGCGAAGTCACCCATCAGGGCCTGAGCTCGCCCGTCACAAA*

*GAGCTTCAACAGGGGAGAGTGT*TAG

Secretion signal peptide in italics; includes final stop codon (TGA); constant region is bold; CDRs are underlined.

In some embodiments, the antibody comprises a human heavy chain constant region comprising human CH1, human hinge, human CH2, and human CH3 domain. In some embodiments, the encoded heavy chain constant region comprises an Fc portion, wherein the Fc portion is a human IgG1, IgG2, IgG3, IgG4, or IgM isotype. In an embodiment, the Fc is an IgG1, and the allotype is z non a. In an embodiment, the light chain is a kappa light chain.

In some embodiments, the antibody comprises an IgG IF c constant region that is afucosylated. Afucosylation may be carried out by techniques known in the art. See, e.g., Mol Cancer Ther (2020) 19 (5): 1102-1109) and PNAS (2013) 110(14) 5404-5409. For example, production of antibodies in cell lines defective in GDP-fucose formation due to, for example, a deficiency in GDP-mannose 4,6-dehydratase; production of antibodies in cells that have decreased levels of fucosyltransferase; production of antibodies in cells that have decreased levels of GD P-fucose transporter; production of antibodies in cells that overexpress β-1, 4-mannosyl-glycoprotein 4-β-N-acetylglucosaminyltransferase (GnT-III); or production of antibodies in cells that express a bacterial GDP-6-deoxy-D-lyxo-4-hexulose reductase (RMD). In an embodiment, the cells used to produce the afucosylated anti-CD19 antibodies of the invention are CHO cells engineered to express *Pseudomonas* RMD. The degree of afucosylation of antibodies can be determined through techniques known in the art. Typically, the antibody is 70% or more, 80% or more, 90% or more, or about 99%, or about 100% afucosylated. Preferably, the degree of afucosylation is equal to or greater than 90%. In some embodiments, the antibody is 70% or more, 80% or more, 90% or more, or about 100% afucosylated at position ASN-303 of SEQ ID NO: 9 or SEQ ID NO: 11 (EU: ASN-297). Afucosylation can be determined via hydrophilic interaction chromatography (HILIC) assay techniques, in which the degree of afucosylation is determined by polarity-dependent separation of the fragmented antibodies.

In an embodiment, the total afucosylated glycan species is determined by analysis of released N-linked glycans by HILIC with fluorescent detection. The glycans are released using peptide N-glycosidase F (PNGaseF) and subsequently labeled with a fluorescent tag. Fluorescently labeled N-linked glycans are analyzed by HILIC with fluorescence detection. The percent afucosylated glycan species is determined based on the sum of the peak areas of all afucosylated glycan peaks relative to the total peak area of all glycan peaks in the chromatogram. All peaks with a relative abundance of 0.5% or greater are included in the determination of percent afucosylated glycan species.

The present disclosure encompasses polynucleotide molecules encoding immunoglobulin light and heavy chain genes for anti-CD19 antibodies, vectors comprising such polynucleotides, and host cells capable of producing the anti-CD19 antibodies of the disclosure.

An anti-CD19 antibody of the disclosure can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, optionally, secreted into the medium in which the host cells are cultured, from which medium the antibodies can be recovered.

To generate polynucleotides encoding such anti-CD19 antibodies, DNA fragments encoding the light and heavy chain variable regions are first obtained. These DNAs can be obtained by amplification and modification of germline DNA or cDNA encoding light and heavy chain variable sequences, for example using the polymerase chain reaction (PCR).

Once DNA fragments encoding anti-CD19 antibody-related VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked," as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2, CH3 and, optionally, CH4). The sequences of human heavy chain constant region genes are known in the art (See, e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but in certain embodiments is an IgG1 or IgG4. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (See, e.g., Kabat, et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but in certain embodiments is a kappa constant region.

To express the anti-CD19 antibodies of the disclosure, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector.

The antibody genes are inserted into the expression vector by standard methods (e.g., ligation of complementary restriction sites on the antibody gene fragment and vector, or blunt end ligation if no restriction sites are present). Prior to insertion of the anti-CD19 antibody-related light or heavy chain sequences, the expression vector can already carry antibody constant region sequences. For example, one approach to converting the anti-CD19 monoclonal antibody-related VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the disclosure carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes.

In addition to the antibody chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced. For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a eukaryotic host cell, e.g., electroporation, lipofection, calcium-phosphate precipitation, DEAE—dextran transfection and the like.

In certain embodiments, expression of antibodies is performed in eukaryotic cells, e.g., mammalian host cells, of optimal secretion of a properly folded and immunologically active antibody. Exemplary mammalian host cells for expressing the recombinant antibodies of the disclosure include Chinese Hamster Ovary (CHO cells) (including DHFR—CHO cells, described in Urlaub and Chasin, 1980, Proc. Natl. Acad. Sci. USA 77:4216-4220, used with a DHFR selectable marker, e.g., as described in Kaufman and Sharp, 1982, Mol. Biol. 159:601-621), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Host cells can also be used to produce portions of intact antibodies, such as Fab fragments or scFv molecules. It is understood that variations on the above procedure are within the scope of the present disclosure. For example, it can be desirable to transfect a host cell with DNA encoding either the light chain or the heavy chain (but not both) of an anti-CD19 antibody of this disclosure.

Recombinant DNA technology can also be used to remove some or all of the DNA encoding either or both of the light and heavy chains that is not necessary for binding to human CD19. The molecules expressed from such truncated DNA molecules are also encompassed by the antibodies of the disclosure.

For recombinant expression of an anti-CD19 antibody of the disclosure, the host cell can be co-transfected with two expression vectors of the disclosure, the first vector encoding a heavy chain derived polypeptide and the second vector encoding a light chain derived polypeptide. The two vectors can contain identical selectable markers, or they can each contain a separate selectable marker. Alternatively, a single vector can be used which encodes both heavy and light chain polypeptides.

7.2. Anti-CD19 Antibodies Linked To A Glucocorticoid Receptor Modulator

Antibody drug conjugates (ADCs) comprising a glucocorticoid receptor modulator (GRM) agonist linked to an anti-CD19 antibody are provided herein.

In certain embodiments, antibody drug conjugates are provided comprising: (a) an anti-CD19 antibody; and (b) a radical of a glucocorticoid receptor modulator of Formula (I):

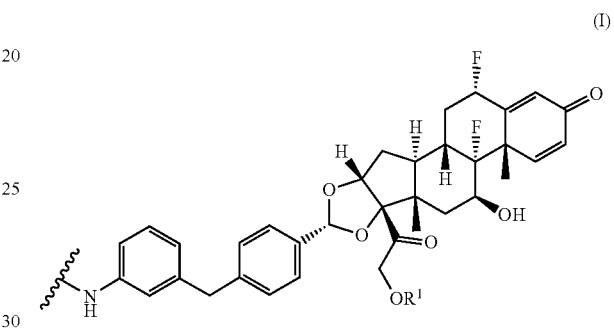

wherein:
$R^1$ is hydrogen or —P(=O)(OH)$_2$; and
further wherein the antibody is conjugated to the glucocorticoid receptor modulator by a linker of formula:

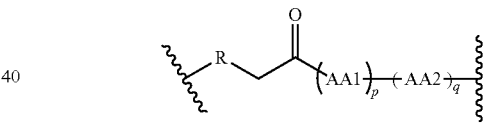

wherein R is the point of attachment of the antibody to the linker via a cysteine residue of the antibody providing an —S— group when linked. AA1 and AA2 are Alanine (Ala), and p and q are 1.

In certain embodiments, provided are antibody drug conjugates of Formula (II):

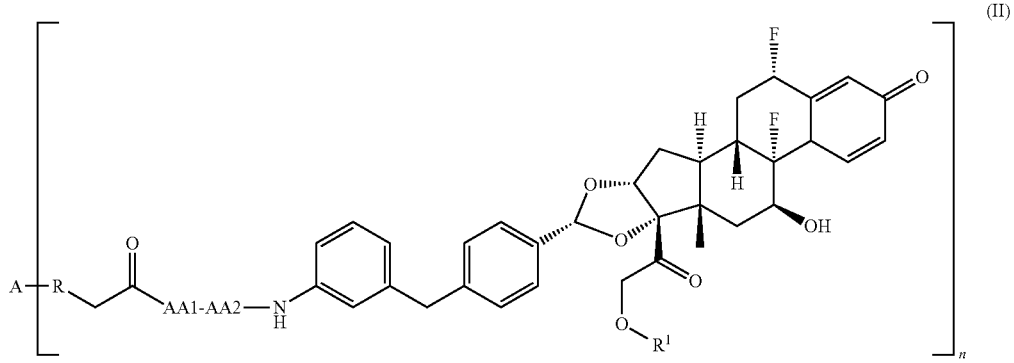

wherein:

A is an anti-CD19 antibody, R is the point of attachment of the antibody to the linker via a cysteine residue of the antibody providing an —S— group when linked, AA1 and AA2 are Alanine (Ala), $R^1$ is hydrogen or —P(=O)(OH)$_2$, and n is from 2 to 10. In embodiments, n is 1, 2, 3, 4, 5, 6, 7, 8, 9, or 10. In embodiments, n is 2, 3, 4, 5, 6, 7, or 8. In another embodiment, n is 1, 2, 3, 4, or 5. In another embodiment, n is 2, 3, 4, or 5. In an embodiment, n is 2, 4, 6, or 8. In another embodiment, n is 2, 4 or 6. In another embodiment, n is 1. In another embodiment, n is 2. In another embodiment, n is 3. In another embodiment, n is 4. In another embodiment, n is 5. In another embodiment, n is 6. In another embodiment, n is 7. In another embodiment, n is 8.

In certain embodiments, the anti-CD19 antibody of the ADC comprises complementarity determining regions (CDRs) as set forth as SEQ ID NO: 1, SEQ ID NO: 2, SEQ ID NO: 3, SEQ ID NO: 4, SEQ ID NO: 5, and SEQ ID NO: 6. In certain embodiments, the anti-CD19 antibody comprises a heavy chain variable region set forth as SEQ ID NO: 7 and a light chain variable region set forth as SEQ ID NO: 8. In certain embodiments, the anti-CD19 antibody comprises a heavy chain set forth as SEQ ID NO: 9 or SEQ ID NO:11 and a light chain set forth as SEQ ID NO: 10 and n is primarily 2, 4 and 6. In an embodiment, the ADC is ADC-1, in which the antibody is CD19 mAb. In certain embodiments, the anti-CD19 antibody heavy chain is encoded by the nucleotide sequence set forth as SEQ ID NO: 12 and the light chain is encoded by the nucleotide sequence set forth as SEQ ID NO: 13.

7.3. Compositions

The anti-CD19 GRM agonist ADCs of this disclosure may be provided as a composition suitable for administration to a subject. In some embodiments, the anti-CD19 GRM agonist ADC composition is a pharmaceutical composition, comprising an anti-CD19 GRM agonist ADC of this disclosure and a pharmaceutically acceptable carrier.

An ADC composition may comprise a mixture of ADCs having different n integer values, according to structural formula II. The number of GRM agonist drugs linked to an ADC depends on the number of available attachments sites on the antibody. The "drug-to-antibody ratio," or "DAR", as used herein, refers to the molar ratio of GRM drugs to antibody in the ADC composition.

In embodiments, the formulation consists essentially of a mixture of ADCs according to structural formula II having n values of 2,4, and 6, and the DAR is between 2 and 6.

7.4. Methods of Use

In certain embodiments, the methods described herein involve treating patients who have B-cell malignancies, such as diffuse large B-cell lymphoma (DLBCL), acute lymphoblastic leukemia (ALL), follicular lymphoma (FL), and chronic lymphocytic leukemia (CLL) with a CD19 GRM agonist ADC. In embodiments, a composition comprising a CD19 GRM agonist ADC is administered to a subject in need thereof. In embodiments, the method comprises administration of an ADC that results in the delivery of the compound of Formula III, the compound of Formula IV, or the compounds of both Formula III and IV to the subject. In embodiments, the compound of Formula III, the compound of Formula IV, or the compounds of both Formula III and IV are delivered to a B-cell malignancy within a subject.

Given as a single agent, CD19-GRM agonist ADCs inhibit subcutaneous xenograft growth of human tumor cell lines derived from B-cell malignancies, see Examples relating to Diffuse Large B-Cell Lymphoma (DLBCL: OCI-LY19 and SU-DHL-6; see FIGS. 8 and 10) and Acute Lymphoblastic Leukemia (ALL: RS4; 11; see FIG. 9).

7.5. Process for Producing Anti-CD19 ADCs

In certain embodiments, described herein is a process for producing anti-CD19-GRM agonist ADCs. In a specific embodiment, described herein is a process for producing an antiCD19-GRM agonist ADC, wherein the antibody is an anti-CD19 antibody comprising two heavy chains each consisting of the amino acid sequence set forth as SEQ ID NO: 9 or SEQ ID NO: 11, and two light chains each consisting of the amino acid sequence set forth as SEQ ID NO: 10; wherein the antibody is afucosylated at position ASN-303 of SEQ ID NO: 9 or SEQ ID NO: 11 (EU: ASN-297); wherein the process comprises the steps of reducing the antibody with an excess of reducing agent followed by conjugating the antibody with an excess of the drug linker of Formula V.

8. EXEMPLARY EMBODIMENTS

While various specific embodiments have been illustrated and described, and some are represented below, it will be appreciated that various changes can be made without departing from the spirit and scope of the inventions(s).

1. An anti-CD19 antibody-drug conjugate comprising the following structure:

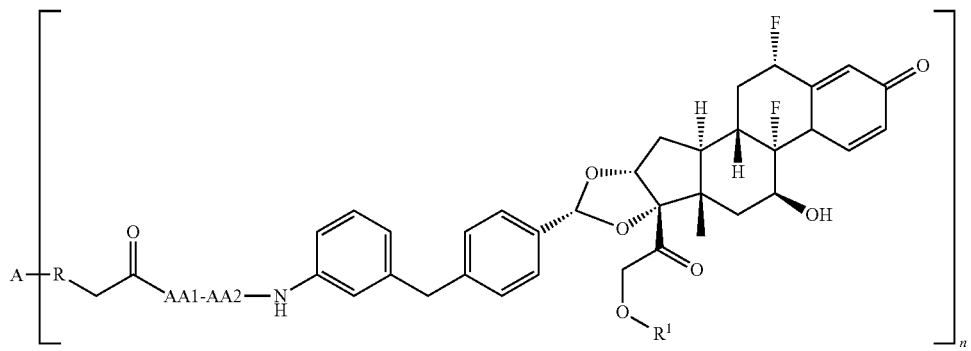

wherein:
  A is an antibody;
  R is the point of attachment of the antibody via a cysteine residue of the antibody providing an —S— group when linked;
  AA1 and AA2 are Alanine (Ala);
  $R^1$ is hydrogen or —P(=O)(OH)$_2$;
  n is an integer from 1 to 10;
wherein the antibody is an anti-CD19 antibody comprising
  a heavy chain variable region comprising a CDR-H1 domain, CDR-H2 domain, and a CDR-H3 domain; and
  a light chain variable region comprising a CDR-L1 domain, a CDR-L2 domain, and a CDR-L3 domain, wherein
  CDR-H1 comprises the amino acid sequence GFTFTTYWIN (SEQ ID NO: 1),
  CDR-H2 comprises the amino acid sequence NIYPSDSYTNYNQKFKD (SEQ ID NO: 2),
  CDR-H3 comprises the amino acid sequence EDYYGSSSYYAMDY (SEQ ID NO: 3);
  CDR-L1 comprises the amino acid sequence KASQDVGTAVA (SEQ ID NO: 4),
  CDR-L2 comprises the amino acid sequence WASTRHT (SEQ ID NO: 5), and
  CDR-L3 comprises the amino acid sequence QQYSTYPLT (SEQ ID NO: 6).

2. The anti-CD19 antibody-drug conjugate of embodiment 1, wherein the antibody is an IgG antibody.

3. The anti-CD19 antibody-drug conjugate of embodiment 2, wherein the antibody is an IgG1 antibody.

4. The anti-CD19 antibody-drug conjugate of embodiment 1, wherein the antibody comprises a heavy chain variable region comprising the amino acid sequence set forth as SEQ ID NO: 7 and a light chain variable region comprising the amino acid sequence set forth as SEQ ID NO: 8.

5. The anti-CD19 antibody-drug conjugate of embodiment 1, wherein the antibody comprises a heavy chain comprising the amino acid sequence set forth as SEQ ID NO: 9 or SEQ ID NO: 11, and a light chain comprising the amino acid sequence set forth as SEQ ID NO: 10.

6. The anti-CD19 antibody-drug conjugate of embodiment 1, wherein the antibody consists of two identical heavy chains and two identical light chains, wherein each heavy chain consists of the amino acid sequence set forth as SEQ ID NO: 9 or SEQ ID NO: 11, and wherein each light chain consists of the amino acid sequence set forth as SEQ ID NO: 10.

7. The anti-CD19 antibody-drug conjugate according to any one of embodiments 1-6, wherein the antibody is afucosylated.

8. The anti-CD19 antibody-drug conjugate according to embodiment 7, wherein the antibody is 70% or more, 80% or more, 90% or more, or about 99%, or about 100% afucosylated.

9. The anti-CD19 antibody-drug conjugate according to embodiment 7 or embodiment 8, wherein the afucosylation is at position ASN-303 of SEQ ID NO: 9 or SEQ ID NO: 11 (EU: ASN-297).

10. A pharmaceutical composition comprising an anti-CD19 antibody-drug conjugate of any one of embodiments 1-9 and a pharmaceutically acceptable carrier.

11. A method of treating a B-cell malignancy, the method comprising administering an antibody-drug conjugate according to any one of embodiments 1-9 to a patient in need thereof.

12. The anti-CD19 antibody-drug conjugate of any one of embodiments 1-9, wherein n is 2, 4 or 6.

13. The anti-CD19 antibody-drug conjugate of any one of embodiments 1-9, wherein n is 2.

14. The anti-CD19 antibody-drug conjugate of any one of embodiments 1-9, wherein n is 4.

15. The anti-CD19 antibody-drug conjugate of any one of embodiments 1-9, wherein n is 6.

16. An anti-CD19 antibody comprising
  a heavy chain variable region comprising a CDR-H1 domain, CDR-H2 domain, and a CDR-H3 domain; and
  a light chain variable region comprising a CDR-L1 domain, a CDR-L2 domain, and a CDR-L3 domain, wherein
  CDR-H1 comprises the amino acid sequence GFTFTTYWIN (SEQ ID NO: 1),
  CDR-H2 comprises the amino acid sequence NIYPSDSYTNYNQKFKD (SEQ ID NO: 2),
  CDR-H3 comprises the amino acid sequence EDYYGSSSYYAMDY (SEQ ID NO: 3);
  CDR-L1 comprises the amino acid sequence KASQDVGTAVA (SEQ ID NO: 4),
  CDR-L2 comprises the amino acid sequence WASTRHT (SEQ ID NO: 5), and
  CDR-L3 comprises the amino acid sequence QQYSTYPLT (SEQ ID NO: 6).

17. The anti-CD19 antibody of embodiment 16, wherein the antibody is an IgG antibody.

18. The anti-CD19 antibody of embodiment 17 wherein the antibody is an IgG1 antibody.

19. The anti-CD19 antibody according to embodiment 16, wherein the antibody comprises a heavy chain variable region comprising the amino acid sequence set forth as SEQ ID NO: 7 and a light chain variable region comprising the amino acid sequence set forth as SEQ ID NO: 8.

20. The anti-CD19 antibody according to embodiment 16, wherein the antibody comprises a heavy chain comprising the amino acid sequence set forth as SEQ ID NO: 9 or SEQ ID NO: 11, and a light chain comprising the amino acid sequence set forth as SEQ ID NO: 10.

21. The anti-CD19 antibody according to any one of embodiments 16-20, wherein the antibody is afucosylated.

22. The anti-CD19 antibody according to embodiment 21, wherein the antibody is 70% or more, 80% or more, 90% or more, or about 99%, or about 100% afucosylated.

23. The anti-CD19 antibody according to embodiment 21 or embodiment 22, wherein the afucosylation is at position ASN-303 of SEQ ID NO: 9 or SEQ ID NO: 11 (EU: ASN-297).

24. The anti-CD19 antibody according to embodiment 16 or 19, wherein the antibody is an IgG1 antibody, IgG2 antibody, IgG3 antibody, IgG4 antibody, humanized antibody, single chain antibody, single domain antibody, camelized antibody, scFv-Fc antibody, Fab, Fab', (Fab')$_2$, Fv or an scFv.

25. The anti-CD19 antibody according to embodiment 24, wherein the antibody is afucosylated.

26. The anti-CD19 antibody according to embodiment 25, wherein the antibody is 70% or more, 80% or more, 90% or more, or about 99%, or about 100% afucosylated.

27. The anti-CD19 antibody according to embodiment 25 or embodiment 26, wherein the afucosylation is at position ASN-303 of SEQ ID NO: 9 or SEQ ID NO: 11 (EU: ASN-297).

28. An anti-CD19 antibody-drug conjugate comprising the following structure:

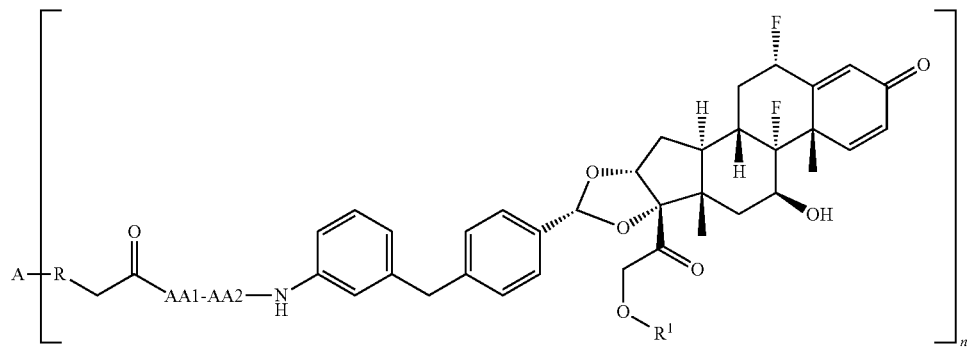

wherein:

A is an antibody;

R is the point of attachment of the antibody via a cysteine residue of the antibody providing an —S— group when linked;

AA1 and AA2 are Alanine (Ala);

$R^1$ is —P(=O)(OH)$^2$;

n is an integer from 2 to 8;

wherein the antibody is an anti-CD19 antibody comprising two heavy chains each consisting of the amino acid sequence set forth as SEQ ID NO: 9 or SEQ ID NO: 11, and two light chains each consisting of the amino acid sequence set forth as SEQ ID NO: 10, wherein the antibody is afucosylated at position ASN-303 of SEQ ID NO: 9 or SEQ ID NO: 11 (EU: ASN-297).

29. The anti-CD19 antibody according to embodiment 28, wherein n is 2.

30. The anti-CD19 antibody according to embodiment 28, wherein n is 4.

31. The anti-CD19 antibody according to embodiment 28, wherein n is 6.

32. The anti-CD19 antibody according to embodiment 28, wherein n is 8.

33. One or more polynucleotides encoding the anti-CD19 antibody according to embodiment 16.

34. A process for producing an anti-CD19 antibody-drug conjugate comprising the following structure:

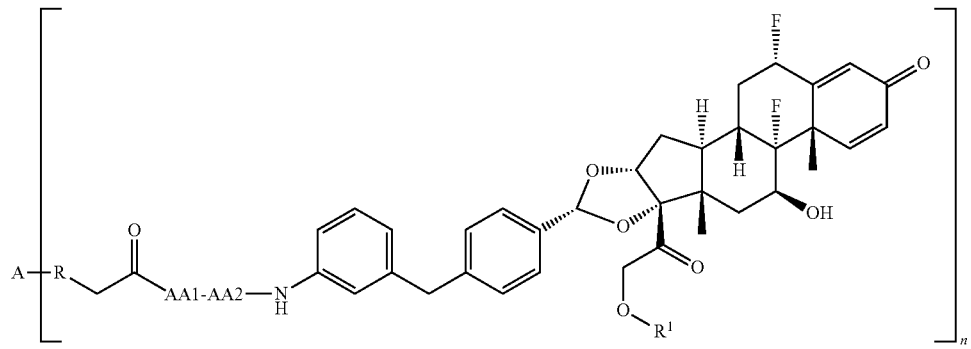

wherein:

A is an antibody;

R is the point of attachment of the antibody via a cysteine residue of the antibody providing an —S— group when linked;

AA1 and AA2 are Alanine (Ala);

$R^1$ is —P(=O)(OH)$^2$;

n is an integer from 2 to 8;

wherein the antibody is an anti-CD19 antibody comprising two heavy chains each consisting of the amino acid sequence set forth as SEQ ID NO: 9 or SEQ ID NO: 11, and two light chains each consisting of the amino acid sequence set forth as SEQ ID NO: 10, wherein the antibody is afucosylated at position ASN-303 of SEQ ID NO: 9 or SEQ ID NO: 11 (EU: ASN-297).

wherein the process comprises the steps of reducing the antibody with an excess of reducing agent followed by conjugating the antibody with an excess of the drug linker comprising the following structure:

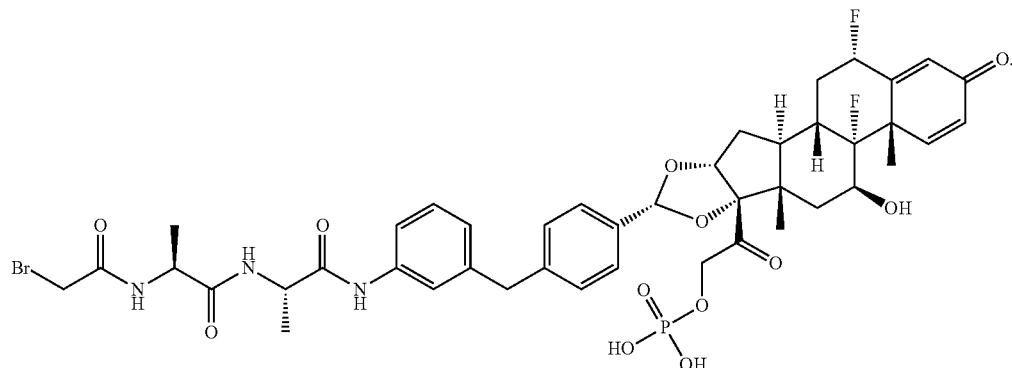

9. EXAMPLES

The following examples, which highlight certain features and properties of the exemplary embodiments of the antibodies and binding fragments described herein are provided for purpose of illustration.

9.1. Example 1: CD19 Antibody Generation

A CD19 antibody consisting of the complementarity determining regions (CDRs) of a murine antibody clone 4B12 (mouse anti-human CD19) was isolated using hybridoma technology. These CDR sequences (SEQ ID NOs: 1-6) were cloned into human IgG1 heavy chain and human kappa light chain constant region domains with nine murine variable heavy chain framework back mutations and two murine variable light chain framework back mutations to generate H chain (SEQ ID NO: 9) and L chain (SEQ ID NO: 10) sequences. The humanized CD19 antibody (CD19 mAb) retains the CD19 binding potency and selectivity of the parental mouse hybridoma clone 4B12.

Chinese hamster ovary (CHO) cells were transfected by electroporation with an expression vector (pCD-CD19 antibody) designed to express the CD19 antibody. The cells were grown in chemically defined medium enabling selection of cell expressing DHFR from the expression vector and the CD19 antibody. Cells were grown and clonal outgrowth was screened for anti-CD19 antibody expression. Based on the screening, a stable transfectant was identified as the parental cell line for further development.

This stable transfectant was then transfected with an additional vector (pYH9neo-RMD, which expresses the *Pseudomonas* enzyme GDP-6-deoxy-D-lyxo-4-hexulose reductase (RMD)) by electroporation. This expression vector enables the production of afucosylated CD19 antibody (greater than or equal to 90% afucosylated) in a cell line defective in GDP-fucose formation, due to for example a deficiency in GDP-mannose 4,6-dehydratase. Clonal cells were screened for growth and expression of afucosylated CD19 antibody. A final subclone was selected and a Master Cell Bank was generated.

9.2. Example 2: Synthesis of ADC-1, a CD19 GRM Agonist ADC

9.2.1. Overview

A CD19 GRM agonist ADC was formed by conjugating an anti-CD19 antibody of Example 1 (to a linker drug that contains the GRM of formula I wherein $R^1$ is a phosphate group). The phosphate-GRM payload of Formula (III):

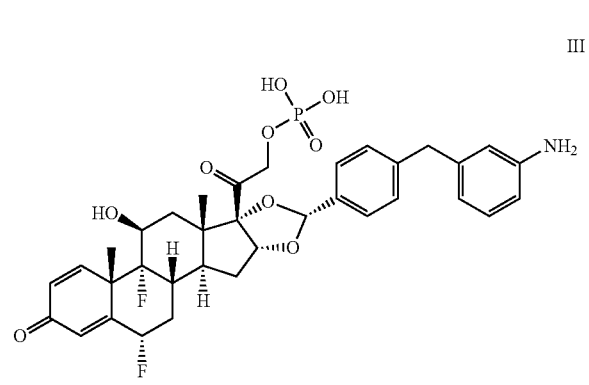

is conjugated to CD19 antibody via an alanine-alanine cleavable linker. Upon administration of the ADC, the phosphate-GRM payload of Formula III is converted to the GRM of Formula IV:

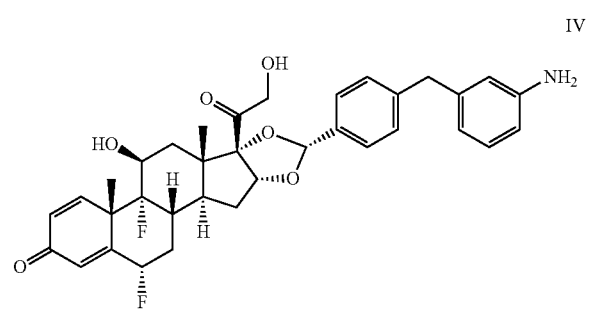

The conjugated material is processed using hydrophobic interaction chromatography (HIC) to substantially reduce antibodies containing 0 conjugated linker drugs and ADCs containing 8 GRM molecules per antibody, resulting in the final drug product comprising a mixture of ADCs containing primarily 2, 4 or 6 GRM molecules, with a DAR of between 2 and 6.

The analytical procedures used to generate ADC-1, a CD19 GRM agonist ADC, are described in detail below.

9.2.2. Small Molecule Analytical Procedures

Unless otherwise stated, all $^1$H and $^{13}$C NMR (Nuclear magnetic resonance) data were collected on a Varian Mercury Plus 400 MHz, Agilent MR 400 MHz, or a Bruker AVIII 300, 400, 500, or 600 MHz instrument; chemical shifts are quoted in parts per million (ppm). High performance liquid chromatography (HPLC) and LCMS analytical data are either detailed within the experimental or referenced to the conditions listed in Table 1.

TABLE 1

List of LCMS and HPLC Methods

| Method | Conditions |
|---|---|
| a | LCMS Conditions. The gradient was 1-90% B in 3.4 min, 90-100% B in 0.45 min, 100-1% B in 0.01 min, and then held at 1% B for 0.65 min (0.8 mL/min flow rate). Mobile phase A was 0.0375% Trifluoro acetic acid in $H_2O$, mobile phase B was 0.018% trifluoroacetic acid in acetonitrile. The column used for the chromatography was a 2.0 × 50 mm Phenomenex Luna-C18 column (5 μm particles). Detection methods are Diode array (DAD) and Evaporative light scattering detector (ELSD) as well as positive electrospray ionization. |
| b | LCMS Conditions: Mobile phase A was 0.037% TFA in water, and mobile phase B was 0.018% TFA in HPLC grade acetonitrile. The gradient was 5-95% B in 2.00 min .5% B in 0.01 min, 5-95% B (0.01-1.00 min), 95-100% B (1.00-1.80 min), 5% B in 1.81 min with a hold at 5% B for 0.19 min. The flow rate was 1.0 mL/min (0.00-1.80 min) and 1.2 mL/min (1.81-2.00 min). The column used for chromatography was a Luna-C18 2.0*30 mm, (3 μm particles). MS range was 100-2000. Detection methods are diode array (DAD). MS mode was positive electrospray ionization. |
| c | LCMS Conditions: A gradient of 5-100% acetonitrile (A) and 0.1% trifluoroacetic acid in water (B) was used, at a flow rate of 1.5 mL/min (0-0.05 min 5% A, 0.05-1.2 min 5-100% A, 1.2-1.4 min 100% A, 1.4-1.5 min 100-5% A. 0.25 min post-run delay). Analytical LC-MS was performed on a Thermo MSQ-Plus mass spectrometer and Agilent 1100/1200 HPLC system running Xcalibur 2.0.7, Open-Access 1.4, and custom login software. The mass spectrometer was operated under positive APCI or ESI ionization conditions dependent on the system used. The HPLC system comprised an Agilent Binary pump, degasser, column compartment, autosampler and diode-array detector, with a Polymer Labs ELS-2100 evaporative light-scattering detector. The column used was a Phenomenex Kinetex C8, 2.6 μm 100 Å (2.1 mm × 30 mm), at a temperature of 65° C. |
| d | LCMS Conditions: A gradient of 5-100% acetonitrile (A) and 10 mM ammonium acetate in water (B) was used, at a flow rate of 1.5 mL/min (0-0.05 min 5% A, 0.05-1.2 min 5-100% A, 1.2-1.4 min 100% A, 1.4-1.5 min 100-5% A. 0.25 min post-run delay). Analytical LC-MS was performed on a Thermo MSQ-Plus mass spectrometer and Agilent 1100/1200 HPLC system running Xcalibur 2.0.7, Open-Access 1.4, and custom login software. The mass spectrometer was operated under positive ESI ionization conditions. The HPLC system comprised an Agilent Binary pump, degasser, column compartment, autosampler and diode-array detector, with a Polymer Labs ELS-2100 evaporative light-scattering detector. The column used was a Phenomenex Kinetex C8, 2.6 μm 100 Å (2.1 mm × 30 mm), at a temperature of 65° C. |

9.2.3. Synthesis Of Precursor Molecules 9.2.3.1. Synthesis of (2S,6aS,6bR,7S,8aS,8bS,10R,11aR,12aS,12bS)-10-(4-(3-Aminobenzyl)phenyl)-2,6b-difluoro-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one (GRM of Formula IV)

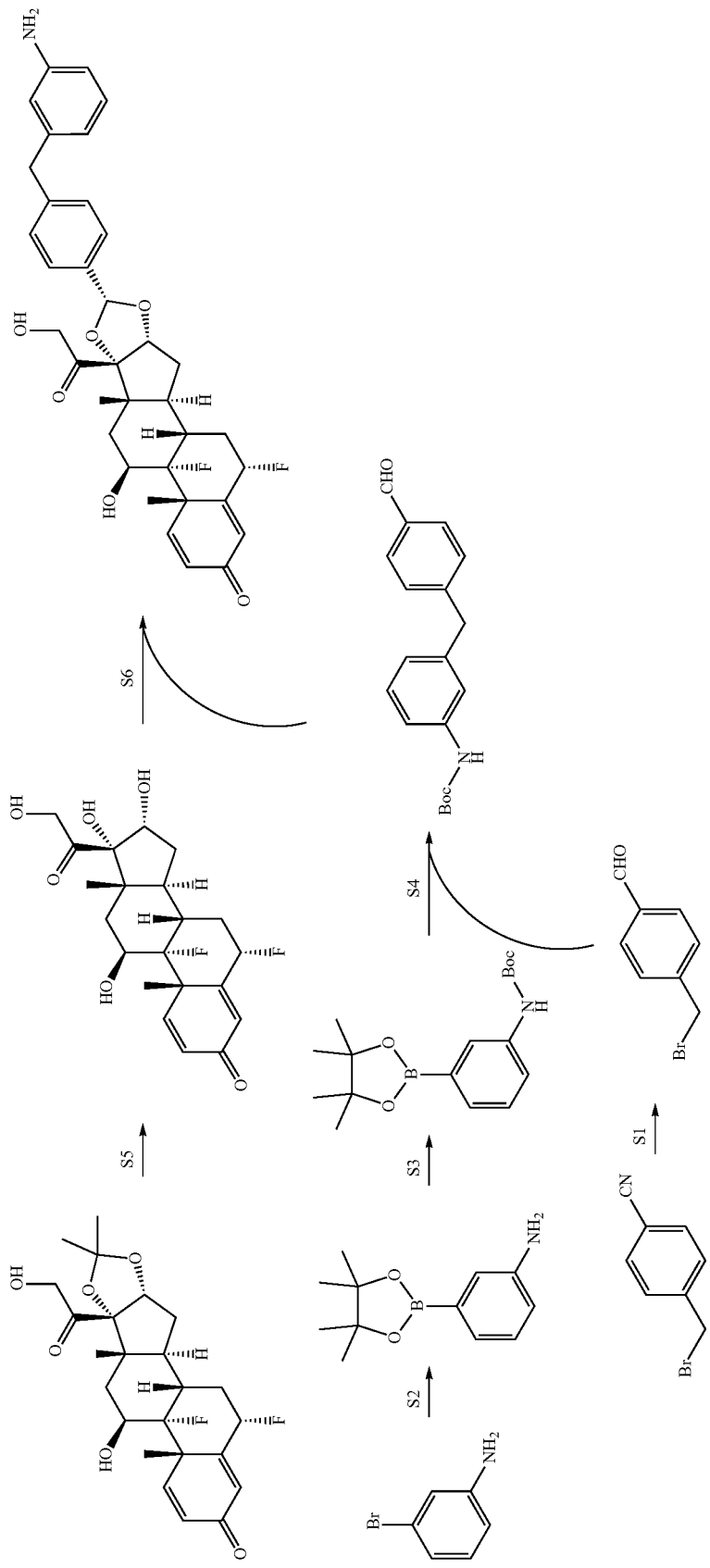

Step 1: Synthesis of 4-(bromomethyl)benzaldehyde. Diisobutylaluminum hydride (153 mL, 153 mmol, 1 M in toluene) was added drop-wise to a 0° C. solution of 4-(bromomethyl)benzonitrile (20 g, 102 mmol) in toluene (400 mL) over 1 hour. Two additional reactions were set up as described above. All three reaction mixtures were combined for purification. The combined reaction mixtures were quenched with 10% aqueous HCl (1.5 L), extracted with dichloromethane (3×500 mL), dried ($Na_2SO_4$), and solvent was removed under reduced pressure. Purification by column chromatography (silica gel) eluting with 10:1 petroleum ether/ethyl acetate gave the title compound (50 g, 82% yield). $^1$H NMR (400 MHz, $CDCl_3$) δ 10.02 (s, 1H), 7.91-7.82 (m, 2H), 7.56 (d, J=7.9 Hz, 2H), 4.55-4.45 (m, 2H).

Step 2: Synthesis of 3-(4,4,5,5-tetramethyl-1,3,2-dioxaborolan-2-yl)aniline. To a solution of 3-bromoaniline (40 g, 233 mmol) in 1,4-dioxane (480 mL) was added 4,4,4',4',5,5,5',5'-octamethyl-2,2'-bi(1,3,2-dioxaborolane) (94 g, 372 mmol), potassium acetate (45.6 g, 465 mmol), 2-dicyclohexylphosphino-2',4',6'-tri-1-propyl-1,1'-biphenyl (8.07 g, 13.95 mmol), tris(dibenzylideneacetone)dipalladium(0) (8.52 g, 9.30 mmol). Then the resulting mixture was heated at 80° C. for 4 hours under nitrogen. An additional reaction was set up as described above. The two reaction mixtures were combined and solvent removed under reduced pressure. Purification by column chromatography (silica gel) eluting with 10:1 petroleum ether/ethyl acetate gave the title compound (60 g, 55.4% yield). $^1$H NMR (400 MHz, $CDCl_3$) δ 7.23-7.13 (m, 3H), 6.80 (d, J=7.5 Hz, 1H), 3.82-3.38 (m, 2H), 1.34 (s, 12H).

Step 3: Synthesis of tert-butyl (3-(4,4,5,5-tetramethyl-1,3,2-dioxaborolan-2-yl)phenyl)carbamate. 3-(4,4,5,5-Tetramethyl-1,3,2-dioxaborolan-2-yl)aniline (30 g, 137 mmol) and di-tert-butyl dicarbonate (38.9 g, 178 mmol) were mixed in toluene (600 mL) at 100° C. for 24 hours. Another reaction was set up as described above. The two reaction mixtures were combined and solvent removed under reduced pressure. The crude residue was dissolved in ethyl acetate (1.5 L), washed with 0.1 N aq. HCl (3×2 L), brine (3 L), dried ($Na_2SO_4$), filtered and concentrated under reduced pressure to give the title compound (50 g, 57% yield). $^1$H NMR (400 MHz, $CDCl_3$) δ 7.63 (br m, 2H), 7.48 (d, J=7.1 Hz, 1H), 7.37-7.28 (m, 1H), 1.52 (s, 9H), 1.34 (s, 12H).

Step 4: Synthesis of tert-butyl (3-(4-formylbenzyl)phenyl)carbamate. A mixture of 4-(bromomethyl)benzaldehyde (24.94 g, 125 mmol), 1,1'-bis(diphenylphosphino) ferrocenedichloro palladium(II) dichloromethane (13.75 g, 18.80 mmol), tert-butyl (3-(4,4,5,5-tetramethyl-1,3,2-dioxaborolan-2-yl)phenyl)carbamate (20 g, 62.7 mmol) and potassium carbonate (43.3 g, 313 mmol) in tetrahydrofuran (400 mL) was heated to 80° C. for 12 hours. Another additional reaction was set up as described above. The two reaction mixtures were combined, diluted with water (500 mL), and extracted with ethyl acetate (3×500 mL). The combined organic layers were dried ($Na_2SO_4$) and solvent removed under reduced pressure. Purification by column chromatography (silica gel) eluting with 10:1 petroleum ether/ethyl acetate gave the title compound (15 g, 38.4% yield). $^1$H NMR (400 MHz, $CDCl_3$) δ 9.95 (s, 1H), 7.78 (d, J=7.9 Hz, 2H), 7.33 (d, J=7.9 Hz, 2H), 7.27-7.13 (m, 3H), 6.82 (d, J=7.1 Hz, 1H), 6.47 (br. s., 1H), 4.00 (s, 2H), 1.48 (s, 9H).

Step 5: Synthesis of (6S,8S,9R,10S,11S,13S,14S,16R,17S)-6,9-difluoro-11,16,17-trihydroxy-17-(2-hydroxyacetyl)-10,13-dimethyl-6,7,8,9,10,11,12,13,14,15,16,17-dodecahydro-3H-cyclopenta[a]phenanthren-3-one. (2S,6aS,6bR,7S,8aS,8bS,11aR,12aS,12bS)-2,6b-Difluoro-7-hydroxy-8b-(2-hydroxyacetyl)-6a,8a,10,10-tetramethyl-1,2,6a,6b,7,8,8a,8b,11a,12,12a,12b-dodecahydro-4H-naphtho[2',1':4,5]indeno[1,2-d][1,3]dioxol-4-one (20 g, 44.2 mmol) was suspended in 40% aqueous $HBF_4$ (440 mL) and the mixture was stirred at 25° C. for 48 hours. After the reaction was complete, 2 L of water was added and the solid collected by filtration. The solid was washed with water (1 L) and then methanol (200 mL) to give the title compound (11 g, 60.3% yield). $^1$H NMR (400 MHz, DMSO-d6) δ 7.25 (d, J=10.1 Hz, 1H), 6.28 (d, J=10.1 Hz, 1H), 6.10 (s, 1H), 5.73-5.50 (m, 1H), 5.39 (br. s., 1H), 4.85-4.60 (m, 2H), 4.50 (d, J=19.4 Hz, 1H), 4.20-4.04 (m, 2H), 2.46-2.06 (m, 6H), 1.87-1.75 (m, 1H), 1.56-1.30 (m, 6H), 0.83 (s, 3H).

Step 6: Synthesis of (2S,6aS,6bR,7S,8aS,8bS,10R,11aR,12aS,12bS)-10-(4-(3-aminobenzyl)phenyl)-2,6b-difluoro-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one. A suspension of (6S,8S,9R,10S,11S,13S,14S,16R,17S)-6,9-difluoro-11,16,17-trihydroxy-17-(2-hydroxyacetyl)-10,13-dimethyl-6,7,8,9,10,11,12,13,14,15,16,17-dodecahydro-3H-cyclopenta[a]phenanthren-3-one (4.4 g, 10.67 mmol) and $MgSO_4$ (6.42 g, 53.3 mmol) in acetonitrile (100 mL) was stirred at 20° C. for 1 hour. A solution of tert-butyl (3-(4-formylbenzyl)phenyl)carbamate (3.65 g, 11.74 mmol) in acetonitrile (100 mL) was added in one portion. Trifluoromethanesulfonic acid (9.01 mL, 53.3 mmol) was added dropwise while maintaining an internal temperature below room temperature using an ice bath. After the addition, the mixture was stirred at 20° C. for 2 hours. Three additional reactions were set up as described above. All four reaction mixtures were combined and solvent was removed under reduced pressure. Purification by prep HPLC gave the title compound (4.5 g, 14.2% yield). LCMS (Method a, Table 1) $R_t$=2.65 min; MS m/z=606.2 (M+H)$^+$. $^1$H NMR (400 MHz, DMSO) δ 7.34 (d, J=7.7 Hz, 2H), 7.24 (dd, J=16.2, 9.0 Hz, 3H), 6.88 (t, J=7.8 Hz, 1H), 6.43-6.33 (m, 3H), 6.30 (d, J=10.2 Hz, 1H), 6.13 (s, 1H), 5.75-5.55 (m, 1H), 5.52 (d, J=4.1 Hz, 1H), 5.44 (s, 1H), 5.11 (t, J=6.0 Hz, 1H), 4.94 (s, 3H), 4.51 (dd, J=19.6, 6.5 Hz, 1H), 4.29-4.07 (m, 2H), 3.73 (s, 2H), 2.76-2.55 (m, 1H), 2.39-2.13 (m, 2H), 2.10-1.96 (m, 1H), 1.85-1.61 (m, 3H), 1.61-1.39 (m, 4H), 0.86 (s, 3H). Prep HPLC Method: Instrument: Gilson 281 semi-preparative HPLC system; Mobile phase: A: Formic Acid/$H_2O$=0.01% v/v; B: Acetonitrile; Column: Luna C18 150*25 5 micron; Flow rate: 25 mL/min; Monitor wavelength: 220 and 254 nm.

TABLE 2

| Mobile phase conditions for eluant B | | | | | | |
|---|---|---|---|---|---|---|
| Time (min) | 0.0 | 10.5 | 10.6 | 10.7 | 13.7 | 13.8 | 15.0 |
| B % | 15 | 35 | 35 | 100 | 100 | 10 | 10 |

9.2.3.2. Synthesis of 2-((2S,6aS,6bR,7S,8aS,8bS,10R,11aR,12aS,12bS)-10-(4-(3-Aminobenzyl)phenyl)-2,6b-difluoro-7-hydroxy-6a,8a-dimethyl-4-oxo-1,2,4,6a,6b,7,8,8a,11a,12,12a,12b-dodecahydro-8bH-naphtho[2',1':4,5]indeno[1,2-d][1,3]dioxol-8b-yl)-2-oxoethyl dihydrogen phosphate (phosphate-GRM of Formula III)

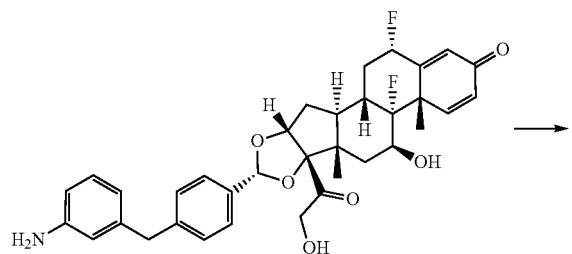

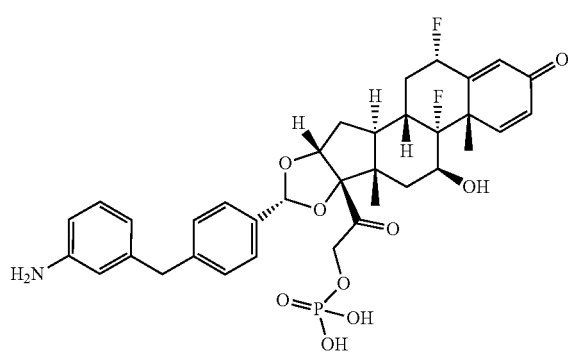

Diphosphoryl chloride (6.86 g, 27.2 mmol) was added dropwise to a −40° C. solution of (2S,6aS,6bR,7S,8aS,8bS,10R,11aR,12aS,12bS)-10-(4-(3-aminobenzyl)phenyl)-2,6b-difluoro-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one (3.30 g, 5.45 mmol) and para-toluenesulfonic acid (0.938 g, 5.45 mmol) in tetrahydrofuran (30 mL). The mixture was stirred at −40° C. for 2 h. Three additional reactions were set up as described above. The combined reaction mixtures were quenched with water (450 mL) at −40° C., warmed to 0° C. and adjusted to pH ~7 by addition of sat. aq. NaHCO$_3$. The suspension was filtered at pH ~6 due to large liquid volume filling up the flask. The filtrate was then adjusted to pH 7 and rinsed through the filtered solid. The filtrate was acidified back to pH 3 by addition of 1 M aq. HCl (200 mL), which resulted in a suspension. The mixture was filtered, and the combined solid was rinsed with the mother liquors twice and collected. The crude solid was dried under vacuum and purified by prep HPLC on a Nano-micro Kromasil C18 3 micron column (100×40 mm). A gradient of acetonitrile (A) and 1% trifluoroacetic acid in water_(B) was used, at a flow rate of 50 mL/min (0-5.0 min 20% A, 5.0-25.0 min linear gradient 20-50% A, hold for 5 min). Purified fractions were adjusted to pH ~5 and lyophilized to give the title compound (3.50 g, 23% yield) as a white solid. LCMS (Method b, Table 1) Rt=0.707 min, m/z 686.2 (M+H$^+$). $^1$H NMR (400 MHz, DMSO-d6) δ 7.35 (d, J=7.9 Hz, 2H), 7.26 (td, J=7.3, 6.2, 3.1 Hz, 3H), 7.07 (t, J=7.9 Hz, 1H), 6.73-6.60 (m, 3H), 6.30 (dd, J=10.2, 1.9 Hz, 1H), 6.12 (d, J=2.4 Hz, 1H), 5.75-5.55 (m, 1H), 5.54 (s, 1H), 4.98-4.86 (m, 2H), 4.59 (dd, J=18.2, 8.3 Hz, 1H), 4.25-4.17 (m, 1H), 3.83 (s, 2H), 2.79-2.56 (m, 1H), 2.37-2.17 (m, 2H), 2.05 (dt, J=13.7, 3.6 Hz, 1H), 1.72 (q, J=9.3, 8.1 Hz, 3H), 1.60-1.41 (m, 1H), 1.50 (s, 3H), 0.88 (s, 3H). $^{19}$F NMR (376 MHz, DMSO-d6) δ −73.76, −164.99, −186.36. $^{31}$P NMR (162 MHz, DMSO-d6) δ −1.17.

9.2.3.3. Synthesis of (S)-2-(2-Bromoacetamido)-N—((S)-1-((3-(4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-1-oxopropan-2-yl)propanamide (Drug Linker of Formula VI)

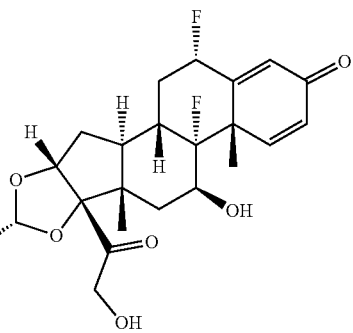

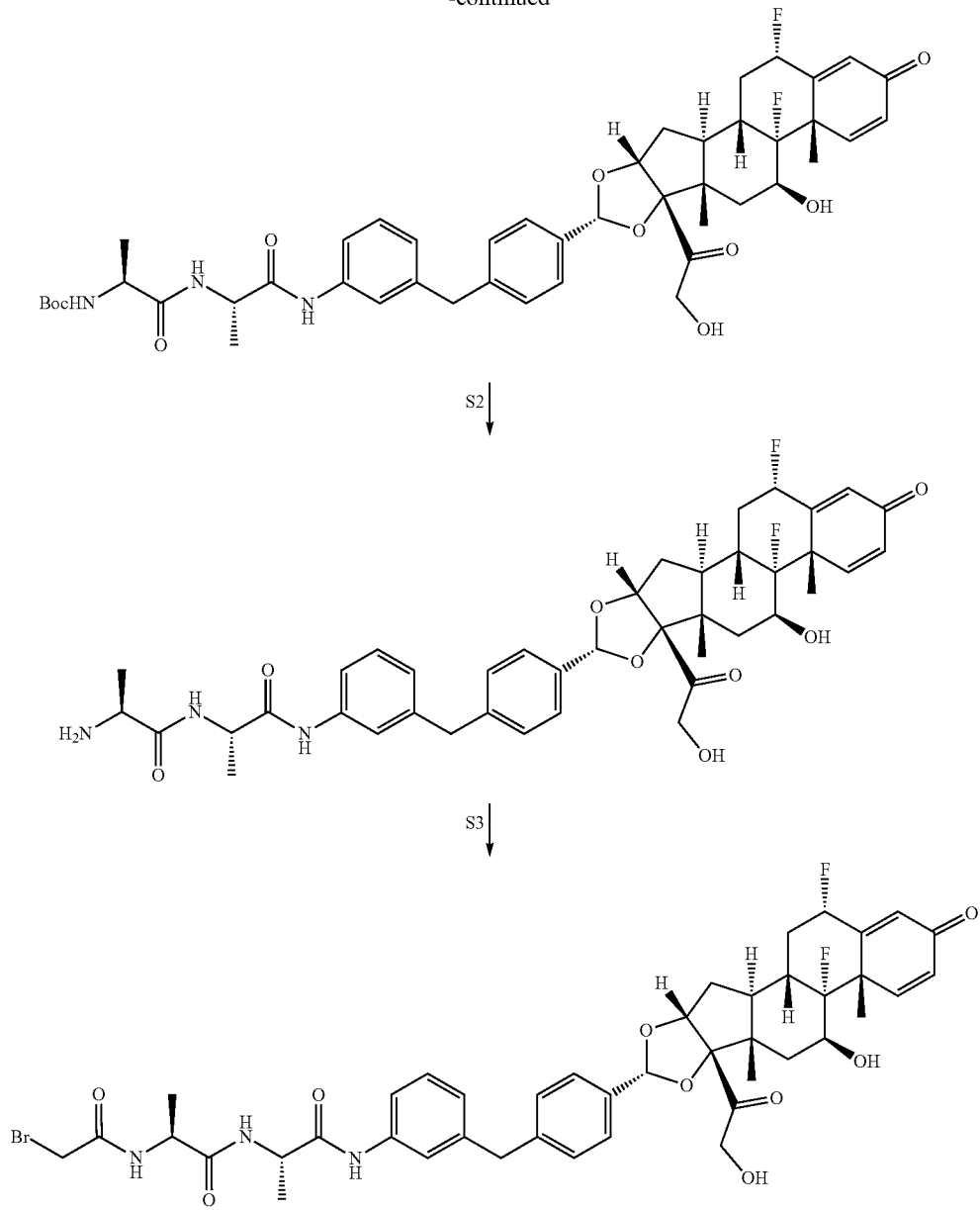

Step 1: Synthesis of tert-Butyl ((S)-1-(((S)-1-((3-(4-((2S, 6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4, 6a,6b,7,8,8a,8b,11a,12,12a,12b-dodecahydro-1H-naphtho [2',1':4,5]indeno[1,2-d][1,3]dioxol-10-yl)benzyl)phenyl) amino)-1-oxopropan-2-yl)amino)-1-oxopropan-2-yl) carbamate.

2,6-Lutidine (0.5 mL, 4.29 mmol) was added to a room temperature suspension of the (2S,6aS,6bR,7S,8aS,8bS, 10R,11aR,12aS,12bS)-10-(4-(3-aminobenzyl)phenyl)-2,6b-difluoro-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one (0.505 g, 0.834 mmol), (S)-2-((S)-2-((tert-butoxycarbonyl)amino) propanamido)propanoic acid [CAS no. 27317-69-7, purchased from Chem-Impex International, Inc.] (0.217 g, 0.835 mmol), and HATU (1-[bis(dimethylamino)methyl-ene]-1H-1,2,3-triazolo[4,5-b]pyridinium 3-oxid hexafluorophosphate) (0.481 g, 1.266 mmol) in tetrahydrofuran (5.5 mL). After 16 h, the reaction was diluted with EtOAc (40 mL) and washed with 1 N aq. HCl (2×20 mL), sat. aq. NaHCO$_3$ (20 mL), brine (20 mL), dried (Na$_2$SO$_4$), filtered and solvent removed under reduced pressure. Purification by chromatography (silica, 40 g) eluting with a gradient of 0-10% MeOH/DCM gave the title compound (0.648 g, 92% yield) as an off-white solid. LCMS (Method c, ESI, Table 1) Rt=0.89 min, m/z=848.6 (M+H$^+$). $^1$H NMR (600 MHz, DMSO-d6) δ 9.82 (s, 1H), 7.94 (d, J=7.3 Hz, 1H), 7.46 (d, J=7.9 Hz, 1H), 7.38 (t, J=2.0 Hz, 1H), 7.38-7.33 (m, 2H), 7.26 (dd, J=10.2, 1.5 Hz, 1H), 7.26-7.22 (m, 2H), 7.19 (t, J=7.9 Hz, 1H), 6.95 (d, J=7.4 Hz, 1H), 6.91 (dt, J=7.7, 1.2 Hz, 1H), 6.29 (dd, J=10.1, 1.9 Hz, 1H), 6.14-6.11 (m, 1H), 5.72-5.56 (m, 1H), 5.53-5.49 (m, 1H), 5.44 (s, 1H), 5.09 (t, J=5.9 Hz, 1H), 4.94 (d, J=5.2 Hz, 1H), 4.51 (dd, J=19.4, 6.1

Hz, 1H), 4.35 (t, J=7.1 Hz, 1H), 4.23-4.16 (m, 2H), 3.97 (t, J=7.2 Hz, 1H), 3.88 (s, 2H), 2.65 (ddt, J=28.2, 15.3, 7.9 Hz, 1H), 2.36-2.16 (m, 2H), 2.07-2.01 (m, 1H), 1.78-1.63 (m, 3H), 1.57-1.50 (m, 1H), 1.49 (s, 3H), 1.36 (s, 9H), 1.26 (d, J=7.1 Hz, 3H), 1.20-1.15 (m, 3H), 0.86 (s, 3H).

Step 2: Synthesis of (S)-2-Amino-N—((S)-1-((3-(4-((2S, 6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4, 6a,6b,7,8,8a,8b,11a,12,12a,12b-dodecahydro-1H-naphtho [2',1':4,5]indeno[1,2-d][1,3]dioxol-10-yl)benzyl)phenyl) amino)-1-oxopropan-2-yl)propanamide Trifluoroacetic acid (2.0 mL, 26.0 mmol) was added to a room temperature solution of tert-butyl ((S)-1-(((S)-1-((3-(4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl) benzyl)phenyl)amino)-1-oxopropan-2-yl)amino)-1-oxopropan-2-yl)carbamate (0.648 g, 0.764 mmol). The reaction was stirred in an open flask for 20 min, then solvent was removed under reduced pressure. The residue was dissolved in EtOAc (60 mL), was washed with sat. aq. NaHCO$_3$ (3×20 mL), saturated aqueous NaBr (20 mL), dried (Na$_2$SO$_4$), filtered and solvent removed under reduced pressure. Trituration of the residue with MTBE/heptanes and removal of solvent gave the title compound which was used without further purification in the next step. LCMS (Method c, ESI, Table 1) Rt=0.72 min; m/z 748.5 (M+H$^+$).

Step 3: Synthesis of (S)-2-(2-Bromoacetamido)-N—((S)-1-((3-(4-((2S,6aS,6bR,7S,8aS,8bS,10R,11aR,12aS,12bS)-2, 6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3] dioxol-10-yl)benzyl)phenyl)amino)-1-oxopropan-2-yl) propanamide.

2,6-Lutidine (0.2 mL, 1.717 mmol) was added to a room temperature solution of (S)-2-amino-N—((S)-1-((3-(4-((2S, 6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4, 6a,6b,7,8,8a,8b,11a,12,12a,12b-dodecahydro-1H-naphtho [2',1':4,5]indeno[1,2-d][1,3]dioxol-10-yl)benzyl)phenyl) amino)-1-oxopropan-2-yl)propanamide (0.286 g, 0.382 mmol) and bromoacetic acid N-hydroxysuccinimide ester (0.414 g, 1.753 mmol) in dimethyl formamide (4 mL). The reaction was complete within 20 min by LCMS. A second reaction of the same size was set up. Both reactions were combined for purification by prep HPLC on a Phenomenex C18(2) 10 micron column (250×50 mm). A gradient of acetonitrile (A) and 1% trifluoroacetic acid in water (B) was used, at a flow rate of 90 mL/min (0-5.0 min 15% A, 5.0-20.0 min linear gradient 15-95% A, hold for 5 min). Product fractions were freeze-dried to give the title compound (0.254 g, 38% yield) as a white solid. LCMS (Method c, ESI, Table 1) Rt=0.82 min, m/z 868.4, 870.3 (M+H)$^+$. $^1$H NMR (600 MHz, DMSO-d6) δ 9.82 (s, 1H), 8.45 (d, J=7.3 Hz, 1H), 8.20 (d, J=7.2 Hz, 1H), 7.46 (dd, J=8.4, 2.2 Hz, 1H), 7.40 (t, J=1.9 Hz, 1H), 7.38-7.33 (m, 2H), 7.28-7.19 (m, 4H), 7.19 (d, J=7.9 Hz, 1H), 6.91 (dt, J=7.7, 1.3 Hz, 1H), 6.29 (dd, J=10.2, 1.9 Hz, 1H), 6.12 (d, J=2.0 Hz, 1H), 5.64 (dddd, J=48.5, 11.4, 6.8, 1.9 Hz, 1H), 5.51 (d, J=4.4 Hz, 1H), 5.45 (s, 1H), 4.94 (d, J=5.3 Hz, 1H), 4.51 (d, J=19.4 Hz, 1H), 4.40-4.33 (m, 1H), 4.31 (p, J=7.2 Hz, 1H), 4.23-4.16 (m, 2H), 3.94-3.87 (m, 4H), 2.71-2.58 (m, 1H), 2.27 (ddq, J=31.2, 12.4, 6.3, 5.7 Hz, 1H), 2.04 (dt, J=13.7, 3.7 Hz, 1H), 1.77-1.63 (m, 3H), 1.57-1.50 (m, 1H), 1.50 (s, 3H), 1.27 (d, J=7.1 Hz, 3H), 1.21 (d, J=7.1 Hz, 3H), 0.86 (s, 3H).

9.2.3.4. Synthesis of 2-((2S,6aS,6bR,7S,8aS,8bS, 10R,11aR,12aS,12bS)-10-(4-(3-((S)-2-((S)-2-(2-Bromoacetamido)propanamido)propanamido)benzyl)phenyl)-2,6b-difluoro-7-hydroxy-6a,8a-dimethyl-4-oxo-1,2,4,6a,6b,7,8,8a,11a,12,12a,12b-dodecahydro-8bH-naphtho[2',1':4,5]indeno[1,2-d][1, 3]dioxol-8b-yl)-2-oxoethyl dihydrogen phosphate (Drug linker of Formula V)

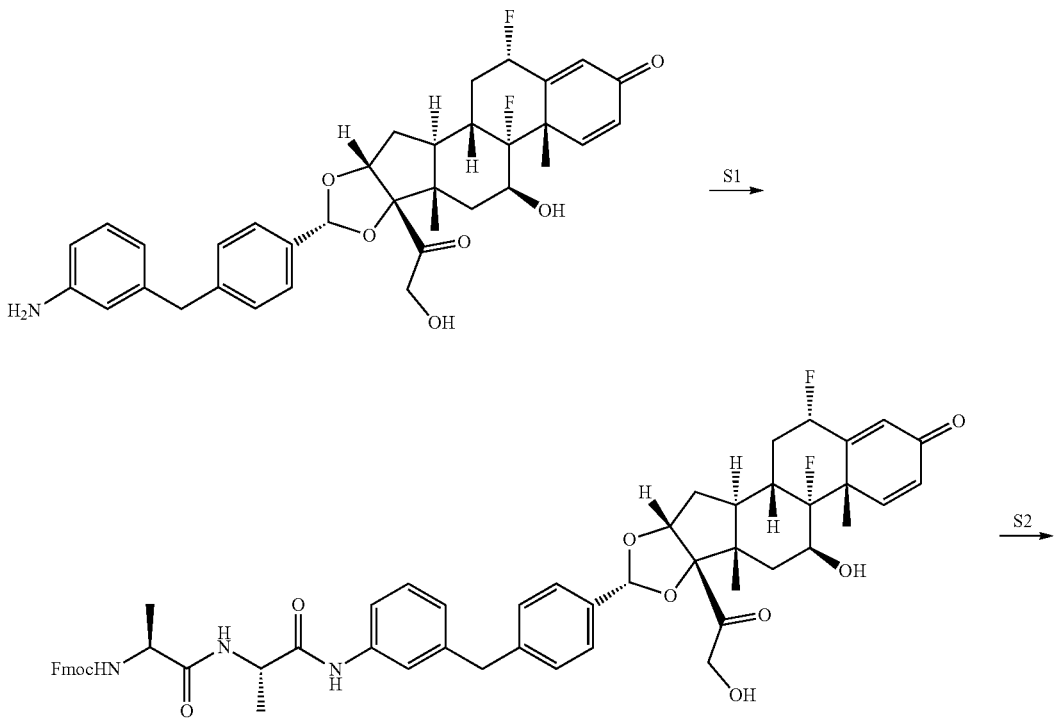

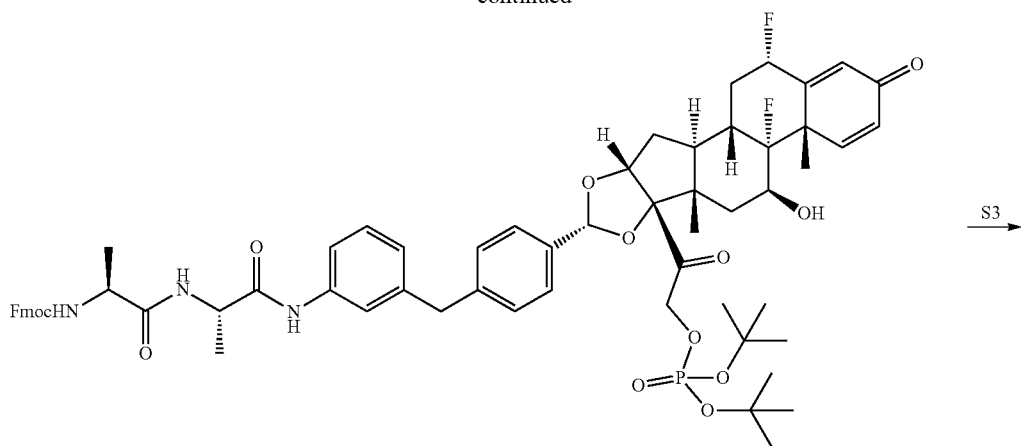
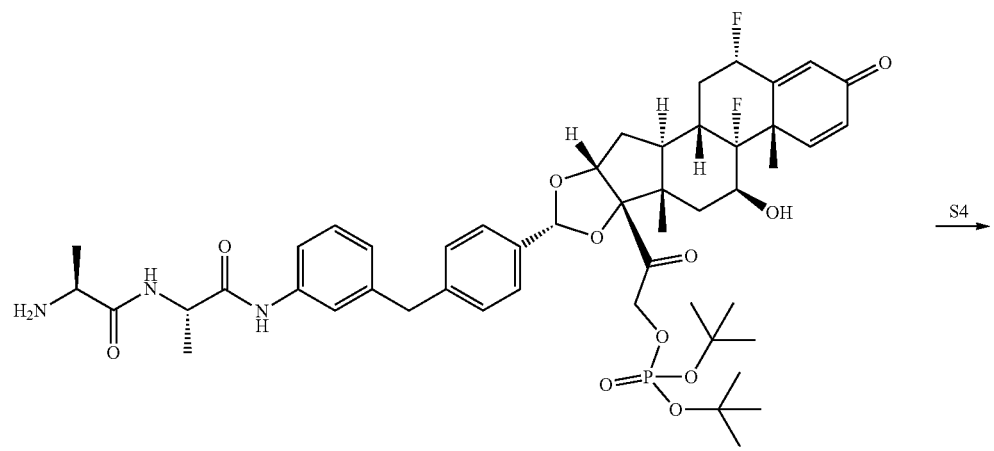
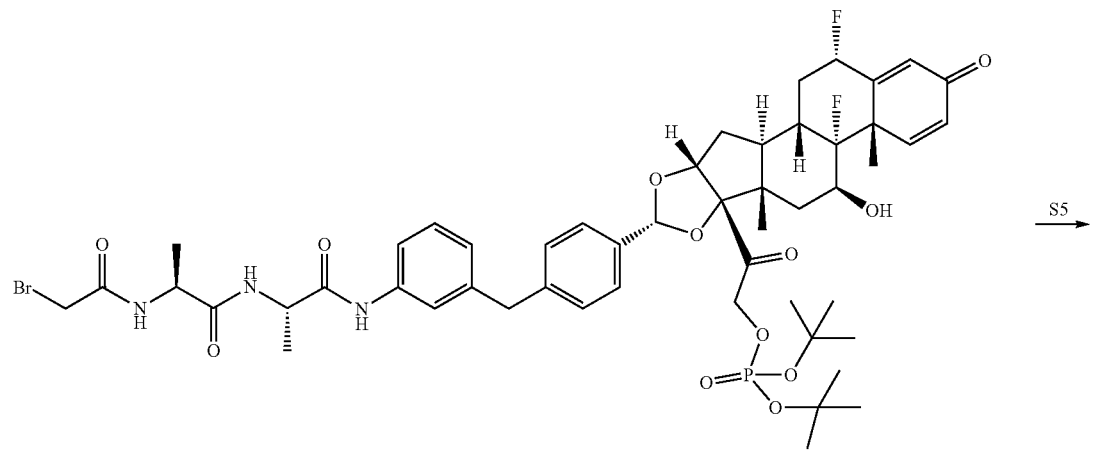

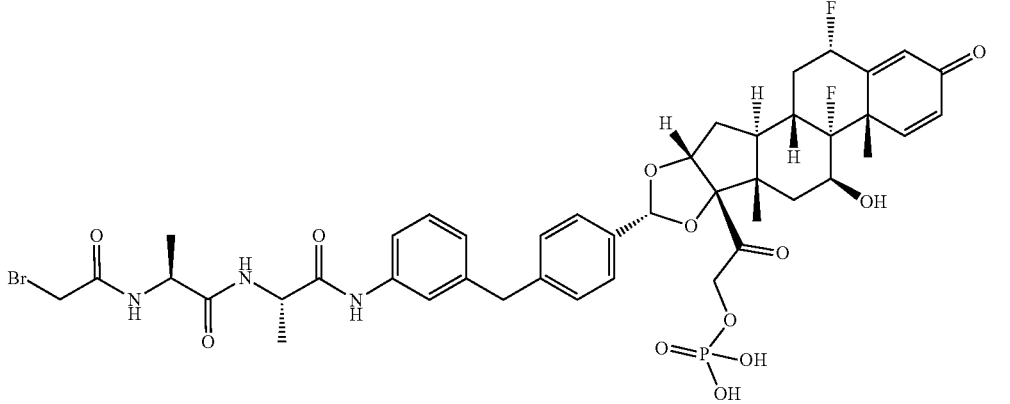

Step 1: Synthesis of (9H-Fluoren-9-yl)methyl((S)-1-(((S)-1-((3-(4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-1-oxopropan-2-yl)amino)-1-oxopropan-2-yl)carbamate.

2,6-Lutidine (1.2 mL, 10.30 mmol) was added to a room temperature solution of (2S,6aS,6bR,7S,8aS,8bS,10R,11aR,12aS,12bS)-10-(4-(3-aminobenzyl)phenyl)-2,6b-difluoro-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one (1.377 g, 2.27 mmol), (((9H-fluoren-9-yl)methoxy)carbonyl)-L-alanyl-L-alanine [CAS no. 87512-31-0, purchased from Chem-Impex International, Inc.] (0.878 g, 2.295 mmol), and HATU (1-[bis(dimethylamino)methylene]-1H-1,2,3-triazolo[4,5-b]pyridinium 3-oxid hexafluorophosphate) (1.327 g, 3.49 mmol) in tetrahydrofuran (15 mL). After 15 h, the mixture was diluted with EtOAc (100 mL) and washed with 1 N aq. HCl (2×50 mL), sat. aq. NaHCO₃ (50 mL), brine (50 mL), dried (Na₂SO₄), filtered and solvent removed under reduced pressure. Purification by chromatography (silica, 120 g) eluting with a gradient of 0-10% MeOH/DCM gave the product (1.98 g, 90% yield) as a white solid. LCMS (Method c, APCI, Table 1) Rt=0.98 min, m/z 970.6 (M+H⁺). ¹H NMR (400 MHz, DMSO-d6) δ 9.83 (s, 1H), 8.06 (d, J=7.3 Hz, 1H), 7.91-7.84 (m, 2H), 7.71 (t, J=7.8 Hz, 2H), 7.53 (d, J=7.4 Hz, 1H), 7.49-7.13 (m, 12H), 6.91 (dt, J=7.7, 1.4 Hz, 1H), 6.29 (dd, J=10.2, 1.9 Hz, 1H), 6.14 (q, J=1.6 Hz, 1H), 5.73-5.54 (m, 1H), 5.52 (dd, J=4.4, 1.8 Hz, 1H), 5.44 (s, 1H), 5.10 (t, J=5.9 Hz, 1H), 4.95 (d, J=4.8 Hz, 1H), 4.51 (dd, J=19.5, 6.2 Hz, 1H), 4.37 (p, J=7.0 Hz, 1H), 4.30-4.14 (m, 5H), 4.14-4.02 (m, 1H), 3.86 (s, 2H), 2.74-2.55 (m, 1H), 2.35-2.18 (m, 2H), 2.08-1.96 (m, 1H), 1.77-1.61 (m, 3H), 1.60-1.49 (m, 1H), 1.50 (s, 3H), 1.27 (d, J=7.1 Hz, 3H), 1.23 (d, J=7.1 Hz, 3H), 0.86 (s, 3H).

Step 2: Synthesis of (9H-Fluoren-9-yl)methyl((S)-1-(((S)-1-((3-(4-((2S,6aS,6bR,7S,8aS,8bS,10R,11aR,12aS,12bS)-8b-(2-((di-tert-butoxyphosphoryl)oxy)acetyl)-2,6b-difluoro-7-hydroxy-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-1-oxopropan-2-yl)amino)-1-oxopropan-2-yl)carbamate.

Di-tert-butyl N,N-diethylphosphoramidite (1.8 mL, 6.02 mmol) was added to a room temperature solution of (9H-fluoren-9-yl)methyl((S)-1-(((S)-1-((3-(4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-1-oxopropan-2-yl)amino)-1-oxopropan-2-yl)carbamate (1.98 g, 2.041 mmol) and tetrazole (0.45 M in acetonitrile) (18 mL, 8.10 mmol). After 50 min, the reaction was treated with hydrogen peroxide (30% in water, 1.2 mL, 11.75 mmol). After 10 min, the reaction was treated with 1 M aq. NaS₂O₃ (80 mL) to quench any unreacted hydrogen peroxide [CAUTION: exothermic!]. The mixture was extracted with EtOAc (3×60 ml). The combined organic layers were washed with brine (50 mL), dried (Na₂SO₄), filtered and solvent removed under reduced pressure. Purification by chromatography (silica, 120 g) eluting with a gradient of 0-10% MeOH/DCM gave the desired product (1.85 g, 78% yield) as a white foam. LCM (Method d, ESI, Table 1) Rt=1.12 min, m/z 1162.7 (M+H⁺).

Step 3: Synthesis of 2-((2S,6aS,6bR,7S,8aS,8bS,10R,11aR,12aS,12bS)-10-(4-(3-((S)-2-((S)-2-Aminopropanamido)propanamido)benzyl)phenyl)-2,6b-difluoro-7-hydroxy-6a,8a-dimethyl-4-oxo-1,2,4,6a,6b,7,8,8a,11a,12,12a,12b-dodecahydro-8bH-naphtho[2',1':4,5]indeno[1,2-d][1,3]dioxol-8b-yl)-2-oxoethyl di-tert-butyl phosphate.

Piperidine (1.0 ml, 10.10 mmol) was added to a room temperature solution of (9H-fluoren-9-yl)methyl((S)-1-(((S)-1-((3-(4-((2S,6aS,6bR,7S,8aS,8bS,10R,11aR,12aS,12bS)-8b-(2-((di-tert-butoxyphosphoryl)oxy)acetyl)-2,6b-difluoro-7-hydroxy-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-1-oxopropan-2-yl)amino)-1-oxopropan-2-yl)carbamate (1.854 g, 1.595 mmol) in tetrahydrofuran (16 mL). After 25 min the solvent was removed under reduced pressure. The residue was iteratively treated with toluene (3×30 mL), which was removed under reduced pressure after each treatment to ensure removal of piperidine. Assumed 100% yield and used the crude product in the next step without further purification. LCMS (Method d, ESI, Table 1) Rt=1.11 min, m/z 940.7 (M+H⁺).

Step 4: Synthesis of 2-((2S,6aS,6bR,7S,8aS,8bS,10R,11aR,12aS,12bS)-10-(4-(3-((S)-2-((S)-2-(2-Bromoacetamido)propanamido)propanamido)benzyl)phenyl)-2,6b-difluoro-7-hydroxy-6a,8a-dimethyl-4-oxo-1,2,4,6a,6b,7,8,8a,11a,12,12a,12b-dodecahydro-8bH-naphtho[2',1':4,5]indeno[1,2-d][1,3]dioxol-8b-yl)-2-oxoethyl di-tert-butyl phosphate.

EEDQ (2-ethoxy-1-ethoxycarbonyl-1,2-dihydroquinoline) (1.630 g, 6.59 mmol) was added to a room temperature solution of bromoacetic acid (0.680 g, 4.90 mmol) in dimethyl formamide (4 mL). The mixture was stirred for 90 min in order to activate the bromoacetic acid for coupling. Separately, 2-((2S,6aS,6bR,7S,8aS,8bS,10R,11aR,12aS,12bS)-10-(4-(3-((S)-2-((S)-2-aminopropanamido)propanamido)benzyl)phenyl)-2,6-difluoro-7-hydroxy-6a,8a-dimethyl-4-oxo-1,2,4,6a,6b,7,8,8a,11a,12,12a,12b-dodecahydro-8bH-naphtho[2',1':4,5]indeno[1,2-d][1,3]dioxol-8b-yl)-2-oxoethyl di-tert-butyl phosphate (1.499 g, 1.595 mmol) was dissolved in dimethyl formamide (8 mL). This solution was transferred to the vial containing the activated bromoacetic acid. Due to incomplete reaction, a second charge of activated bromoacetic acid was prepared: bromoacetic acid (0.363 g, 2.61 mmol) was added to a solution of EEDQ (2-ethoxy-1-ethoxycarbonyl-1,2-dihydroquinoline) (0.813 g, 3.29 mmol) in dimethyl formamide (3 mL) and stirred for 70 min, and then combined with the reaction mixture. After 15 min the reaction was diluted with EtOAc (60 mL) and washed with water (2×20 mL), dried ($Na_2SO_4$), filtered, and solvent removed under reduced pressure. Purification by chromatography (silica, 80 g) eluting with a gradient of 0-10% MeOH/DCM gave the product (0.760 g, 45% yield) as a white solid. LCMS (Method c, ESI, Table 1) Rt=1.03 min, m/z 1060.6, 1062.1 (M+H$^+$). $^1$H NMR (400 MHz, DMSO-d6) δ 9.83 (s, 1H), 8.47 (d, J=7.3 Hz, 1H), 8.22 (d, J=7.2 Hz, 1H), 7.49-7.43 (m, 1H), 7.41 (t, J=1.9 Hz, 1H), 7.35 (d, J=8.2 Hz, 2H), 7.32-7.23 (m, 3H), 7.19 (t, J=7.8 Hz, 1H), 6.91 (dt, J=7.7, 1.4 Hz, 1H), 6.30 (dd, J=10.2, 1.9 Hz, 1H), 6.12 (d, J=2.2 Hz, 1H), 5.74-5.55 (m, 2H), 5.56 (s, 1H), 5.03-4.90 (m, 2H), 4.65 (dd, J=18.0, 9.3 Hz, 1H), 4.34 (dt, J=15.6, 7.2 Hz, 2H), 4.26-4.16 (m, 1H), 3.94-3.86 (m, 4H), 3.31 (s, 1H), 2.75-2.56 (m, 1H), 2.35-2.17 (m, 2H), 2.07 (d, J=13.2 Hz, 1H), 1.72 (td, J=13.9, 4.2 Hz, 2H), 1.67-1.52 (m, 1H), 1.49 (s, 3H), 1.42 (s, 9H), 1.42 (s, 9H), 1.27 (d, J=7.1 Hz, 3H), 1.20 (d, J=7.0 Hz, 3H), 0.89 (s, 3H).

Step 5: Synthesis of 2-((2S,6aS,6bR,7S,8aS,8bS,10R,11aR,12aS,12bS)-10-(4-(3-((S)-2-((S)-2-(2-Bromoacetamido)propanamido)propanamido)benzyl)phenyl)-2,6-difluoro-7-hydroxy-6a,8a-dimethyl-4-oxo-1,2,4,6a,6b,7,8,8a,11a,12,12a,12b-dodecahydro-8bH-naphtho[2',1':4,5]indeno[1,2-d][1,3]dioxol-8b-yl)-2-oxoethyl dihydrogen phosphate.

Trifluoroacetic acid (2.5 mL, 32.4 mmol) was added to a room temperature solution of 2-((2S,6aS,6bR,7S,8aS,8bS,10R,11aR,12aS,12bS)-10-(4-(3-((S)-2-((S)-2-(2-bromoacetamido)propanamido)propanamido)benzyl)phenyl)-2,6-difluoro-7-hydroxy-6a,8a-dimethyl-4-oxo-1,2,4,6a,6b,7,8,8a,11a,12,12a,12b-dodecahydro-8bH-naphtho[2',1':4,5]indeno[1,2-d][1,3]dioxol-8b-yl)-2-oxoethyl di-tert-butyl phosphate (0.760 g, 0.716 mmol) in dichloromethane (5 mL). After 15 min of stirring in an open vessel the solvent was removed under reduced pressure to give a foam, which was dissolved in 3:1 acetonitrile/water (16 mL) and purified by prep HPLC on a Phenomenex C18(2) 10 micron column (250×50 mm). A gradient of acetonitrile (A) and 1% trifluoroacetic acid in water (B) was used, at a flow rate of 90 mL/min (0-5.0 min 15% A, 5.0-20.0 min linear gradient 15-95% A, hold for 5 min). Product fractions were freeze-dried to give the title compound (0.291 g, 43% yield) as a white solid. LCMS (Method c, APCI, Table 1) Rt=0.84 min, m/z 948.4, 950.4 (M+H$^+$). $^1$H NMR (600 MHz, DMSO-d6) δ 9.83 (s, 1H), 8.46 (d, J=7.4 Hz, 1H), 8.21 (d, J=7.3 Hz, 1H), 7.46 (ddd, J=8.2, 2.2, 1.1 Hz, 1H), 7.39 (t, J=1.9 Hz, 1H), 7.38-7.33 (m, 2H), 7.29-7.23 (i, 3H), 7.19 (t, J=7.8 Hz, 1H), 6.91 (dt, J=7.7, 1.3 Hz, 1H), 6.30 (dd, J=10.1, 1.9 Hz, 1H), 6.13 (dt, J=2.6, 1.3 Hz, 1H), 5.64 (dddd, J=48.3, 11.1, 6.4, 1.9 Hz, 2H), 5.53 (s, 1H), 4.96-4.89 (i, 2H), 4.59 (dd, J=18.1, 8.4 Hz, 1H), 4.34 (dp, J=23.2, 7.1 Hz, 2H), 4.21 (d, J G 9.0 Hz, 1H), 3.93-3.88 (m, 4H), 2.72-2.61 (m, 1H), 2.32-2.20 (m, 2H), 2.09-2.03 (m, 1H), 1.72 (dd, J=12.8, 6.3 Hz, 2H), 1.68 (s, 1H), 1.57-1.49 (min, 1H), 1.49 (s, 3H), 1.27 (d, J=7.1 Hz, 3H), 1.21 (d, J=7.1 Hz, 3H), 0.88 (s, 3H).

9.2.4. Conjugation and Analytical Methods

9.2.4.1. Small Molecule Analytical Procedures

High performance liquid chromatography (HPLC) and LCMS analytical data are either detailed within the experimental or referenced to the conditions listed in Table 3.

TABLE 3

List of LCMS and HPLC Methods

| Method | Conditions |
|---|---|
| a | HIC method - HPLC column = BioSuite Phenyl Column, 7.5 × 75 mm column, 10 μm, 1000 Å, Waters; Mobile phase A: 25 mM $Na_2HPO_4$, 1.0M $(NH_4)_2SO_4$, pH 7.0; Mobile phase B: 25 mM $Na_2HPO_4$ pH 7.0/IPA, v/v = 65/35; Flow rate: 700 μL/min; Gradient: 0 min, 18.7% B, hold to 3.6 min at 18.7% B then to 94% B at 46.4 min, then return to 18.7% B at 47.9 min and hold to 59.0 min at 18.7% B.; Column temperature: 20° C.; monitor 254 and 280 nm. |
| b | SEC method - HPLC column = Tosoh Bioscience TSK-gel SW3000xl 5 μm, 7.8 × 300 mm; Mobile phase: 7.5% Isopropanol in 100 mM Sodium Phosphate/100 mM Sodium Sulfate, pH 6.8; Flow rate: 1.0 mL/min; Column temperature: 20° C.; monitor 214 and 280 nm. |
| c | HIC method - HPLC column = Sepax, Proteomix HIC Butyl-NP 4.6 × 35 mm, 1.7 μm; Mobile phase A: 25 mM $Na_2HPO_4$, 1.5M $(NH_4)_2SO_4$, pH 7.0; Mobile phase B: 25 mM $Na_2HPO_4$ pH 7.0/IPA, v/v = 75/25; Flow rate: 300 μL/min; Gradient: 0 min, 15% B to 100% B at 17 min, hold to 20 min at 100% B; Column temperature: 20° C.; monitor 254 and 280 nm. |
| d | SEC method - HPLC column = Acquity UPLC Protein BEH SEC, 200 A, 1.7 μm, 4.6 × 300 mm; Mobile phase: 90% 100 mM Phosphate buffer and 150 mM NaCl pH 7.0/10% MeCN; Flow rate: 200 μL/min; Column temperature: 30° C.; monitor 214 and 280 nm. |

9.2.4.2. CD19 Phosphorylated GRM Agonist ADC 170.4 g of CD19 antibody (CD19 mAb) of Example 1 at a concentration of ~50 mg/mL was diluted with PBE (125 mM phosphate 6 mM EDTA pH 7.3) buffer in 1:1 w/w and partially reduced with tris(2-carboxyethyl)phosphine hydrochloride (TCEP) (2.6 equivalents, 0.847 g, 25 mM solution in water for injection (WFI)) at ~4° C. overnight under nitrogen. The reduced antibody was then conjugated to drug linker of Formula V:

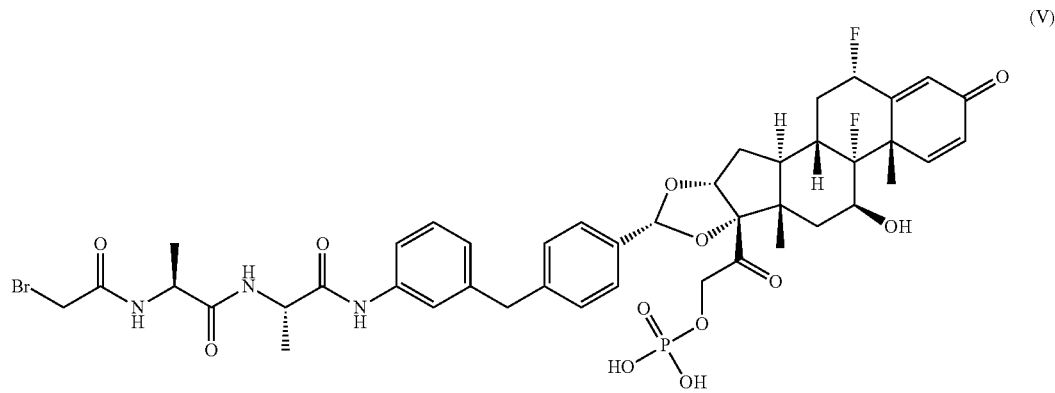

(6.0 equivalents, 6.92 g, 93.2% w/w %, solution in dimethylacetamide (DMA) 650 g) by addition at ~4° C. followed by warming to 20° C. and holding 6-8 hours till judged complete. The conjugation was quenched by addition of N-acetyl cysteine (20 equivalents, 3.71 g, 100 mM solution in WFI). The product solution was split into 2 portions followed by dilution of each to ~13 L with WFI followed by pH adjustment to ~8.5 with NaOH as the load solution. Each load solution was purified.

9.2.4.3. Mass Spectroscopy

ADC samples were fully reduced before MS analysis. The mass spectrometry conditions used are as follows: HPLC column=Waters BioResolve RP mAb Polyphenyl 450A 2.7 um, 150×2.1 mm; Mobile phase A: 0.1% difluoroacetic acid in water; Mobile phase B: 0.1% difluoroacetic acid in acetonitrile; Flow rate: 0.4 mL/min; Gradient: Start 20% B, 0 to 12 min 20-45% B, 14 to 16 min 45-60% B, 16 to 18 min, 60-100% B, re-equilibrate 20% B for 4 min; Column temperature: 80° C.; MS ionization source: ESI.

A reduced reverse phase (A280) chromatograph and deconvoluted mass spectrum of each subunit were generated. See FIG. 16. Peaks corresponding to the light chain with zero or one drug linker molecule attached and the heavy chain with zero, one, two or three drug linker molecules attached were resolved and identified.

9.2.4.4. CD19 Desphosphate GRM Agonist ADC 2.82 g of CD19 antibody (CD19 mAb) of Example 1 at a concentration of ~50 mg/mL was diluted with PBE (125 mM phosphate 6 mM EDTA pH 7.3) buffer in 1:1 w/w and partially reduced with TCEP (2.56 equivalents, 0.0141 g, 4.93 mM solution in WFI) at ~4° C. overnight under nitrogen. The reduced antibody was then conjugated to drug linker of Formula VI

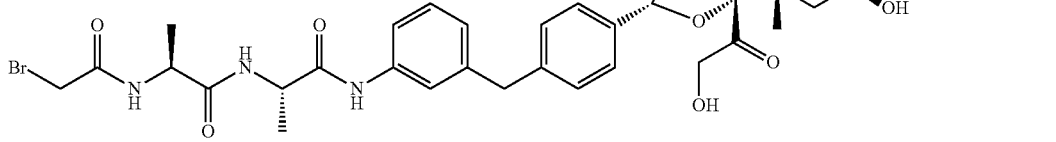

(6.1 equivalents, 0.102 g, 90.2% w/w %, solution in DMA 11 g) by addition at ~4° C. followed by warming to 20° C. and holding 6-8 hours till judged complete. The conjugation was quenched by addition of N-acetyl cysteine (10 equivalents, 0.031 g, 100 mM solution in WFI). The product solution was salted with 0.8 M ammonium sulfate 25 mM sodium phosphate pH 7.1 (126 g) to prepare the load solution in preparation for purification. The load solution was purified.

9.3. Example 3: Characterization of Antibody and ADC

The binding and cellular activity of the CD19 Phosphorylated GRM agonist ADC of Example 2, section 8.2.4.2

(ADC-1) and its parental afucosylated antibody (also referred to as CD19 mAb) were characterized. ADC-1 and CD19 mAb binds to CD19 endogenously expressed on the surface of multiple B cell lymphoma cell lines. ADC-1 elicited potent anti-proliferative effects and ADCC activity against multiple B cell malignancy cell lines. Furthermore, ADC-1 activates NFAT ADCC reporter cells expressing F158 or V158 FcγRIIIa variants with similar potency. While ADC-1 displayed negligible binding to murine or rat CD19, it displayed high affinity binding to both human and cynomolgus monkey (cyno) CD19 and activated GRE reporter cell lines expressing human or cyno CD19.

9.3.1. Materials and Methods

9.3.1.1. Antibodies, Proteins, and Compounds

The humanized anti-CD19 antibody (CD19 mAb) was afucosylated with ProBiogen technology. ADC-1 was made by conjugating CD19 mAb to the drug linker of Formula V. GLP material for CD19 mAb and ADC-1 were used for all experiments. Negative control tested include afucosylated anti-tetanus toxoid antibody AB095 (Isotype mAb) and its ADC (Isotype-GRM), consisting of AB095 conjugated to the drug linker of Formula V. Compounds analyzed include the GRM of Formula IV, dexamethasone (Clinigen, cat #00641-0367-25) and prednisolone (Clinigen, cat #44523-0182-08).

9.3.1.2. Cell Culture

The cancer cell lines Raji (Burkitt's lymphoma; ATCC, cat #CCL-86), SUP-B15 (Acute lymphoblastic leukemia; ATCC, cat #CRL-1929), RS4; 11 (Acute lymphoblastic leukemia; ATCC, cat #CRL-1873), SU-DHL-6 (Diffuse large B-cell lymphoma; ATCC, cat #CRL-2959) and HCT116 (Colorectal cancer; ATCC, cat #CCL-247) were cultured in RPMI-1640 media (Thermo Fisher Scientific, cat #A1049101) supplemented with 10% FBS (Thermo Fisher Scientific, cat #26140079). The cancer cell line OCI-LY19 (Diffuse large B-cell lymphoma; DSMZ, cat #ACC 528) were cultured in IMDM media with 10% human serum, from platelet poor human plasma, sterile filtered (Sigma-Aldrich, cat #P2918-100ML). 293T (ATCC, cat #CRL-3216) cells were cultured in DMEM supplemented with 10% FBS. All cells are cultured in a humidified chamber at 37° C. and 5% $CO_2$.

9.3.1.3. Generation of Engineered Cell Lines

The K562 GRE luciferase reporter cell line expressing human CD19 were generated at AbbVie. Briefly, K562 cells were seeded onto 6-well dish (Costar, cat #3516) with 2 mL of complete growth medium [RPMI 1640 supplemented with L-Glutamine (Thermo Fisher Scientific, cat #11835-030), 10% FBS (Thermo Fisher Scientific Inc., cat #26140-079), 1% Na Pyruvate (Thermo Fisher Scientific Inc., cat #11360-070) and 1% MEM NEAA (Thermo Fisher Scientific Inc., cat #111140-50)] at 500,000 cells per well for 24 hours at 37° C. and 5% $CO_2$. The next day, 1.5 μg of pGL4.36 [Luc2P/MMTV/Hygro] (Promega cat #E316), and 3 μL of PLUS reagent (Thermo Fisher Scientific, cat #10964-021) were diluted into 244 μL Opti-MEM (Thermo Fisher Scientific, cat #31985-070) and incubated at room temperature for 15 minutes. After incubation, diluted DNA solution was pre-incubated with 1:1 Lipofectamine LTX solution (Thermo Fisher Scientific, cat #94756) (13.2 μL+256.8 μL Opti-MEM) and incubated at room temperature for 25 minutes to form DNA-Lipofectamine LTX complexes. After incubation, 500 μL of DNA-Lipofectamine complexes were added directly to the well containing cells. K562 cells were transfected for 24 hours at 37° C. and 5% $CO_2$. After incubation, cells were washed with 3 mL of PBS and selected with complete growth medium containing 125 μg/mL of hygromycin B (Thermo Fisher Scientific, cat #10687-010) for two weeks.

K562 pGL4.36[Luc2P/MMTV/Hygro] cells were harvested and seeded into a 15-mL conical tube (Costar, cat #3516) with 1 mL of complete growth medium (RPMI+L-Glu, 10% FBS, 1% Na Pyruvate and 1% MEM NEAA) at 250,000 cells per well. 3 μg of human CD19 (Origene, #RC230267) and 3 μL of PLUS reagent (Thermo Fisher Scientific, cat #10964-021) were diluted into 244 μL Opti-MEM (Thermo Fisher Scientific, cat #31985-070) and incubated at room temperature for 5 minutes. After incubation, diluted DNA solution was pre-incubated with 1:1 Lipofectamine LTX solution (Thermo Fisher Scientific, cat #94756) (11 μL+239 μL Opti-MEM) and incubated at room temperature for 15 minutes to form DNA-Lipofectamine LTX complexes. Subsequently, 500 μL of DNA-Lipofectamine complexes were added directly to conical tube containing cells. The cells and DNA-lipofectamine were mixed and seeded into a 6-well dish (Costar, cat #3516) and incubated for 24 hours at 37° C. and 5% $CO_2$. After 24-hour incubation, the cells were selected with 2 ml complete growth medium containing 125 μg/mL of hygromycin B (Thermo Fisher Scientific, cat #10687-010) and 225 μg/mL G418 (Thermo Fisher Scientific, cat #10131-027) for two weeks.

9.3.1.4. Cell Proliferation Assay

Adherent cells (293T and HCT116) were detached by trypsinization. 1000-2000 cells per well were plated on 384-well tissue culture plates (Corning, cat #3764) in 40 μL in complete RPMI 1640. The adherent cells are allowed to attach overnight. Next day, the cells are treated with indicated concentrations of drugs in 10 μL and incubated at 37° C. with 5% $CO_2$ for 5 days. At the endpoint, 40 μL of a cell viability assay reagent (CellTiter-Glo® Luminescence Cell Viability Assay Reagent (Promega, cat #G7573)) were added per well. Plates were read on a microplate reader (Molecular Devices SpectraMax® M5 microplate reader) with Luminescence setting. The cell viability was expressed as a percentage relative to the untreated controls.

9.3.1.5. Immunofluorescence

RS4; 11 cell line was plated onto V-bottom plates (Costar Cat #3894) at 50k cells per well. The cells were Fc blocked with PBS+5% normal human serum (Sigma cat #H4522) and 2% FBS. The cells were washed and resuspended in staining buffer (PBS+2% FBS). The cells were stained with a dye (Alexa Fluor® 647 dye) conjugated anti-hu-CD19 antibody (CD19 mAb) at 5 μg/mL in staining buffer and incubated on ice for 1h. After incubation, the cells were washed three times with PBS containing 2% FBS and chased at 37C for 0.5h, 1, 3, and 24h to induce internalization and compared to cells stained on ice for a T=0 time point control. The cells were than fixed and permeabilized (BD, Cat #554714) using manufacturing instructions. Cells were blocked with staining buffer containing 1% saponin+ 2% mouse serum (Invitrogen Cat #3881) and stained with 2 μg/mL, fluorescent dye (Alexa Fluor® 488 dye) conjugated LAMP1 antibody (Biolegend, Cat #328610) overnight at 4° C. The cells were washed 3 times in PBS containing 2% FBS. The cells were resuspended in imaging media (FluoroBrite™: Gibco cat #A1896701) and transferred to glass bottom imaging plates (Thermo Fisher Scientific, cat #160376) and analyzed on a confocal imager (IMX Micro Confocal imager).

9.3.1.6. Immunoblots

SU-DHL-6 cells were treated with isotype mAb or CD19 mAb for an hour and then stimulated with 1 µg/ml anti-IgM for 0, 5, 15 or 30 minutes. The cells were harvested by washing twice with iced-cold PBS and then lysed in RIPA lysis buffer (Sigma-Aldrich, cat #R0278) supplemented with phosphatase inhibitor (1×Halt™ Protease and Phosphatase Inhibitor Cocktail, Thermo Fisher Scientific, cat #78446). The protein concentrations of the lysates were measured with BCA Protein Assay Kit (Thermo Fisher Scientific, cat #23227). 10-20 µg of lysates were resolved on 4-12% gradient gels (Thermo Fisher Scientific, cat #NW04120BOX) and transferred onto a nitrocellulose membrane (Thermo Fisher Scientific, cat #IB23001). The membranes were incubated with primary antibodies at the manufacturer's suggested concentration at 4° C. overnight. The primary antibodies used in this study include phospho-AKT Ser473 (Cell Signaling Technology, cat #4060) or GAPDH (Cell Signaling Technology, cat #97166). The membranes were washed three times with 1×PBST (Cell Signaling Technology, cat #9809) and subsequently incubated with a secondary antibody (Peroxidase AffiniPure Goat Anti-Mouse IgG (H+L), Jackson ImmunoResearch Laboratories, cat #115-035-003 or Peroxidase AffiniPure Goat Anti-Rabbit IgG (H+L), Jackson ImmunoResearch Laboratories, cat #111-035-003) for 1 hour at room temperature. The membranes were washed three times with 1×PBST and then incubated with western blot substrate (Pierce™ ECL Western Blotting Substrate, Thermo Fisher Scientific, cat #32106). The membranes are then detected with a western blot imaging system (Azure Image Systems C600).

9.3.1.7. Glucocorticoid Response Element (GRE) Activation Assay

K562 parental GRE (pGL4.36[luc2P/MMTV/Hygro]) and K562 human CD19 GRE (pGL4.36[luc2P/MMTV/Hygro]) or K562 cynomolgus CD19 GRE (pGL4.36[luc2P/MMTV/Hygro]) cells were plated onto 96-well tissue culture-treated white plates (Costar, cat #3917) at 50,000 cells per well in 75 µL of assay medium (1×RPMI+L-Glu, 1% CSFBS (Thermo Fisher Scientific Inc., cat #12676-029), 1% Na Pyruvate and 1% MEAA). The GRE K562 parental cells or cells expressing human CD19 and cynomolgus CD19 were treated with 25 µL of 4× serial diluted CD19-GRM in assay medium and incubated for 72 hours at 37° C. and 5% $CO_2$. 100 nM dexamethasone were added as positive control in these assays. After 72 hours incubation, cells were treated with 100 µL of Dual-Glo Luciferase Assay System (Promega cat #E2920) for 10 minutes and analyzed for luminescence using the MicroBeta (PerkinElmer). The dose-response data were fitted to a sigmoidal curve using nonlinear regression and the EC50 values calculated with the aid of GraphPad 9.0 (GraphPad Software, Inc.).

9.3.1.8. NFAT ADCC Reporter Assay

The ADCC Reporter Bioassay (V and F variants; Promega, cat #G7010 and G9790) were performed according to the manufacturer's protocol with minor modifications. Briefly, the target cell line Raji was plated in 5 µL of ADCC assay buffer (RPMI media containing 4% low IgG serum) at 2500 cells per well. The antibody was titrated in ADCC assay buffer and 5 µL were added at indicated antibody concentration. Effector cells from the V Variant and F Variant kits were resuspended in ADCC assay buffer and added at 5 µL per well to achieve effector to target cell ratio of 6:1. The target cell-antibody mixtures were incubated with effector cells expressing V variant and F variant at 37° C. for 6 hours and 24 hours, respectively. At the endpoint, 15 µL of Bio-Glo Luciferase Reagents were added and luciferase activity were measure with Molecular Devices SpectraMax M5 plate reader.

9.3.1.9. PBMC Co-culture ADCC Assay

The target cell lines (RS4; 11, Raji and KARPAS422) were washed with PBS and labelled with 1 µM CFSE in PBS (Thermo Fisher Scientific, cat #C34554) for 5 minutes at 37° C. The labelled target cells were then washed 3 times with media containing 10% FBS. 20,000 labeled target cells in 50 µL are plated onto V-shaped 96-well plates. Antibodies and ADCs were titrated in culture media and 10 µL were added to achieve indicated final concentrations. PMBC from normal donor (AllCells) were added in 40 µL at effector to target cell ratio of 20:1 and the cells were incubated at 37° C. for 4 hours. After the incubation, the cells are washed once with PBS and stained with Live/Dead Fixable Violet Dead Cell Stain Kit (Thermo Fisher Scientific cat #L34955) for 30 minutes at room temperature and then wash once with 200 µL ice-cold PBS. Cells are fixed with 4% paraformaldehyde in PBS for 15 minutes and then wash once with 200 µL PBS. The fixed cells are resuspended in 100 µL PBS and store in 4° C. until analysis on Stratedigm S1000EON flow cytometer. The percentage of Live/Dead Violet dye-positive cells were captured, and % specific lysis was calculated by subtracting the percentage of Live/Dead Violet-positive cells in each treated conditions with the untreated control containing only effector and target cells.

9.3.1.10. ADCP Assay

Human monocytes (STEMCELL Technologies) were differentiated into macrophages for 8 days in RPMI-1640 containing 10% FBS and 50 ng/ml of recombinant human M-CSF (BioLegend). Fully differentiated macrophages were detached from flasks to be co-cultured with target cancer cells in the phagocytosis assays. The human Non-Hodgkins Lymphoma cell line Raji and NuDHL1 expressing endogenous CD19 were selected as target cells. After washing with PBS, the target cancer cells were labeled with 5 µM of CFSE dye solution (Thermo Fisher Scientific) for 15 min, then co-incubated with human macrophage at 1:1 ratio. CD19 mAb or CD19-GRM were added at various concentrations. After co-culture for 3 hours at 37° C., cells were harvested, washed and stained antibody against a macrophage maturation marker, APC-Cy7 labeled CD68 antibody (BioLegend), followed by flow cytometry analysis. Phagocytosis index was calculated by counting CFSE+CD68+ double-positive macrophages among total CD68+ macrophages, which shows the population percentile of phagocytosing macrophages.

9.3.1.11. Apoptosis Assay

Apoptosis was detected using a Western blot assay. DLBCL cell lines Farage, SU-DHL-6, OCI-LY19 cells were treated with GRM payload (100 nM) or ADC-I (1 µM) for the times indicated before cell lysis. Cell lysates were generated using a protein extraction reagent (M-PER™ Mammalian Protein Extraction Reagent, Thermo Fisher Scientific, cat #78501) and protein concentration was determined using a Bradford assay (Pierce™ Detergent Compatible Bradford Assay Kit, Thermo Fisher Scientific, cat #23246). Protein lysates (10 µg) from each treatment condition were resolved on a polyacrylamide gel (Bolt™ 4 to 12%, Bis-Tris) and transferred to PVDF membrane with a gel transfer device (iBlot™ 2 Gel Transfer Device). The membrane was blocked with 5% BSA and then immunoblotted with antibodies against proteins of interest: BIM (Cell Signaling, cat #2933), caspase 3 (Cell Signaling, cat #9662), P ARP (Cell Signaling, cat #9532) and GAPDH (Cell Signaling, cat #5174). The membranes were subsequently probed with Horseradish Peroxidase (HRP) conjugated secondary antibody against rabbit or mouse IgG and detected with a chemiluminescent horseradish peroxidase substrate (SuperSignal™ West Pico PLUS Chemiluminescent substrate, Thermo Fisher Scientific, cat #34580) on a western blot imaging system (Azure Imager).

9.3.2. In Vivo Studies

9.3.2.1. Mice and Husbandry

Female CB17/SCID and SCID/beige were obtained from Charles River (Wilmington, MA) and the CD34+ humanized NSG IL-15 were obtained from The Jackson Laboratory (Bar Harbor, ME), at 6 to 8 weeks of age and housed at a maximum of 10 per cage. The body weight upon arrival was 18 to 20 g. Food and water were available ad libitum. Mice were acclimated to the animal facilities for a period of at least three days prior to commencement of experiments. Animals were tested in the light phase of a 12-hour light: 12-hour dark schedule (lights on at 06:00 hours). All experiments were conducted in compliance with AbbVie's Institutional Animal Care and Use Committee and the National Institutes of Health Guide for Care and Use of Laboratory Animals guidelines.

9.3.2.2. Compounds

Intraperitoneal route of administration was used. The GRM small molecule (GRM-SM) was formulated in 0.05% HPMC, 0.02% Tween-80 in water and stored at 4° C., with oral dosing.

CD19 mAb from Example 1 is an afucosylated monoclonal antibody (IgG1, κ) that has high affinity to human and cynomolgus monkey CD19. ADC-1 is a conjugate of CD19 mAb linked with a bromoacetamide alanine-alanine peptide linker to the GRM molecule of Formula V. The isotype antibody (AB095) recognizes tetanus toxoid antigen which is not displayed by the xenograft nor by any murine tissues.

9.3.2.3. Parameters of Efficacy

Parameters of amplitude (maximum tumor growth inhibition, [$TGI_{max}$]) and durability (tumor growth delay, TGD) of therapeutic response are used to refer to the efficacy of the drug. TGI indicates the divergence between the mean tumor volume of a drug-treated group and the mean tumor volume of the control group treated with drug vehicle or isotype matched non-binding antibody and is expressed as a percentage of the mean volume of the control group. The $TGI_{max}$-value is determined at the time when the difference between treated, and control group is maximal. The $TGD_{(n)}$ indicates the difference of the median time of a drug treated group to reach a defined tumor volume (1 cm$^3$) as compared to the median time of a control group treated with vehicle to reach the same volume. This difference is expressed as a percentage of the median time of the control group to reach the specified tumor volume.

9.3.2.4. Generation of Tumor Bearing Mice and Determination of Tumor Volume of Subcutaneous Flank Tumors For each subcutaneous xenograft study, viable cells were inoculated into the right flank of mice on Day 0. The injection volume was 0.1 mL composed of a 1:1 mixture of S-MEM or HBSS (Fisher Scientific, MA) and Matrigel (BD, Franklin Lakes, NJ). Tumors were size matched at approximately 80 to 200 mm$^3$. Therapy usually began within 24 hours following randomization and size matching of tumors into required cohorts. Mice weighed approximately 20-22 g at the onset of therapy. Tumor volume was estimated one to two times weekly. Measurements of length (L) and width (W) of the tumor were obtained via electronic calipers and volume was calculated according to the following equation: $V=(L \times W^2)/2$. Mice were euthanized when tumor volume reached a maximum of 2,000 mm$^3$ or if animal health was compromised, per institutional guidelines.

9.3.2.5. Statistics

Data from experiments in vivo were analyzed using the Student's t-test for $TGI_{max}$ values and a log-rank test (Mann-Whitney U-test or Mantel Cox) for TGD. Differences in response rates were assessed by the Fisher exact test.

9.3.2.6. PDX Studies

Patient derived xenograft (PDX) studies were performed in DLBCL models established at WuXi, which originated from surgically resected primary patient tumors. Patient treatment history was collected according to protocols and guidelines established by institutional review boards. Each tumor specimen (single cell suspension or tumor fragments) was prepared in Matrigel (BD Biosciences) and implanted on the flank of 6- to 8-week-old NOD scid mice. Mice were handled and housed in accordance with IACUC/AALAS protocols and procedures. Tumors were measured twice weekly via caliper measurements (length×width$^2$)/2 and treatment was initiated when tumor volumes reached approximately 150-200 mm$^3$. Mice were treated intraperitoneally once with the test articles as indicated with n=5/group (vehicle, CD19 antibody, ADC-1). For each DLBCL PDX model tested (6 germinal center B-cells (GCB) and 4 non-GCB, including a hard to treat non-GCB activated B-cell subtype (ABC)) the tumor growth inhibition following ADC-1 treatment was determined as follows: Delta % TGI max=1-(tumor volume of treated group on day X—tumor volume of treated group at randomization)/(tumor volume of control on day X—tumor volume of control at randomization)]*100. The Delta % TGI max was determined when the difference between treatment and control groups were maximal. A PDX model was determined to be a responder or non-responder based on its ability to induce tumor regression (responder): >105% delta TGI max—yes/no response. The tumor volume change (%) was also calculated and graphed based on the time point when vehicle control tumors had reached 1000 mm$^3$, as calculated by

[(tumor volume at time point/tumor volume at randomization)−1]×100. See FIG. 13A-B.

9.3.2.7. Binding Activity

Flow cytometry was used to assess cell surface binding of ADC-1 to different cancer cell lines endogenously expressing CD19 and 293T cells transduced with full-length human CD19. ADC-1 displayed binding $EC_{50}$ ranging from 0.544 to 1.061 nM on B cell lymphoma cell lines Raji (Burkitt's lymphoma), SUP-B15 (Acute Lymphoblastic Leukemia), RS4; 11 (Acute Lymphoblastic Leukemia), and OCI-LY19 (Diffuse Large B cell Lymphoma) (Table 4), and binding $EC_{50}$ of 1.086 nM on 293T cells engineered with full-length human CD19 (Table 4). The unconjugated parental afucosylated CD19 antibody of Example 1 (CD19 mAb) displayed similar binding affinity with $EC_{50}$ ranging from 0.401 to 0.836 nM (Table 4), and binding $EC_{50}$ of 0.977 nM on 293T cells engineered with full-length human CD19 (Table 4). Both ADC-1 and CD19 mAb did not exhibit detectable binding to CD19-negative colorectal cancer cell line HCT116.

TABLE 4

Binding Affinity of ADC-1 to Cellular CD19

| | Binding $EC_{50}$ (nM)[a] | |
| --- | --- | --- |
| | CD19 mAb | ADC-1 |
| Cellular CD19 by Flow Cytometry | | |
| OCI-LY19 (DLBCL) | 0.836 | 1.061 |
| Raji (BL) | 0.713 | 0.939 |
| RS4; 11 (ALL) | 0.401 | 0.544 |
| SUP-B15 (ALL) | 0.683 | 0.928 |
| HCT116 (CD19-negative - CRC) | n.d. | n.d. |
| Engineered Cellular CD19 by Flow Cytometry | | |
| 293T Human CD19 Engineered Cell Line | 0.977 | 1.086 |
| Parental 293T cells | n.d. | n.d. |

ALL = acute lymphoblastic leukemia;
BL = Burkitt's lymphoma;
CRC = colorectal cancer;
DLBCL = diffuse large B cell lymphoma,
n.d. = not detected
[a]The average $EC_{50}$ from two independent experiments are displayed.

9.3.2.8. Glucocorticoid Receptor Modulator (GRM) Payload Is More Potent Than Clinically Approved Glucocorticoids The potency of GRM payloads was compared with clinically approved glucocorticoids (dexamethasone and prednisolone) by testing on RS4; 11 cells in vitro. The GRM payload of Formula IV showed higher potency compared to either dexamethasone or prednisolone (FIG. 1). The $EC_{50S}$ were 0.23 nM, 3.28 nM and 82.91 nM for the GRM payload of Formula IV, dexamethasone and prednisolone, respectively.

9.3.2.9. CD19 mAb and ADC-1 Internalize and Deliver GRM Payload To Inhibit B-cell Lymphoma Cell Proliferation To investigate the ability of CD19 mAb to induce CD19 internalization, the acute lymphoblastic lymphoma (ALL) cell line RS4; 11 was treated with CD19 mAb at 37° C. for 0, 0.5, 1, 3, and 24 hours. CD19 mAb induces CD19 internalization as early as 0.5 hour and localizes to the lysosome, as indicated by the co-localization of CD19 with the lysosomal marker LAMP1 (FIG. 2). Likewise, ADC-1 activates GRE reporter in a dose-dependent manner in K562 glucocorticoid response element (GRE) reporter cells, which was engineered to express human CD19 (FIG. 3).

To evaluate the cytotoxicity of ADC-1, proliferation assays were performed on cell lines expressing different levels of CD19. ADC-1 inhibited the proliferation of CD19-expressing cancer cell lines that are sensitive to the glucocorticoid receptor modulator (GRM) payload of Formula IV and the in vitro cytotoxicity $EC_{50}$ of ADC-1 ranging from 0.082-0.321 nM (Table 5).

TABLE 5

CD19 Expression and Sensitivity to ADC-1 and Formula IV Treatment in Cell Lines In Vitro

| | CD19 Receptor Copy Number (thousands)[a] | Compound of Formula IV $EC_{50}$ (nM)[b] | ADC-1 $EC_{50}$ (nM)[b] | Isotype-GRM $EC_{50}$ (nM)[b] |
| --- | --- | --- | --- | --- |
| SUP-B15 (ALL) | 109.3 | 0.089 | 0.321 | 43.1 |
| RS4; 11 (ALL) | 113.9 | 0.100 | 0.082 | 69.7 |
| OCI-LY19 (DLBCL) | 98 | 0.675 | 103 | 511 |
| KARPAS422 (DLBCL) | 308.1 | 0.093 | 0.210 | 43.3 |
| SU-DHL-6 (DLBCL) | 52.3 | 1.519 | 0.311 | 227 |
| HCT116 (CRC) | n.d. | >1000 | >1000 | >1000 | n.d. = not detected
DLBCL = diffuse large B cell lymphoma,
BL = Burkitt's lymphoma,
ALL = acute lymphoblastic lymphoma,
CRC = colorectal cancer
[a]Approximate number of cell surface CD19 molecules per cells as determined by flow cytometry as antibody binding capacity for CD19 mAb binding at 67 nM.
[b]The average $EC_{50}$ from anti-proliferative assay in two independent experiments are displayed. $EC_{50}$ values are representative of complete cell killing as observed for Formula IV and CD19-GRM.

The GRM pro-drug payload of Formula III is dephosphorylated in vitro/in vivo to the dephosphorylated GRM payload of Formula IV, and thus the dephosphorylated payload of Formula IV was used as the control in our studies. ADC-1 was not active on the CD19-negative colorectal cancer cell line HCT116 (Table 5). Notably, ADC-1 was more potent compared to the isotype-GRM (Table 5), indicating CD19 target-dependent delivery of GRM payload.

9.3.2.10. CD19 mAb Inhibits DLBCL Cell Proliferation and AKT Activation In Vitro CD19 is a co-receptor for B cell receptor and can transactivate the PI3K/AKT pathway (Burger, et al., Nat Rev Cancer, 2018. 18(3): p. 148-167). Moreover, functional genomic screening demonstrated that a subset of DLBCL cell lines is dependent on CD19 for survival (Phelan, J. D., et al., Nature, 2018. 560(7718): p. 387-391. CD19 mAb (from Example 1) treatment inhibited the cell proliferation of SU-DHL-6 in vitro (FIG. 4A). The pre-treatment of CD19 mAb ablated AKT phosphorylation in response to BCR stimulation with 1 µg/ml anti-IgM (FIG. 4B), demonstrating that CD19 mAb can effectively block BCR-mediated AKT pathway activation.

9.3.2.11. ADC-1 Mediates Antibody-Dependent Cellular Cytotoxicity (ADCC)

CD19 mAb and ADC-1 have been afucosylated to enhance their ability to elicit antibody-dependent cellular cytotoxicity (ADCC). The polymorphisms on FcγRIIIa (F158 or V158) affect its binding to IgG1, IgG3 and IgG4 and the therapeutic efficacy of these antibodies (Koene, H. R., et al., Blood, 1997. 90(3): p. 1109-1114; Cartron, G., et al., Blood, 2002. 99(3): p. 754-8; Wu, J., et al., J Clin Invest, 1997. 100(5): p. 1059-70).

NFAT reporter Jurkat cells engineered to express high-affinity (V158) or low-affinity (F158) FcγRIIIa were used to determine the ability of CD19-GRM to bind FcγRIIIa and elicit ADCC in vitro. CD19-GRM induced ADCC NFAT reporter activation with $EC_{50}$ of 0.017 nM and 0.018 nM on V158 and F158 variants, respectively (FIGS. 5 A and B). Similarly, the unconjugated afucosylated antibody CD19 mAb also induced potent ADCC activity with $EC_{50}$ of 0.027 nM and 0.023 nM on V158 and F158 variants, respectively (FIGS. 5 A and B).

The co-culture of B-cell lymphoma cell lines with primary PBMC were performed to functionally assess ADCC activity of ADC-1. In these assays, ADC-1 elicited CD-19-specific cancer cell lysis with $EC_{50}$ ranging from 0.07-0.142 nM (FIG. 6 A-C). The unconjugated CD19 mAb also displayed similar CD19-specific cancer cell lysis with $EC_{50}$ ranging from 0.075-0.405 nM (FIG. 6 A-C).

9.3.2.12. ADC-1 Induces Antibody-Dependent Cellular Phagocytosis (ADCP)

The ability of ADC-1 to induce ADCP was evaluated by the co-culture of B-cell lymphoma cells with monocyte-derived macrophages in vitro. Both ADC-1 and CD19 mAb treatments resulted in markedly higher ADCP induction compared to Isotype mAb or Isotype-GRM treatments in NuDHL1 and Raji (FIGS. 7 A and B).

9.3.2.13. GRM and ADC-1 Induce Apoptosis in DLBCL Cell Lines

GRM and ADC1 induced apoptosis as measured by upregulation of proapoptotic protein (BIM) and induction of markers of apoptosis (cleaved caspase-3 and cleaved PARP) in all 3 cell lines tested (see FIG. 15).

9.3.2.14. ADC-1 Elicits GRM-driven Anti-tumor Activity and ADCC In Vivo

ADC-1 is efficacious in tumors with cell surface expression of CD19. Given as a single agent, ADC-1 inhibits subcutaneous xenograft growth of human tumor cell lines derived from B-cell malignancies such as Diffuse Large B-Cell Lymphoma (DLBCL: OCI-LY19 and SU-DHL-6) and Acute Lymphoblastic Leukemia (ALL: RS4; 11) (FIGS. 8 and 9). Human xenografts were studied using immune-compromised CB17/SCID mice (OCI-LY19, RS4; 11: FIG. 8A and FIG. 9), immune-compromised SCID/beige mice (SU-DHL-6: FIG. 8B) and humanized CD34+ NSG-huIL-15 mouse model (OCI-LY19: FIG. 10). ADC-1 is efficacious in a dose-dependent manner administered intraperitoneally as a single bolus. In the DLBCL xenografts (FIG. 8), ADC-1 at all doses and Glucocorticoid Receptor Modulator small molecule of Formula IV (GRM-SM) induced a statistically significant ($p<0.05$) tumor growth inhibition, greater than the vehicle, isotype monoclonal antibody, human CD19 monoclonal antibody and systemic steroid (Prednisolone, daily dosing). Significant durable responses were observed at the highest dose in the DLBCL xenografts. The AB095-GRM (Isotype-GRM control) showed some growth inhibition at the two highest doses, which was significantly less ($p<0.05$) than ADC-1 at the same doses. ADC-1 administered in the ALL xenograft model (FIG. 9), showed high sensitivity with durable responses at low doses and statistically significant ($p<0.05$) tumor growth inhibition. Tumor regression at dose 2 lasted >100 days. All doses were tolerated, and no body weight reductions were observed.

ADC-1 is efficacious in a dose-dependent manner in an Antibody Dependent Cell Cytotoxicity (ADCC) compatible mouse model (huCD34+ NSG-huIL-15). In this mouse model, immune-compromised NSG mice are genetically engineered to express human IL-15 and engrafted with human PBMCs (CD34+). The human IL-15 supports NK cell viability and function enabling the study of ADCC. In this mouse system ADC-1 induced inhibition of subcutaneous xenograft growth of human tumor cell lines derived from DLBCL (OCI-LY19: FIG. 10). Statistically significant ($p<0.05$) tumor growth inhibition and durable responses (>50 days) were observed at dose 3. The impact of ADC-1 on human peripheral blood B cells and NK cells was measured at baseline (4 days pre-dose) and 1, 6, 13, 20, and 26 days after dosing. Both the number of human B cells per microliter of mouse blood and as a percentage of total human CD45+ cells were reduced for all ADC-1 dose levels. The duration of B cell suppression was positively associated with dose level. NK cell numbers were not significantly impacted by ADC-1 at any dose level.

The efficacy of ADC-1 was also directly compared to CD19 mAb and systemic prednisolone combination in RS4; 11 xenograft model. In this model, high-dose single-agent CD19 mAb or prednisolone (QD×5]×3) displayed modest anti-tumor activity while the combination of both agents led to more sustained tumor growth inhibition (FIG. 11). Notably, the treatment of single low-dose ADC-1 induced more durable anti-tumor activity compared to CD19 mAb and systemic prednisolone ([QD×5]×3) combination.

ADC-1 demonstrates anti-tumor efficacy in a number of different B-cell malignancy models, DB (FIG. 12A), SUPB15 (FIG. 12B), RS4; 11 (FIG. 12C). Anti-tumor efficacy of ADC-1 was directly compared to prednisolone,

[QD×5]×3 or isotype-GRM ADC in DB and SUPB15 xenograft models grown in immune-compromised mice as indicated. Sustained anti-tumor efficacy was observed in both DB and SUPB15 xenograft models that was superior to systemic steroid prednisolone and superior to isotype-GRM ADC confirming CD19-targeted activity of the ADC-1. The ALL tumor model SUPB15 (FIG. 12B) demonstrates sustained anti-tumor activity (complete responses) lasting more than 50 days after a single ADC-1 dose. RS4; 11 tumors (FIG. 12C) were allowed to grow to a large size (>600 mm³) and were then treated with ADC-1 with a single IP dose. This single ADC-1 administration resulted in complete tumor regression of these large tumors that was sustained for >40 days.

9.3.2.15. ADC-1 Elicits Anti-tumor Activity in DLBCL PDX Models

As shown in FIG. 13 A, all 10 DLBCL PDX models demonstrated tumor growth inhibition relative to control treated PDXs of the same model. Nine out of the 10 models exhibited tumor regression using a single dose of ADC-1 at dose 3 (see FIG. 13B). Anti-tumor efficacy was seen in PDX models derived from both GCB and Non-GCB patients. Only one model, 0232, did not show stasis or regression when treated with dose 3 of ADC-1. This PDSX model was from a patient that underwent 7 cycles of R-CHOP treatment. 3 PDX models from R-CHOP recurrent patients treated for 4 cycles, 0367, 0016 and 0207, did respond.

As shown in FIGS. 14 A and B, a single dose of ADC-1 at dose 3 demonstrated anti-tumor activity when compared to the vehicle control and the CD19 antibody treatments. In FIG. 14A, the PDX model was derived from a DLBCL—GCB patient who had been treated with 4 cycles of R-CHOP. This PDX model exhibits a slight stasis when treated with ibrutinib. The PDX derived model shown in FIG. 14B was from a DLBCL ABC patient that had received 4 cycles of R-CHOP. This PDX model is resistant to ibrutinib treatment.

What is claimed:

1. An anti-CD19 antibody-drug conjugate comprising the following structure:

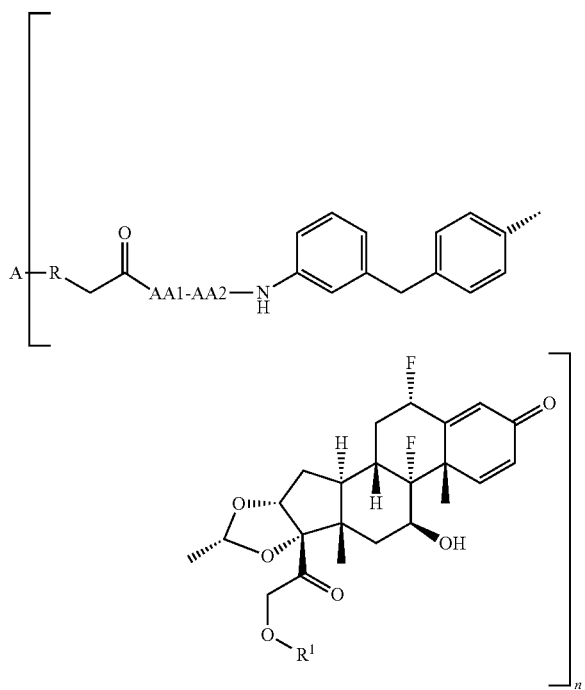

wherein:

A is an anti-CD19 IgG$_1$ antibody;

R is the point of attachment of the antibody via a cysteine residue of the antibody providing an —S— group when linked;

AA1 and AA2 are each Alanine (Ala);

R$^1$ is P(=O)(OH)$_2$;

n is 2, 4, or 6;

wherein the antibody comprises:

two heavy chains, wherein both heavy chains each consist of either the amino acid sequence set forth as SEQ ID NO: 9 or SEQ ID NO: 11; and two light chains, wherein both light chains each consist of the amino acid sequence set forth as SEQ ID NO: 10; and wherein the antibody is afucosylated at position 303 of SEQ ID NO: 9 or SEQ ID NO: 11.

2. The anti-CD19 antibody-drug conjugate of claim 1, wherein the heavy chain sequence is SEQ ID NO: 9.

3. The anti-CD19 antibody-drug conjugate of claim 1, wherein the heavy chain sequence is SEQ ID NO: 11.

* * * * *

```
                        SEQUENCE LISTING

Sequence total quantity: 13
SEQ ID NO: 1            moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 1
GFTFTTYWIN                                                                10

SEQ ID NO: 2            moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 2
NIYPSDSYTN YNQKFKD                                                        17

SEQ ID NO: 3            moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 3
EDYYGSSSYY AMDY                                                           14

SEQ ID NO: 4            moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 4
KASQDVGTAV A                                                              11

SEQ ID NO: 5            moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 5
WASTRHT                                                                   7

SEQ ID NO: 6            moltype = AA  length = 9
FEATURE                 Location/Qualifiers
```

| | | |
|---|---|---|
| REGION | 1..9 | |
| | note = Description of Artificial Sequence: Synthetic peptide | |
| source | 1..9 | |
| | mol_type = protein | |
| | organism = synthetic construct | |

SEQUENCE: 6
```
QQYSTYPLT                                                             9
```

| | | |
|---|---|---|
| SEQ ID NO: 7 | moltype = AA  length = 123 | |
| FEATURE | Location/Qualifiers | |
| REGION | 1..123 | |
| | note = Description of Artificial Sequence: Synthetic polypeptide | |
| source | 1..123 | |
| | mol_type = protein | |
| | organism = synthetic construct | |

SEQUENCE: 7
```
EVQLVESGGG LVQPGGSLRL SCAASGFTFT TYWINWVRQA PGKGLEWIGN IYPSDSYTNY    60
NQKFKDRATL SVDKSKNTAY LQMNSLRAED TAVYYCTRED YYGSSSYYAM DYWGQGTLVT   120
VSS                                                                 123
```

| | | |
|---|---|---|
| SEQ ID NO: 8 | moltype = AA  length = 107 | |
| FEATURE | Location/Qualifiers | |
| REGION | 1..107 | |
| | note = Description of Artificial Sequence: Synthetic polypeptide | |
| source | 1..107 | |
| | mol_type = protein | |
| | organism = synthetic construct | |

SEQUENCE: 8
```
AILMTQSPSS LSASVGDRVT ITCKASQDVG TAVAWYQQKP GKAPKLLIYW ASTRHTGVPS    60
RFSGSGSGTD FTLTISSLQP EDFATYYCQQ YSTYPLTFGQ GTKVEIK                107
```

| | | |
|---|---|---|
| SEQ ID NO: 9 | moltype = AA  length = 453 | |
| FEATURE | Location/Qualifiers | |
| REGION | 1..453 | |
| | note = Description of Artificial Sequence: Synthetic polypeptide | |
| source | 1..453 | |
| | mol_type = protein | |
| | organism = synthetic construct | |

SEQUENCE: 9
```
EVQLVESGGG LVQPGGSLRL SCAASGFTFT TYWINWVRQA PGKGLEWIGN IYPSDSYTNY    60
NQKFKDRATL SVDKSKNTAY LQMNSLRAED TAVYYCTRED YYGSSSYYAM DYWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEL   240
LGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
REEMTKNQVS LTCLVKGFYP SDIAVEWESN GQPENNYKTT PPVLDSDGSF FLYSKLTVDK   420
SRWQQGNVFS CSVMHEALHN HYTQKSLSLS PGK                                453
```

| | | |
|---|---|---|
| SEQ ID NO: 10 | moltype = AA  length = 214 | |
| FEATURE | Location/Qualifiers | |
| REGION | 1..214 | |
| | note = Description of Artificial Sequence: Synthetic polypeptide | |
| source | 1..214 | |
| | mol_type = protein | |
| | organism = synthetic construct | |

SEQUENCE: 10
```
AILMTQSPSS LSASVGDRVT ITCKASQDVG TAVAWYQQKP GKAPKLLIYW ASTRHTGVPS    60
RFSGSGSGTD FTLTISSLQP EDFATYYCQQ YSTYPLTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214
```

| | | |
|---|---|---|
| SEQ ID NO: 11 | moltype = AA  length = 452 | |
| FEATURE | Location/Qualifiers | |
| REGION | 1..452 | |
| | note = Description of Artificial Sequence: Synthetic polypeptide | |
| source | 1..452 | |
| | mol_type = protein | |
| | organism = synthetic construct | |

SEQUENCE: 11
```
EVQLVESGGG LVQPGGSLRL SCAASGFTFT TYWINWVRQA PGKGLEWIGN IYPSDSYTNY    60
NQKFKDRATL SVDKSKNTAY LQMNSLRAED TAVYYCTRED YYGSSSYYAM DYWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEL   240
LGGPSVFLFP PKPKDTLMIS RTPEVTCVVV DVSHEDPEVK FNWYVDGVEV HNAKTKPREE   300
```

```
QYNSTYRVVS VLTVLHQDWL NGKEYKCKVS NKALPAPIEK TISKAKGQPR EPQVYTLPPS    360
REEMTKNQVS LTCLVKGFYP SDIAVEWESN GQPENNYKTT PPVLDSDGSF FLYSKLTVDK    420
SRWQQGNVFS CSVMHEALHN HYTQKSLSLS PG                                 452

SEQ ID NO: 12           moltype = DNA  length = 1419
FEATURE                 Location/Qualifiers
misc_feature            1..1419
                        note = Description of Artificial Sequence: Synthetic
                        polynucleotide
source                  1..1419
                        mol_type = other DNA
                        organism = synthetic construct
SEQUENCE: 12
atggagtttg ggctgagctg gcttttctt gtcgcgattt taaaaggagt ccagtgcgag     60
gtgcagctgg ttgaatctgg cggaggactg gttcagcctg gcggatctct gagactgtct   120
tgtgccgcca gcggcttcac cttcaccacc tactggatca ctgggtccg acaggcccct    180
ggcaaaggcc tggaatggat cggcaacatc taccccagcg acagctacac caactacaac   240
cagaagttca aggaccgggc cacactgagc gtggacaaga gcaagaatac cgcctacctg   300
cagatgaaca gcctgagagc cgaggacacc gccgtgtact actgcaccag agaggactac   360
tacggcagca gcagctacta cgccatggac tattggggcc agggcaccct ggttaccgtt   420
agctcagcct ccaccaaggg cccatcggtc ttccccctgg caccctcctc aagagcacc    480
tctgggggca gcggccct gggctgcctg gtcaaggact acttccccga accggtgacg    540
gtgtcgtgga actcaggcgc cctgaccagc ggcgtgcaca ccttccccgg ctgtcctacag   600
tcctcaggac tctactccct cagcagcgtg gtgaccgtgc cctccagcag cttgggcacc   660
cagacctaca tctgcaacgt gaatcacaag cccagcaaca ccaaggtgga caagaaagtt   720
gagcccaaat cttgtgacaa aactcacaca tgcccaccgt gcccagcacc tgaactcctg   780
gggggaccgt cagtcttcct cttccccccca aaacccaagg acaccctcat gatctcccgg   840
accctgagg tcacatgcgt ggtggtggac gtgagccacg aagaccctga ggtcaagttc   900
aactggtacg tggacggcgt ggaggtgcat aatgccaaga caaagccgcg ggaggagcag   960
tacaacagca cgtaccgtgt ggtcagcgtc ctcaccgtcc tgcaccagga ctggctgaat  1020
ggcaaggagt acaagtgcaa ggtctccaac aaagcccctc cagcccccat cgagaaaacc  1080
atctccaaag ccaagggca gccccgagaa ccacaggtgt acaccctgcc cccatcccgg   1140
gaggagatga ccaagaacca ggtcagcctg acctgcctgg tcaaaggctt ctatcccagc   1200
gacatcgccg tggagtggga gagcaatggg cagccggaga caactacaa gaccacgcct  1260
cccgtgctgg actccgacgg ctccttcttc ctctacagca agctcaccgt ggacaagagc   1320
aggtggcagc aggggaacgt cttctcatgc tccgtgatgc atgaggctct gcacaaccac   1380
tacacgcaga agagcctctc cctgtctccg ggtaaatga                          1419

SEQ ID NO: 13           moltype = DNA  length = 711
FEATURE                 Location/Qualifiers
misc_feature            1..711
                        note = Description of Artificial Sequence: Synthetic
                        polynucleotide
source                  1..711
                        mol_type = other DNA
                        organism = synthetic construct
SEQUENCE: 13
atggacatgc gcgtgcccgc ccagctgctg ggcctgctgc tgctgtggtt ccccggctcg     60
cgatgcgcca tcctgatgac acagagccct tctagcctga cgccagcgt gggagacaga   120
gtgaccatca cctgtaaagc cagccaggat gtgggaacag ccgtggcctg gtatcagcag   180
aagcctggaa aggcccctaa gctgctgatc tactgggcca gcacaagaca cacaggcgtg   240
cccagcagat tttctggcag cggctctggc accgacttca ccctgaccat atctagcctg   300
cagcctgagg acttcgccac ctactactgc cagcagtaca gcacataccc tctgaccttt   360
ggccagggca ccaaggtgga aatcaaacga actgtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata acgccctcca atcgggtaac   540
tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgtta g              711
```